(12) United States Patent
Li et al.

(10) Patent No.: US 10,889,569 B2
(45) Date of Patent: Jan. 12, 2021

(54) CONDENSED RING GROUP AZACYCLOBUTYL TRIAZOLE DERIVATIVE, PREPARATION METHOD THEREFOR AND USE THEREOF IN MEDICINE

(71) Applicants: Jiangsu Hengrui Medicine Co., Ltd., Jiangsu (CN); Shanghai Hengrui Pharmaceutical Co., Ltd., Shanghai (CN)

(72) Inventors: Xin Li, Shanghai (CN); Wei He, Shanghai (CN); Bin Wang, Shanghai (CN); Zhigao Zhang, Shanghai (CN); Feng He, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/471,069

(22) PCT Filed: Dec. 20, 2017

(86) PCT No.: PCT/CN2017/117421
§ 371 (c)(1),
(2) Date: Jun. 19, 2019

(87) PCT Pub. No.: WO2018/113694
PCT Pub. Date: Jun. 28, 2018

(65) Prior Publication Data
US 2020/0017466 A1    Jan. 16, 2020

(30) Foreign Application Priority Data
Dec. 21, 2016 (CN) .......................... 2016 1 1191169

(51) Int. Cl.
| | |
|---|---|
| *C07D 401/14* | (2006.01) |
| *C07D 405/14* | (2006.01) |
| *C07D 409/14* | (2006.01) |
| *C07D 413/14* | (2006.01) |
| *A61P 15/00* | (2006.01) |

(52) U.S. Cl.
CPC ............ *C07D 401/14* (2013.01); *A61P 15/00* (2018.01); *C07D 405/14* (2013.01); *C07D 409/14* (2013.01); *C07D 413/14* (2013.01)

(58) Field of Classification Search
CPC .. C07D 401/14; C07D 405/14; C07D 409/14; C07D 413/14; A61P 15/00
See application file for complete search history.

(56) References Cited

U.S. PATENT DOCUMENTS

2008/0214622 A1*  9/2008  Brown ............... A61P 1/16
514/340

FOREIGN PATENT DOCUMENTS

| CN | 101107243 A | 1/2008 |
|---|---|---|
| WO | 2005/028452 A1 | 3/2005 |
| WO | 2005/082866 A2 | 9/2005 |
| WO | 2006/077496 A1 | 7/2006 |
| WO | 2006/092731 A1 | 9/2006 |
| WO | 2006/100557 A1 | 9/2006 |
| WO | 2006/100588 A1 | 9/2006 |

OTHER PUBLICATIONS

Lan et al, "Atosiban improves implantation and pregnancy rates in patients with repeated implantation failure," Reproductive BioMedicine Online, vol. 25, No. 3, pp. 254-260 (2012).
Åkerlund, "Vascularization of Human Endometrium: Uterine Blood Flow in Healthy Condition and in Primary Dysmenorrhea," Annals New York Academy of Sciences, vol. 734, pp. 47-56 (1994).
Gimpl et al, "The Oxytocin Receptor System: Structure, Function, and Regulation," Physiological Reviews, vol. 81, No. 2, pp. 629-683 (2001).
Meston et al, "The Neurobiology of Sexual Function," Archive of General Psychiatry, vol. 57, No. 11, pp. 1012-1030 (2000).
IsHak et al, "Male Anorgasmia Treated with Oxytocin," Journal of Sexual Medicine, vol. 5, No. 4, pp. 1022-1024 (2008).
McMahon et al, "A Phase II Study to Investigate the Efficacy and Safety of the Selective Oxytocin Receptor Antagonist, IX-01, in Men with Lifelong Premature Ejaculation," The Journal of Urology, vol. 197, No. 4S, p. e1344 (2017).
Clément et al, "Inhibition of ejaculation by the non-peptide oxytocin receptor antagonist GSK557296: a multi-level site of action," British Journal of Pharmacology, vol. 169, pp. 1477-1485 (2013).
Shinghal et al, "Safety and Efficacy of Epelsiban in the Treatment of Men with Premature Ejaculation: A Randomized, Double-Blind, Placebo-Controlled, Fixed-Dose Study," The Journal of Sexual Medicine, vol. 10, pp. 2506-2517 (2013).

(Continued)

*Primary Examiner* — Timothy R Rozof
(74) *Attorney, Agent, or Firm* — Ice Miller LLP

(57) ABSTRACT

A condensed ring group azacyclobutyl triazole derivative, a preparation method therefor and use thereof in medicine are provided. In particular, a condensed ring group azacyclobutyl triazole derivative as represented by general formula (I), a preparation method therefor, a pharmaceutical composition containing the derivative, use thereof as a therapeutic agent, in particular as an oxytocin antagonist, and for treating or preventing a disease or a condition that is known or can exhibit a beneficial effect of inhibiting oxytocin are provided. The definition for each substituent in general formula (I) is the same as that in the description.

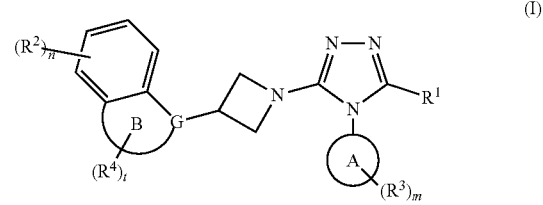

20 Claims, 1 Drawing Sheet

(56) References Cited

OTHER PUBLICATIONS

Borthwick, "Oral Oxytocin Antagonists," Journal of Medicinal Chemistry, vol. 53, pp. 6525-6538 (2010).
Barré et al, "Iron- and Cobalt-Catalyzed Arylation of Azetidines, Pyrrolidines, and Piperidines with Grignard Reagents," Organic Letters, vol. 16, No. 23, pp. 6160-6163 (2014).
Brown et al, "Triazole oxytocin antagonists: Identification of an aryloxyazetidine replacement for a biaryl substituent," Bioorganic & Medicinal Chemistry Letters, vol. 20, No. 2, pp. 516-520 (2010).
Romanov-Michailidis et al, "Enantioselective Halogenative Semi-Pinacol Rearrangement: Extension of Substrate Scope and Mechanistic Investigations," Chemistry—A European Journal, vol. 21, No. 14, pp. 5561-5583 (2015).
Steves et al, "Process Development of CuI/ABNO/NMI-Catalyzed Aerobic Alcohol Oxidation," Organic Process Research & Development, vol. 19, No. 11, pp. 1548-1553 (2015).
Zhu et al, "Design, Synthesis, X-ray Crystallographic Analysis, and Biological Evaluation of Thiazole Derivatives as Potent and Selective Inhibitors of Human Dihydroorotate Dehydrogenase," Journal of Medicinal Chemistry, vol. 58, No. 3, pp. 1123-1139 (2015).
Higashino et al, "Peripheral Arylation of Subporphyrazines," Chemistry—A European Journal, vol. 19, No. 31, pp. 10353-10359 (2013).
Hojczyk et al, "Trifluoromethoxylation of Arenes: Synthesis of ortho-Trifluoromethoxylated Aniline Derivatives by OCF3 Migration," Angewandte Chemie, International Edition, vol. 53, No. 52, pp. 14559-14563 (2014).
Reck et al, "Novel Substituted (Pyridin-3-yl)phenyloxazolidinones: Antibacterial Agents with Reduced Activity against Monoamine Oxidase A and Increased Solubility," Journal of Medicinal Chemistry, vol. 50, No. 20, pp. 4868-4881 (2007).
Karlsson et al, "Development of a Large-Scale Route to an MCH1 Receptor Antagonist: Investigation of a Staudinger Ketene-Imine Cycloaddition in Batch and Flow Mode," Organic Process Research & Development, vol. 19, No. 12, pp. 2067-2074 (2015).
Gotor-Fernández et al, "Chemoenzymatic preparation of optically active secondary amines: a new efficient route to enantiomerically pure indolines," Tetrahedron: Asymmetry, vol. 17, No. 17, pp. 2558-2564 (2006).
Renko et al, "Rapid synthesis of 4-arylchromenes from ortho-substituted alkynols: A versatile access to restricted isocombretastatin A-4 analogues as antitumor agents," European Journal of Medicinal Chemistry, vol. 90, pp. 834-844 (2015).
Parmenon et al, "4,4-Dimethyl-1,2,3,4-tetrahydroquinoline-based PPARalpha/gamma agonists. Part I: Synthesis and pharmacological evaluation," Bioorganic and Medicinal Chemistry Letters, vol. 18, No. 5, pp. 1617-1622 (2008).
Int'l Search Report dated Mar. 9, 2018 in Int'l Application No. PCT/CN2017/117421.

\* cited by examiner

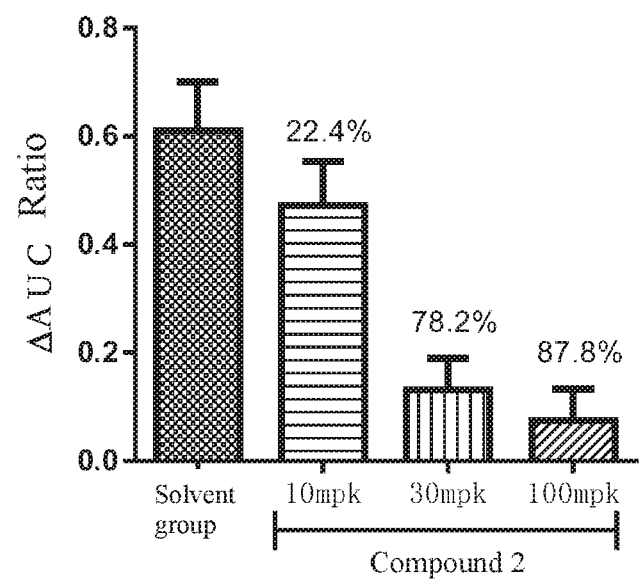

ns of the patient receptor antagon-ophase II clinical trials.
CONDENSED RING GROUP AZACYCLOBUTYL TRIAZOLE DERIVATIVE, PREPARATION METHOD THEREFOR AND USE THEREOF IN MEDICINE

CROSS-REFERENCE TO RELATED APPLICATION

This application is a Section 371 of International Application No. PCT/CN2017/117421, filed Dec. 20, 2017, which was published in the Chinese language on Jun. 28, 2018, under International Publication No. WO 2018/113694 A1, which claims priority under 35 U.S.C. § 119(b) to Chinese Application No. 201611191169.5, filed Dec. 21, 2016, the disclosures of which are incorporated herein by reference in their entirety.

FIELD OF THE INVENTION

The present invention belongs to the field of medicine, and relates to a novel condensed ring azacyclobutyl triazole derivative, a method for preparing the same, a pharmaceutical composition comprising the same, a use thereof as a therapeutic agent, in particular as an oxytocin antagonist, and a use thereof in the preparation of medicaments for the treatment or prevention of diseases or conditions for which inhibition of oxytocin is known, or can be shown, to produce a beneficial effect.

BACKGROUND OF THE INVENTION

Oxytocin (OT) is a cyclic nonapeptide that is normally synthesized by the hypothalamic paraventricular nucleus and released via the posterior pituitary. OT has a wide range of physiological functions, including social connections, sexual reproduction, labour and the like. OT exerts physiological effects by binding to oxytocin receptors (OTRs).

In recent years, strong evidence has been accumulated, indicating that oxytocin hormone plays a major role in inducing labour of mammals, especially humans. By "down-regulating" oxytocin, it is expected to block the direct (contraction) and indirect (increase in prostaglandin synthesis) effects of oxytocin on the uterus. Oxytocin regulators (such as blockers or antagonists) may be effective in treating miscarriage. Studies have also shown that premature patients have a higher oxytocin sensitivity and oxytocin receptor density compared with women of the same gestational age. Therefore, the application of oxytocin receptor antagonist to block the action of oxytocin and its receptors is an important way to prevent premature birth. During the test-tube baby embryo transfer, some patients have an increased uterine contraction, which is inversely related to the implantation success rate of the embryo (Lan et al., Reprod Biomed Online. 25(3):254-60, 2012). Therefore, oxytocin regulators can also be used to improve the pregnancy rate of patients receiving test-tube baby embryo transfer, especially patients that have suffered from several unsuccessful transfers. Another condition associated with oxytocin is dysmenorrhea, which is characterized by pain and discomfort during menstruation. Oxytocin plays a role in dysmenorrhea due to its activity as a uterine vasoconstrictor (Akerlund et al., Ann. NY Acad. Sci. 734: 47-56, 1994). Oxytocin antagonists have a therapeutic efficacy on this condition.

It is well documented that the levels of circulating oxytocin increase during sexual stimulation and arousal, and peak during orgasm in both men and women. As detailed in Gimpl and Fahrenholz (Physiological Reviews 81(2): 629-683, 2001), oxytocin has been found to be one of the most potent agents to induce penile erection in rats, rabbits and monkeys. In addition, central administration of oxytocin is claimed to reduce the latency to achieve ejaculation and to shorten the post-ejaculatory interval. Likewise, Meston et al. (Arch. Gen. Psychiatry, 57(11): 1012-30, 2000) states that in male animals, oxytocin facilitates penile erections when injected into specific areas of the brain (i.e., periventricular nucleus of the hypothalamus) and shortens the ejaculation latency and postejaculation interval when injected either centrally or peripherally. Oxytocin has also been successfully used to treat a patient with ahedonia. Inhalation of oxytocin through the nasal cavity can effectively restore ejaculation in patients who have previously failed to ejaculate during sexual intercourse (Ishak et al., J. Sex Med., 5(4):1022-4, 2007). Antagonists (or blockers) of oxytocin receptors have been shown to prolong the ejaculation latency of patients with prospermia in clinical trials. A selective oxytocin receptor antagonist IX-01 in the phase II clinical trials, when being administered orally (400 mg or 800 mg) to a patient with prospermia, can significantly prolong the vaginal ejaculation latency of the patient and improve the patient's self-perception (McMahon, et. al., J. Urol., 197(4S):e1344, 2017). Documents also report that in the ejaculation model of rats, an oxytocin receptor antagonist with poor brain permeability (GSK557296) can effectively inhibit the ejaculation behavior of rats only when being administered at specific central sites (intraventricular and intrathecal injection) (Clement et al., Br. J. Pharmacol., 169:1477-85, 2013). GSK557296 did not show corresponding efficacy after oral administration in the phase II clinical trials (Shinghal et. al., J. Sex Med., 10:2506-17, 2013). Therefore, the discovery of oxytocin receptor antagonists with good brain permeability is the key to the development of drugs for the treatment of ejaculation dysfunction such as prospermia.

The structure of oxytocin receptor is very similar to that of vasopressin receptors (including V1a receptor, V1b receptor, V2 receptor). V1a receptor and V2 receptor are mainly expressed in the periphery, which regulate blood pressure and kidney function, respectively. V1b receptor is mainly expressed in the brain and pituitary gland, and can control the release of adrenocorticotropic hormone and β-endorphin. Therefore, for safety reasons, highly selective OTR agonists are key issues that must be considered in future development (Alan D. Borthwick. J. Med. Chem. 2010, 53, 6525-6538).

A series of patent applications of OTR antagonists are currently disclosed, including WO2005028452, WO2005082866, WO2006077496, WO2006092731, WO2006100588 and WO2006100557. However, highly selective OTR antagonists are still the focus of development. The inventor designs a compound having a structure of formula (I) by continuous efforts, and finds that a compound having such a structure has a highly selective inhibition effect on OTR, good absorption and good brain permeability, and can effectively block the downstream function of the oxytocin receptor mediated by oxytocin.

SUMMARY OF THE INVENTION

An object of the present invention is to provide a compound of formula (I),

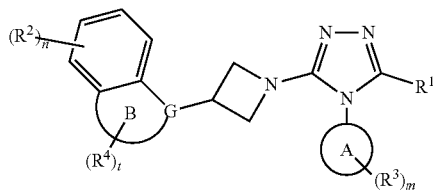

or a tautomer, mesomer, racemate, enantiomer, diastereomer thereof, or a mixture thereof, or a pharmaceutically acceptable salt thereof,
wherein:
G is selected from the group consisting of C, CH and N;
ring A is aryl or heteroaryl;
ring B is selected from the group consisting of cycloalkyl, heterocyclyl, aryl and heteroaryl;
$R^1$ is alkyl, wherein the alkyl is optionally substituted by one or more substituents selected from the group consisting of alkyl, alkoxy, halogen, haloalkyl, haloalkoxy, hydroxy, hydroxyalkyl, cyano, amino, nitro, cycloalkyl, heterocyclyl, heterocyclyloxy, $NHS(O)_sR^5$, $NHC(O)OR^5$, aryl and heteroaryl;
each $R^2$ is identical or different and each is independently selected from the group consisting of hydrogen, halogen, alkyl, alkoxy, haloalkyl, oxo, hydroxy, hydroxyalkyl, cyano, amino, nitro, cycloalkyl, heterocyclyl and $—C(O)OR^5$;
each $R^3$ is identical or different and each is independently selected from the group consisting of hydrogen, halogen, alkyl, alkoxy, haloalkyl, hydroxy, hydroxyalkyl, cyano, amino, nitro, cycloalkyl and heterocyclyl;
each $R^4$ is identical or different and each is independently selected from the group consisting of hydrogen, halogen, alkyl, alkoxy, haloalkyl, oxo, hydroxy, hydroxyalkyl, cyano, amino, nitro, cycloalkyl, heterocyclyl and $—C(O)OR^5$;
$R^5$ is selected from the group consisting of hydrogen, alkyl, haloalkyl, hydroxyalkyl, cycloalkyl, heterocyclyl, aryl and heteroaryl;
s is 0, 1 or 2;
n is 0, 1, 2, 3 or 4;
M is 0, 1, 2, 3 or 4; and
t is 0, 1, 2 or 3.

In a preferred embodiment of the present invention, the compound of formula (I) is a compound of formula (II):

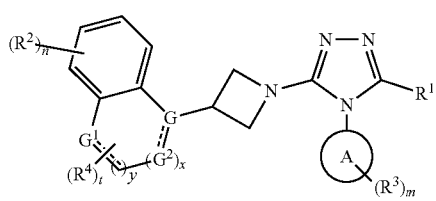

or a tautomer, mesomer, racemate, enantiomer, diastereomer thereof, or a mixture thereof, or a pharmaceutically acceptable salt thereof,
wherein:
═══ is a single bond or a double bond;
G is selected from the group consisting of C, CH and N;
$G^1$ is selected from the group consisting of N, NH, C, CH, $CH_2$, O and S;
$G^2$ is selected from the group consisting of C, CH, $CH_2$, N and NH;

x is 0 or 1;
y is 0 or 1; and
ring A, $R^1$-$R^4$, n, m and t are as defined in formula (I).

In a preferred embodiment of the present invention, the compound of formula (I) is a compound of formula (III):

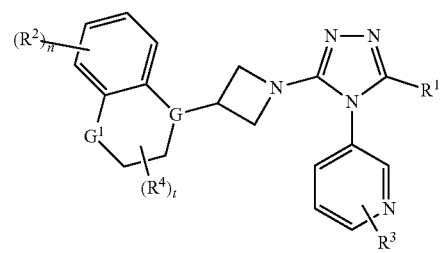

wherein:
G is selected from the group consisting of C, CH and N;
$G^1$ is selected from the group consisting of N, NH, C, CH, $CH_2$ and O;
$R^1$-$R^4$, n and t are as defined in formula (I).

In a preferred embodiment of the present invention, the compound of formula (I) is a compound of formula (IV):

(IV)

(structure shown)

or a tautomer, mesomer, racemate, enantiomer, diastereomer thereof, or a mixture thereof, or a pharmaceutically acceptable salt thereof,
wherein:
═══ is a single bond or a double bond;
G is selected from the group consisting of C, CH and N;
$G^1$ is selected from the group consisting of N, NH, C, CH, $CH_2$, O and S;
$G^2$ is selected from the group consisting of C, CH, $CH_2$, N and NH;
$R^1$-$R^4$, n and t are as defined in formula (I).

In a preferred embodiment of the present invention, provided is the compound of formula (I), wherein the ring A is pyridyl or benzodioxole; and preferably

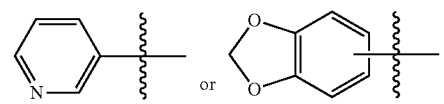

In a preferred embodiment of the present invention, provided is the compound of formula (I), wherein the ring B is pyrrolyl, furyl, thienyl, imidazolyl, pyrazolyl, oxazolyl, phenyl, pyridyl, pyranyl, pyrrolidinyl, piperidinyl, piperazinyl, morpholinyl, morpholin-3-one, tetrahydropyranyl, dihydropyranyl, tetrahydropyridyl, dihydropyrrolyl, dihydro-1,4-oxazinyl or 2H-1,4-oxazin-3-one.

In a preferred embodiment of the present invention, provided is the compound of formula (I), wherein

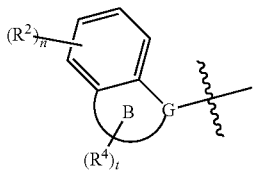

is selected from the group consisting of:

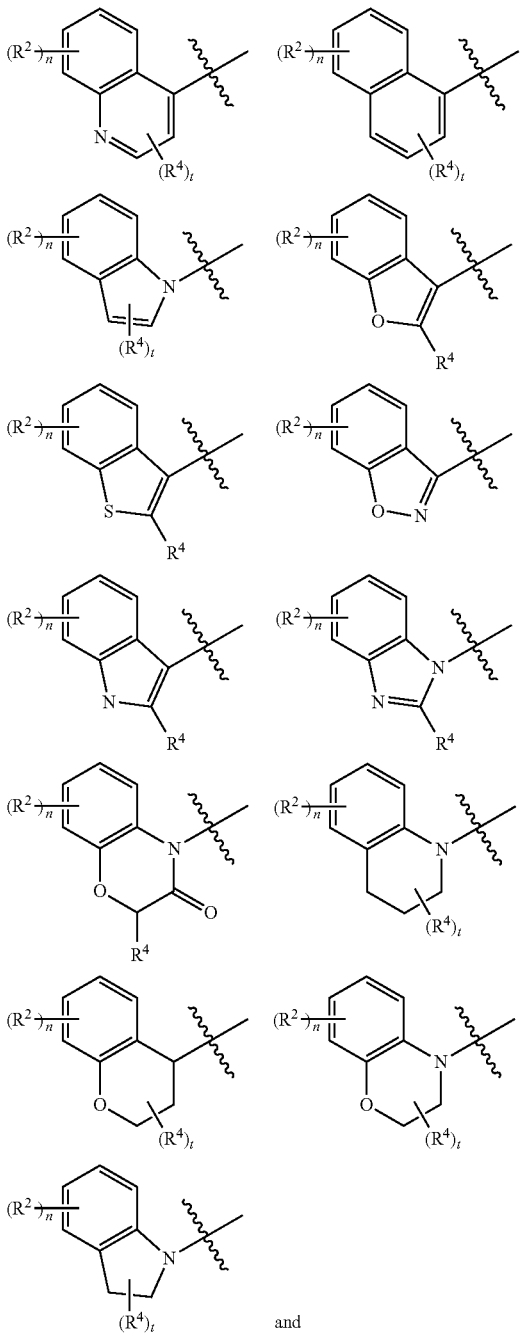

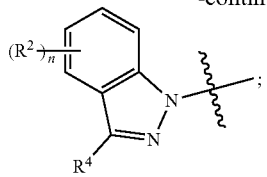

wherein:

R², R⁴, n and t are as defined in formula (I).

In a preferred embodiment of the present invention, provided is the compound of formula (I), wherein R¹ is alkyl, wherein the alkyl is optionally substituted by one or more substituents selected from the group consisting of alkoxy, halogen, haloalkyl, haloalkoxy, hydroxy, NHS(O)$_s$R⁵ and NHC(O)OR⁵; R⁵ is alkyl; and s is 0, 1 or 2.

In a preferred embodiment of the present invention, provided is the compound of formula (I), wherein each R² is identical or different and each is independently selected from the group consisting of hydrogen, halogen, alkyl and haloalkyl.

In a preferred embodiment of the present invention, provided is the compound of formula (I), wherein R³ is alkoxy.

In a preferred embodiment of the present invention, provided is the compound of formula (I), wherein each R⁴ is identical or different and each is independently selected from the group consisting of hydrogen, halogen, alkyl, haloalkyl, cyano, oxo and —C(O)OR⁵; and R⁵ is alkyl.

In a preferred embodiment of the present invention, provided is the compound of formula (I), wherein n is 1 or 2; and m is 0 or 1.

The compound of the present invention includes all conformational isomers thereof, e.g., cis-isomers and trans-isomers; and all optical isomers and stereoisomers as well as mixtures thereof. The compound of the present invention has asymmetric centers, and thus there are different enantiomeric and diastereomeric isomers. The present invention relates to a use of the compound of the present invention, and all pharmaceutical compositions applying or comprising the same, and a therapeutic method thereof. The present invention relates to a use of all such isomers and mixtures thereof.

Typical compounds of the present invention include, but are not limited to the following:

| Example No. | Structure and name of the compound |
|---|---|
| 1 | 7-Fluoro-4-(1-(5-(methoxymethyl)-4-(6-methoxypyridin-3-yl)-4H-1,2,4-triazol-3-yl)azetidin-3-yl)quinoline 1 |

| Example No. | Structure and name of the compound |
|---|---|
| 2 | 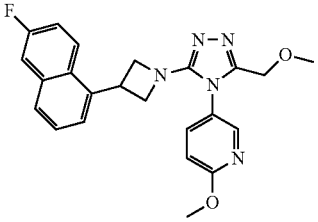 [SMILES: COCc1nnc(N2CC(c3cccc4cc(F)ccc34)C2)n1-c1ccc(OC)nc1]<br>5-(3-(3-(6-Fluoronaphthaen-1-yl)azetidin-1-yl)-5-(methoxymethyl)-4H-1,2,4-triazol-4-yl)-2-methoxypyridine 2 |
| 3 | 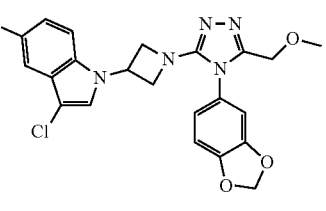<br>1-(1-(4-(Benzo[d][1,3]dioxolan-5-yl)-5-(methoxymethyl)-4H-1,2,4-triazol-3-yl)azetidin-3-yl)-3-chloro-5-fluoro-1H-indole 3 |
| 4 | 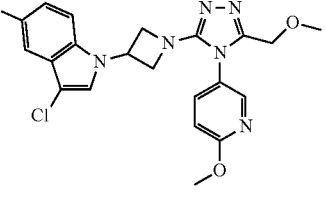<br>3-Chloro-1-(1-(5-(ethoxymethyl)-4-(6-methoxypyridin-3-yl)-4H-1,2,4-triazol-3-yl)azetidin-3-yl)-5-fluoro-1H-indole 4 |
| 5 | 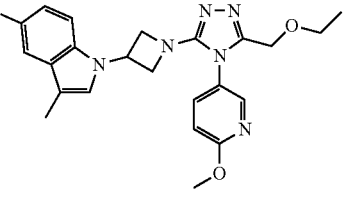<br>1-(1-(5-(Ethoxymethyl)-4-(6-methoxypyridin-3-yl)-4H-1,2,4-triazol-3-yl)azetidin-3-yl)-5-fluoro-3-methyl-1H-indole 5 |
| 6 | 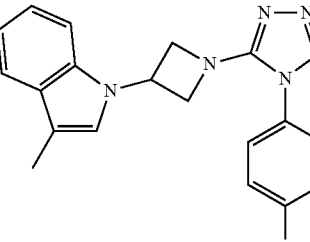<br>5-Fluoro-1-(1-(4-(6-methoxypyridin-3-yl)-5-methyl-4H-1,2,4-triazol-3-yl)azetidin-3-yl)-3-methyl-1H-indole 6 |
| 7 | 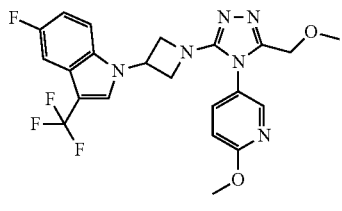 [SMILES: COCc1nnc(N2CC(n3cc(C(F)(F)F)c4cc(F)ccc43)C2)n1-c1ccc(OC)nc1]<br>5-Fluoro-1-(1-(5-(methoxymethyl)-4-(6-methoxypyridin-3-yl)-4H-1,2,4-triazol-3-yl)azetidin-3-yl)-3-(trifluoromethyl)-1H-indole 7 |
| 8 | 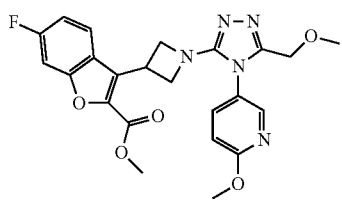 [SMILES: COCc1nnc(N2CC(c3c(C(=O)OC)oc4cc(F)ccc34)C2)n1-c1ccc(OC)nc1]<br>Methyl 6-fluoro-3-(1-(5-(methoxymethyl)-4-(6-methoxypyridin-3-yl)-4H-1,2,4-triazol-3-yl)azetidin-3-yl)benzofuran-2-carboxylate 8 |
| 9 | 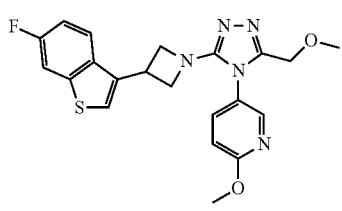<br>5-(3-(3-(6-Fluorobenzo[b]thiophen-3-yl)azetidin-1-yl)-5-(methoxymethyl)-4H-1,2,4-triazol-4-yl)-2-methoxypyridine 9 |
| 10 | 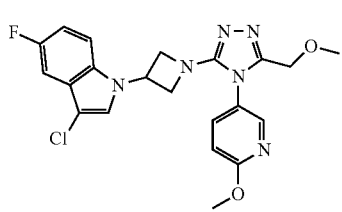 [SMILES: COCc1nnc(N2CC(n3cc(Cl)c4cc(F)ccc43)C2)n1-c1ccc(OC)nc1]<br>3-Chloro-5-fluoro-1-(1-(5-(methoxymethyl)-4-(6-methoxypyridin-3-yl)-4H-1,2,4-triazol-3-yl)azetidin-3-yl)-1H-indole 10 |
| 11 | 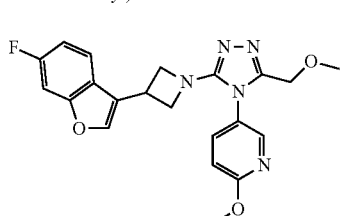<br>5-(3-(3-(6-Fluorobenzofuran-3-yl)azetidin-1-yl)-5-(methoxymethyl)-4H-1,2,4-triazol-4-yl)-2-methoxypyridine 11 |

| Example No. | Structure and name of the compound |
|---|---|
| 12 | 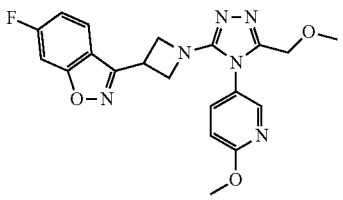 [SMILES: COCc1nnc(N2CC(c3noc4cc(F)ccc34)C2)n1-c1ccc(OC)nc1]<br>6-Fluoro-3-(1-(5-(methoxymethyl)-4-(6-methoxypyridin-3-yl)-4H-1,2,4-triazol-3-yl)azetidin-3-yl)benzo[d]isoxazole 12 |
| 13 | 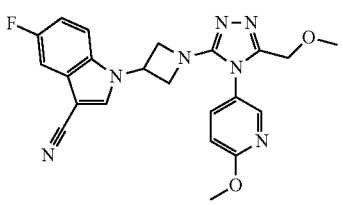 [SMILES: COCc1nnc(N2CC(n3cc(C#N)c4cc(F)ccc43)C2)n1-c1ccc(OC)nc1]<br>5-Fluoro-1-(1-(5-(methoxymethyl)-4-(6-methoxypyridin-3-yl)-4H-1,2,4-triazol-3-yl)azetidin-3-yl)-1H-indole-3-carbonitrile 13 |
| 14 | 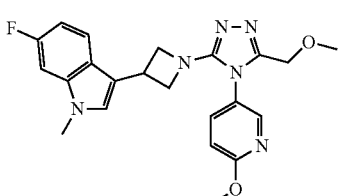<br>6-Fluoro-3-(1-(5-(methoxymethyl)-4-(6-methoxypyridin-3-yl)-4H-1,2,4-triazol-3-yl)azetidin-3-yl)-1-methyl-1H-indole 14 |
| 15 | 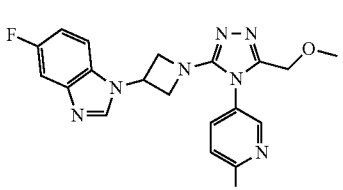<br>5-Fluoro-1-(1-(5-(methoxymethyl)-4-(6-methoxypyridin-3-yl)-4H-1,2,4-triazol-3-yl)azetidin-3-yl)-1H-benzo[d]imidazole 15 |
| 16 | 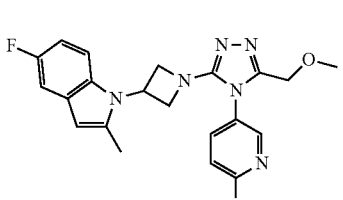<br>5-Fluoro-1-(1-(5-(methoxymethyl)-4-(6-methoxypyridin-3-yl)-4H-1,2,4-triazol-3-yl)azetidin-3-yl)-2-methyl-1H-indole 16 |
| 17 | 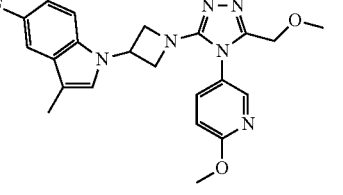<br>5-Fluoro-1-(1-(5-(methoxymethyl)-4-(6-methoxypyridin-3-yl)-4H-1,2,4-triazol-3-yl)azetidin-3-yl)-3-methyl-1H-indole 17 |
| 18 | 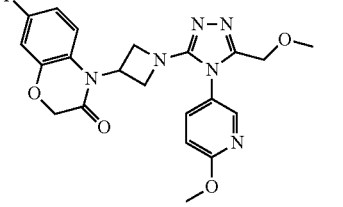<br>7-Fluoro-4-(1-(5-(methoxymethyl)-4-(6-methoxypyridin-3-yl)-4H-1,2,4-triazol-3-yl)azetidin-3-yl)-2H-benzo[b][1,4]oxazin-3(4H)-one 18 |
| 19 | 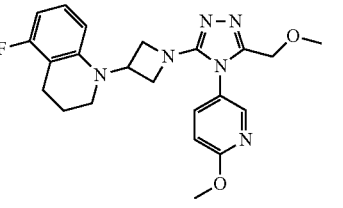<br>5-Fluoro-1-(1-(5-(methoxymethyl)-4-(6-methoxypyridin-3-yl)-4H-1,2,4-triazol-3-yl)azetidin-3-yl)-1,2,3,4-tetrahydroquinoline 19 |
| 20 | 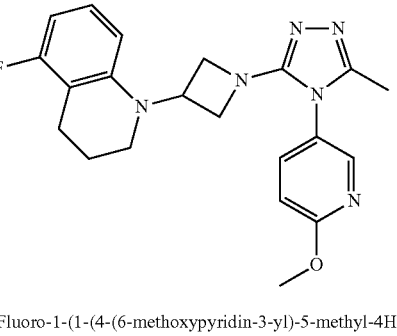<br>5-Fluoro-1-(1-(4-(6-methoxypyridin-3-yl)-5-methyl-4H-1,2,4-triazol-3-yl)azetidin-3-yl)-1,2,3,4-tetrahydroquinoline 20 |
| 21 | 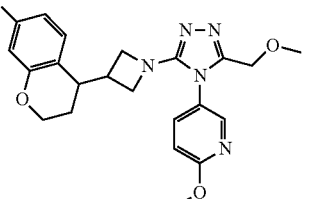<br>5-(3-(3-(7-Fluorobenzodihydropyran-4-yl)azetidin-1-yl)-5-(methoxymethyl)-4H-1,2,4-triazol-4-yl)-2-methoxypyridine 21 |

| Example No. | Structure and name of the compound |
|---|---|
| 22 | 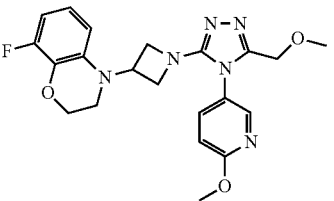 [SMILES: COCc1nnc(N2CC(N3CCCc4c(F)cccc43)C2)n1-c1ccc(OC)nc1]<br>8-Fluoro-4-(1-(5-(methoxymethyl)-4-(6-methoxypyridin-3-yl)-4H-1,2,4-triazol-3-yl)azetidin-3-yl)-3,4-dihydro-2H-benzo[b][1,4]oxazine 22 |
| 23 | 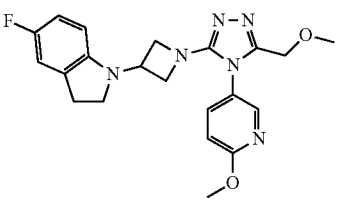 [SMILES: COCc1nnc(N2CC(N3CCc4cc(F)ccc43)C2)n1-c1ccc(OC)nc1]<br>5-Fluoro-1-(1-(5-(methoxymethyl)-4-(6-methoxypyridin-3-yl)-4H-1,2,4-triazol-3-yl)azetidin-3-yl)indoline 23 |
| 24 | 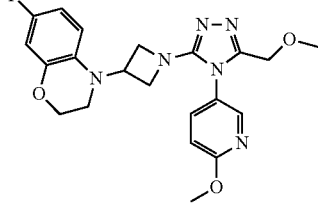<br>7-Fluoro-4-(1-(5-(methoxymethyl)-4-(6-methoxypyridin-3-yl)-4H-1,2,4-triazol-3-yl)azetidin-3-yl)-3,4-dihydro-2H-benzo[b][1,4]oxazine 24 |
| 25 | 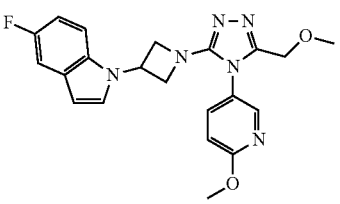<br>5-Fluoro-1-(1-(5-(methoxymethyl)-4-(6-methoxypyridin-3-yl)-4H-1,2,4-triazol-3-yl)azetidin-3-yl)-1H-indole 25 |
| 26 | 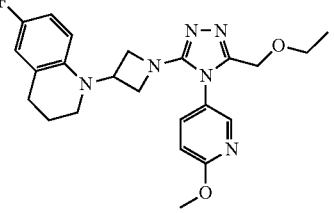<br>1-(1-(5-(Ethoxymethyl)-4-(6-methoxypyridin-3-yl)-4H-1,2,4-triazol-3-yl)azetidin-3-yl)-6-fluoro-1,2,3,4-tetrahydroquinoline 26 |
| 27 | 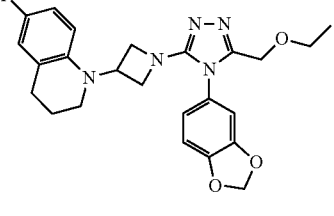<br>1-(1-(4-(Benzo[d][1,3]dioxolan-5-yl)-5-(ethoxymethyl)-4H-1,2,4-triazol-3-yl)azetidin-3-yl)-6-fluoro-1,2,3,4-tetrahydroquinoline 27 |
| 28 | 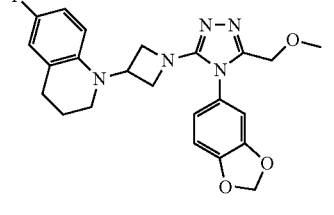<br>1-(1-(4-(Benzo[d][1,3]dioxolan-5-yl)-5-(methoxymethyl)-4H-1,2,4-triazol-3-yl)azetidin-3-yl)-6-fluoro-1,2,3,4-tetrahydroquinoline 28 |
| 29 | 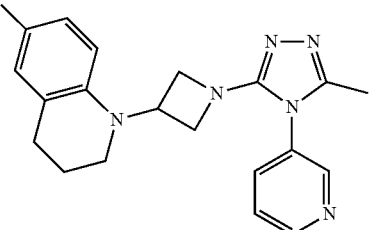<br>6-Fluoro-1-(1-(4-(6-methoxypyridin-3-yl)-5-methyl-4H-1,2,4-triazol-3-yl)azetidin-3-yl)-1,2,3,4-tetrahydroquinoline 29 |
| 30 | 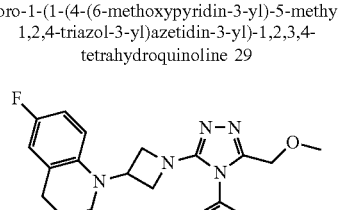<br>6-Fluoro-1-(1-(5-(methoxymethyl)-4-(6-methoxypyridin-3-yl)-4H-1,2,4-triazol-3-yl)azetidin-3-yl)-1,2,3,4-tetrahydroquinoline 30 |
| 31 | 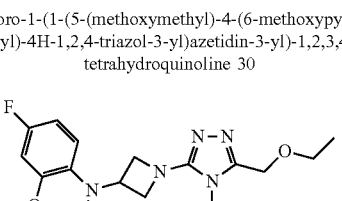 |

| Example No. | Structure and name of the compound |
|---|---|
| | 4-(1-(5-(Ethoxymethyl)-4-(6-methoxypyridin-3-yl)-4H-1,2,4-triazol-3-yl)azetidin-3-yl)-7-fluoro-3,4-dihydro-2H-benzo[b][1,4]oxazine 31 |
| 32 | 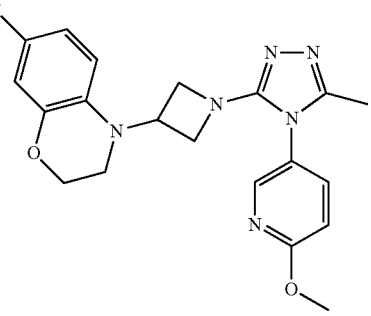<br>7-Fluoro-4-(1-(4-(6-methoxypyridin-3-yl)-5-methyl-4H-1,2,4-triazol-3-yl)azetidin-3-yl)-3,4-dihydro-2H-benzo[b][1,4]oxazine 32 |
| 33 | 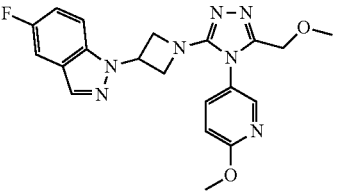 [SMILES: COCc1nnc(N2CC(n3ncc4cc(F)ccc43)C2)n1-c1ccc(OC)nc1]<br>5-Fluoro-1-(1-(5-(methoxymethyl)-4-(6-methoxypyridin-3-yl)-4H-1,2,4-triazol-3-yl)azetidin-3-yl)-1H-indazole 33 |
| 34 | 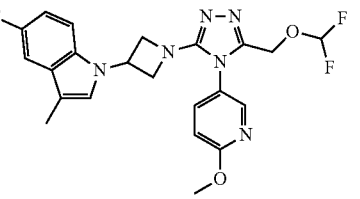<br>1-(1-(5-((Difluoromethoxy)methyl)-4-(6-methoxypyridin-3-yl)-4H-1,2,4-triazol-3-yl)azetidin-3-yl)-5-fluoro-3-methyl-1H-indole 34 |
| 35 | 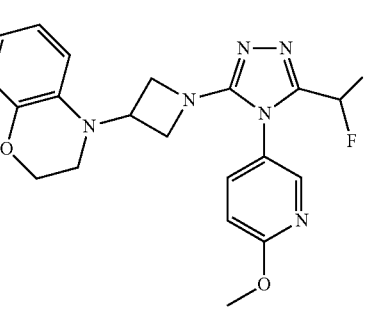<br>4-(1-(5-(Difluoromethyl)-4-(6-methoxypyridin-3-yl)-4H-1,2,4-triazol-3-yl)azetidin-3-yl)-7-fluoro-3,4-dihydro-2H-benzo[b][1,4]oxazine 35 |
| 36 | 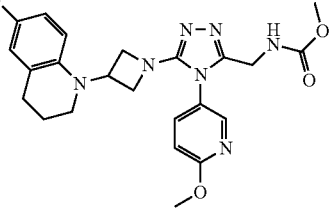<br>Methyl ((5-(3-(6-fluoro-3,4-dihydroquinolin-1(2H)-yl)azetidin-1-yl)-4-(6-methoxypyridin-3-yl)-4H-1,2,4-triazol-3-yl)methyl)carbamate 36 |
| 37 | <br>4-(1-(5-((Difluoromethoxy)methyl)-4-(6-methoxypyridin-3-yl)-4H-1,2,4-triazol-3-yl)azetidin-3-yl)-7-fluoro-3,4-dihydro-2H-benzo[b][1,4]oxazine 37 |
| 38 | <br>5-(3-((Difluoromethoxy)methyl)-5-(3-(6-fluoronaphthalen-1-yl)azetidin-1-yl)-4H-1,2,4-triazol-4-yl)-2-methoxypyridine 38 |
| 39 | 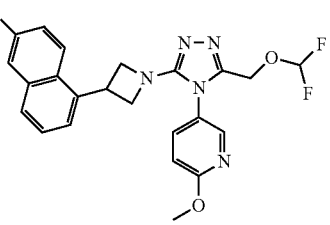<br>6-Fluoro-1-(1-(4-(6-methoxypyridin-3-yl)-5-(trifluoromethyl)-4H-1,2,4-triazol-3-yl)azetidin-3-yl)-1,2,3,4-tetrahydroquinoline 39 |
| 40 | 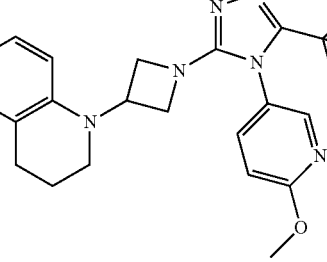 |

| Example No. | Structure and name of the compound |
|---|---|
| 41 | 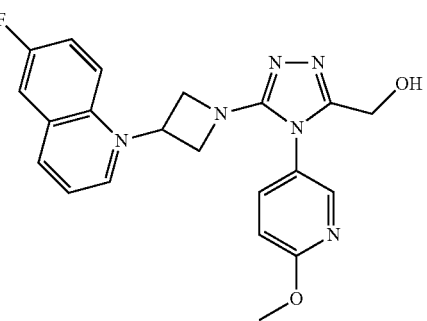<br>(5-(3-(6-Fluoronaphthalen-1-yl)azetidin-1-yl)-4-(6-methoxypyridin-3-yl)-4H-1,2,4-triazol-3-yl)methanol 2 |
| 42 | 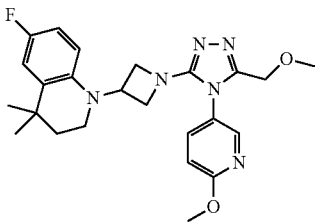<br>6-Fluoro-1-(1-(5-(methoxymethyl)-4-(6-methoxypyridin-3-yl)-4H-1,2,4-triazol-3-yl)azetidin-3-yl)-4,4-dimethyl-1,2,3,4-tetrahydroquinoline 42 |
| 43 | 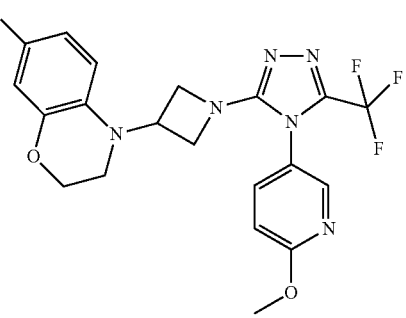<br>7-Fluoro-4-(1-(4-(6-methoxypyridin-3-yl)-5-(trifluoromethyl)-4H-1,2,4-triazol-3-yl)azetidin-3-yl)-3,4-dihydro-2H-benzo[b][1,4]oxazine 43 |

N-((5-(3-(6-Fluoro-3,4-dihydroquinolin-1(2H)-yl)azetidin-1-yl)-4-(6-methoxypyridin-3-yl)-4H-1,2,4-triazol-3-yl)methyl)methanesulfonamide 40 or a tautomer, mesomer, racemate, enantiomer, diastereomer thereof, or a mixture thereof, or a pharmaceutically acceptable salt thereof.

A preferred embodiment of the present invention relates to a compound of formula (I-A) which is an intermediate for synthesizing the compound of formula (I):

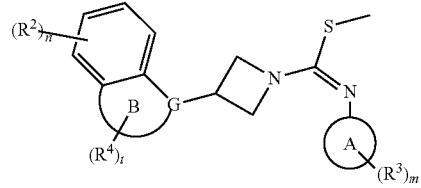

or a tautomer, mesomer, racemate, enantiomer, diastereomer thereof, or a mixture thereof, or a pharmaceutically acceptable salt thereof, wherein:

G is selected from the group consisting of C, CH and N; and ring A, ring B, $R^2$-$R^4$, n, m and t are as defined in formula (I).

The compounds of formula (I-A) include, but are not limited to the following:

| Example No. | Structure and name of the compound |
|---|---|
| 1g | F<br>Methyl (E)-3-(7-fluoroquinolin-4-yl)-N-(6-methoxypyridin-3-yl)azetidine-1-carbimidothioate 1g |
| 2f | 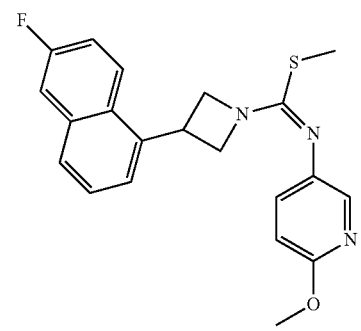 [SMILES: COc1ccc(/N=C(/SC)N2CC(c3cccc4cc(F)ccc34)C2)cn1]<br>Methyl (E)-3-(6-fluoronaphthalen-1-yl)-N-(6-methoxypyridin-3-yl)azetidine-1-carbimidothioate 2f |

-continued

| Example No. | Structure and name of the compound |
|---|---|
| 3i | Methyl (E)-N-benzo[d][1,3]dioxolan-5-yl-3-(3-chloro-5-fluoro-1H-indol-1-yl)azetidine-1-carbimidothioate 3i |
| 4b | Methyl (E)-3-(3-chloro-5-fluoro-1H-indol-1-yl)-N-(6-methoxypyridin-3-yl)azetidine-1-carbimidothioate 4b |
| 5f | Methyl (E)-3-(5-fluoro-3-methyl-1H-indol-1-yl)-N-(6-methoxypyridin-3-yl)azetidine-1-carbimidothioate 5f |
| 7d | Methyl (E)-3-(5-fluoro-3-(trifluoromethyl)-1H-indol-1-yl)-N-(6-methoxypyridin-3-yl)azetidine-1-carbimidothioate 7d |
| 8f | Methyl (E)-6-fluoro-3-(1-(((6-methoxypyridin-3-yl)imino)(methylthio)methyl)azetidin-3-yl)benzofuran-2-carboxylate 8f |
| 9f | Methyl (E)-3-(6-fluorobenzo[b]thiophen-3-yl)-N-(6-methoxypyridin-3-yl)azetidine-1-carbimidothioate 9f |
| 11i | Methyl (E)-3-(6-fluorobenzofuran-3-yl)-N-(6-methoxypyridin-3-yl)azetidine-1-carbimidothioate 11i |

-continued

| Example No. | Structure and name of the compound |
|---|---|
| 12e | Methyl (E)-3-(6-fluorobenzo[d]isoxazol-3-yl)-N-(6-methoxypyridin-3-yl)azetidine-1-carbimidothioate 12e |
| 13d | Methyl (E)-3-(3-cyano-5-fluoro-1H-indol-1-yl)-N-(6-methoxypyridin-3-yl)azetidine-1-carbimidothioate 13d |
| 14g | Methyl (E)-3-(6-fluoro-1-methyl-1H-indol-3-yl)-N-(6-methoxypyridin-3-yl)azetidine-1-carbimidothioate 14g |
| 15f | Methyl (E)-3-(5-fluoro-1H-benzo[d]imidazol-1-yl)-N-(6-methoxypyridin-3-yl)azetidine-1-carbimidothioate 15f |
| 16f | Methyl (E)-3-(5-fluoro-2-methyl-1H-indol-1-yl)-N-(6-methoxypyridin-3-yl)azetidine-1-carbimidothioate 16f |
| 18g | Methyl (E)-3-(7-fluoro-3-oxo-2H-benzo[b][1,4]oxazin-4(3H)-yl)-N-(6-methoxypyridin-3-yl)azetidine-1-carbimidothioate 18g |
| 19e | Methyl (E)-3-(5-fluoro-3,4-dihydroquinolin-1(2H)-yl)-N-(6-methoxypyridin-3-yl)azetidine-1-carbimidothioate 19e |

-continued

| Example No. | Structure and name of the compound |
|---|---|
| 21g | 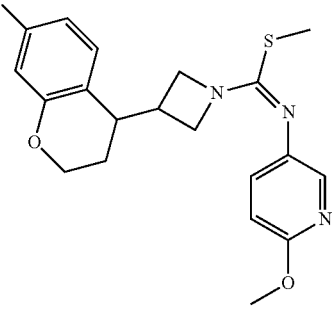<br>Methyl (E)-3-(7-fluorodihydrobenzopyran-4-yl)-N-(6-methoxypyridin-3-yl)azetidine-1-carbimidothioate 21g |
| 22f | 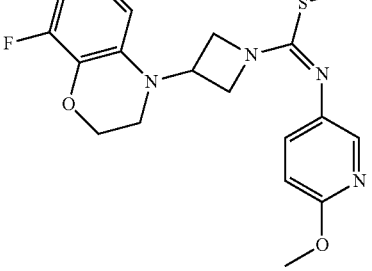<br>Methyl (E)-3-(8-fluoro-2H-benzo[b][1,4]oxazin-4(3H)-yl)-N-(6-methoxypyridin-3-yl)azetidine-1-carbimidothioate 22f |
| 23c | 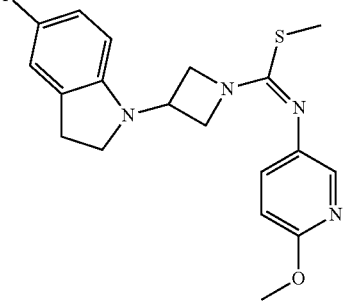<br>Methyl (E)-3-(5-fluoroindolin-1-yl)-N-(6-methoxypyridin-3-yl)azetidine-1-carbimidothioate 23c |
| 24f | 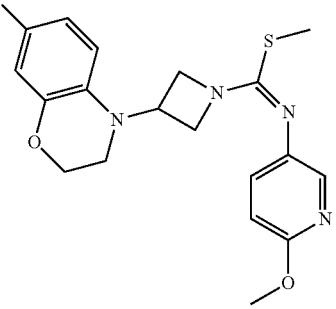<br>Methyl (E)-3-(7-fluoro-2H-benzo[b][1,4]oxazin-4(3H)-yl)-N-(6-methoxypyridin-3-yl)azetidine-1-carbimidothioate 24f |

-continued

| Example No. | Structure and name of the compound |
|---|---|
| 25a | 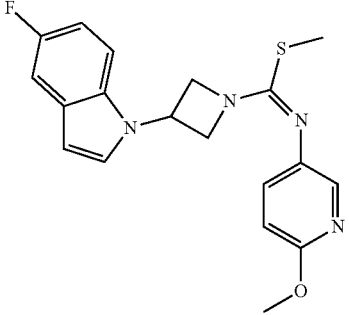 [SMILES: COc1ccc(/N=C(/SC)N2CC(n3ccc4cc(F)ccc43)C2)cn1]<br>Methyl (E)-3-(5-fluoro-1H-indol-1-yl)-N-(6-methoxypyridin-3-yl)azetidine-1-carbimidothioate 25a |
| 26a | 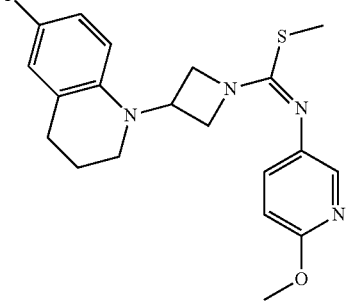<br>Methyl (E)-3-(6-fluoro-3,4-dihydroquinolin-1(2H)-yl)-N-(6-methoxypyridin-3-yl)azetidine-1-carbimidothioate 26a |
| 27a | 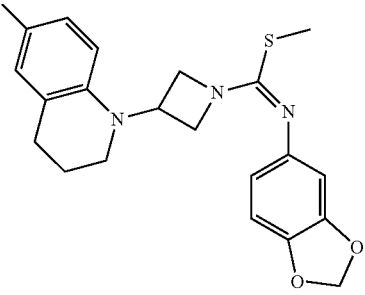<br>Methyl (E)-N-benzo[d][1,3]dioxolan-5-yl-3-(6-fluoro-3,4-dihydroquinolin-1(2H)-yl)azetidine-1-carbimidothioate 27a |
| 33a | 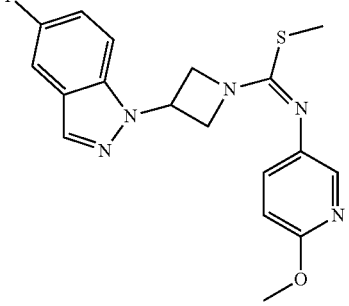<br> |

| Example No. | Structure and name of the compound |
|---|---|
| | Methyl (E)-3-(5-fluoro-1H-indazol-1-yl)-N-(6-methoxypyridin-3-yl)azetidine-1-carbimidothioate 33a |

In another aspect, the present invention relates to a method for preparing the compound of formula (I), comprising a step of:

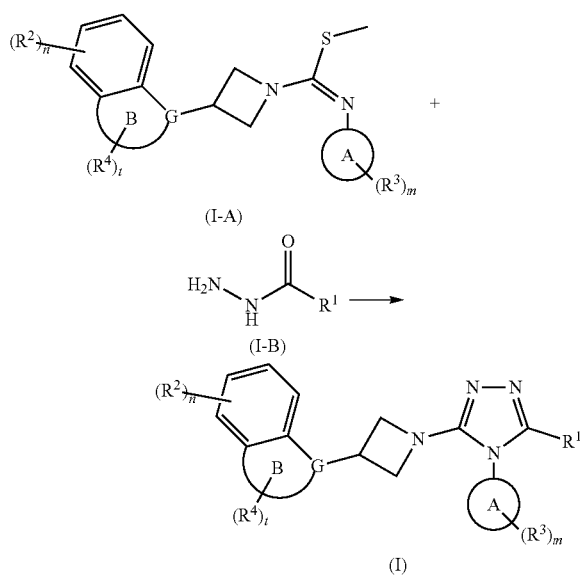

heating a compound of formula (I-A) and a compound of formula (I-B) or a hydrochloride salt thereof under an acidic condition to obtain the compound of formula (I), wherein:

ring A, ring B, $R^1$-$R^4$, G, n, m and t are as defined in formula (I).

In another aspect, the present invention relates to a method for preparing the compound of formula (II), comprising a step of:

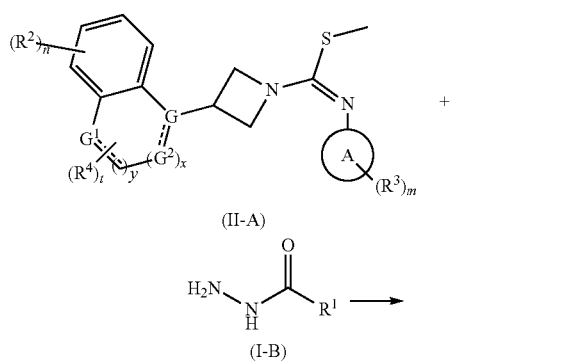

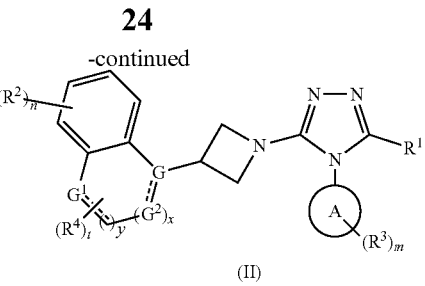

wherein:

⸗ is a single bond or a double bond;

G is selected from the group consisting of C, CH and N;

$G^1$ is selected from the group consisting of N, NH, C, CH, $CH_2$, O and S;

$G^2$ is selected from the group consisting of C, CH, $CH_2$, N and NH;

X is 0 or 1;

Y is 0 or 1; and ring A, $R^1$-$R^4$, n, m and t are as defined in formula (I).

In another aspect, the present invention relates to a method for preparing the compound of formula (III), comprising a step of:

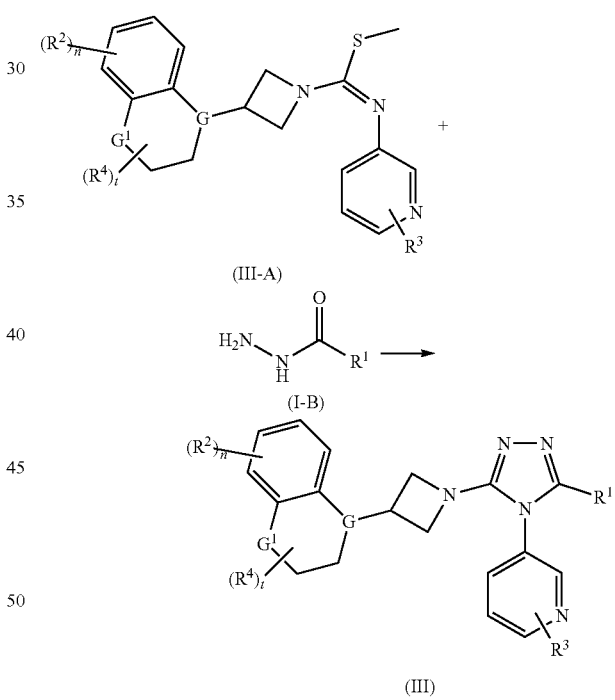

heating a compound of formula (III-A) and a compound of formula (I-B) or a hydrochloride salt thereof under an acidic condition to obtain the compound of formula (III), wherein:

G is selected from the group consisting of C, CH and N;

$G^1$ is selected from the group consisting of N, NH, C, CH, $CH_2$ and O;

$R^1$-$R^4$, n and t are as defined in formula (I).

In another aspect, the present invention relates to a method for preparing the compound of formula (IV), comprising a step of:

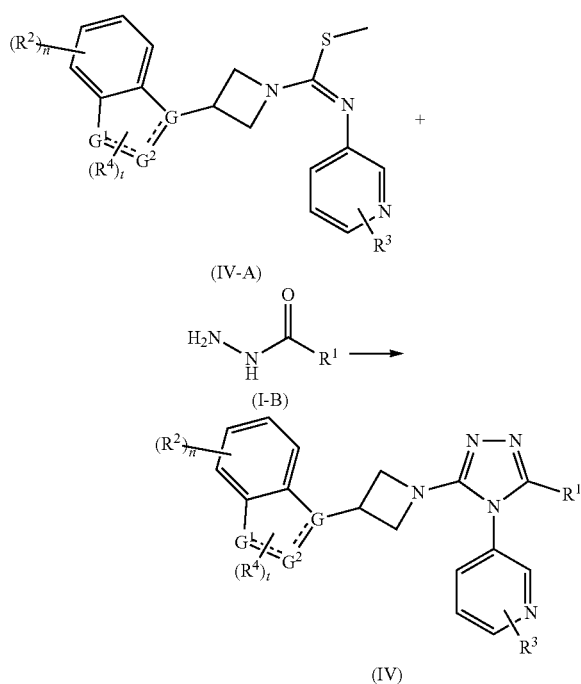

heating a compound of formula (IV-A) and a compound of formula (I-B) or a hydrochloride salt thereof under an acidic condition to obtain the compound of formula (IV), wherein:

≡≡≡ is a single bond or a double bond;

G is selected from the group consisting of C, CH and N;

$G^1$ is selected from the group consisting of N, NH, C, CH, $CH_2$, O and S;

$G^2$ is selected from the group consisting of C, CH, $CH_2$, N and NH;

$R^1$-$R^4$, n and t are as defined in formula (I).

In another aspect, the present invention relates to a pharmaceutical composition comprising a therapeutically effective amount of the compound of formula (I), or a tautomer, mesomer, racemate, enantiomer, diastereomer thereof, or a mixture thereof, or a pharmaceutically acceptable salt thereof, and one or more pharmaceutically acceptable carriers, diluents or excipients. The present invention also relates to a method for preparing the aforementioned composition, comprising a step of mixing the compound of formula (I), or a tautomer, mesomer, racemate, enantiomer, diastereomer thereof, or a mixture thereof, or a pharmaceutically acceptable salt thereof, with one or more pharmaceutically acceptable carriers, diluents or excipients.

The present invention further relates to a use of the compound of formula (I), or a tautomer, mesomer, racemate, enantiomer, diastereomer thereof, or a mixture thereof, or a pharmaceutically acceptable salt thereof, or the pharmaceutical composition comprising the same in the preparation of medicaments for the treatment or prevention of diseases or conditions for which inhibition of oxytocin is known, or can be shown, to produce a beneficial effect, wherein the disease or condition is preferably selected from the group consisting of sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhea, congestive heart failure, arterial hypertension, liver cirrhosis, nephrotic hypertension, ocular hypertension, obsessive and behavioral disorders and neuropsychiatric disorders, and more preferably selected from the group consisting of sexual dysfunction, sexual arousal disorder, orgasmic disorder, sexual pain disorder and premature ejaculation.

The present invention further relates to a use of the compound of formula (I), or a tautomer, mesomer, racemate, enantiomer, diastereomer thereof, or a mixture thereof, or a pharmaceutically acceptable salt thereof, or the pharmaceutical composition comprising the same in the preparation of medicaments for antagonizing oxytocin.

The present invention further relates to a method for the treatment or prevention of diseases or conditions for which inhibition of oxytocin is known, or can be shown, to produce a beneficial effect, which comprises a step of administering to a patient in need thereof a therapeutically effective amount of the compound of formula (I), or a tautomer, mesomer, racemate, enantiomer, diastereomer thereof, or the mixture thereof, or a pharmaceutically acceptable salt thereof, or the pharmaceutical composition comprising the same.

The present invention further relates to a method for the treatment or prevention of diseases selected from the group consisting of sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhea, congestive heart failure, arterial hypertension, liver cirrhosis, nephrotic hypertension, ocular hypertension, obsessive and behavioral disorders and neuropsychiatric disorders, and preferably selected from the group consisting of sexual dysfunction, sexual arousal disorder, orgasmic disorder, sexual pain disorder and premature ejaculation, which comprises a step of administering to a patient in need thereof a therapeutically effective amount of the compound of formula (I), or a tautomer, mesomer, racemate, enantiomer, diastereomer thereof, or a mixture thereof, or a pharmaceutically acceptable salt thereof, or the pharmaceutical composition comprising the same.

The present invention further relates to a method for antagonizing oxytocin, comprising a step of administering to a patient in need thereof a therapeutically effective amount of the compound of formula (I), or a tautomer, mesomer, racemate, enantiomer, diastereomer thereof, or a mixture thereof, or a pharmaceutically acceptable salt thereof, or the pharmaceutical composition comprising the same.

The present invention further relates to the compound of formula (I), or a tautomer, mesomer, racemate, enantiomer, diastereomer thereof, or a mixture thereof, or a pharmaceutically acceptable salt thereof, or the pharmaceutical composition comprising the same, for use as a medicament.

The present invention further relates to the compound of formula (I), or a tautomer, mesomer, racemate, enantiomer, diastereomer thereof, or a mixture thereof, or a pharmaceutically acceptable salt thereof, or the pharmaceutical composition comprising the same, for use as an oxytocin antagonist.

The present invention further relates to the compound of formula (I), or a tautomer, mesomer, racemate, enantiomer, diastereomer thereof, or a mixture thereof, or a pharmaceutically acceptable salt thereof, or the pharmaceutical composition comprising the same, for use in the treatment or prevention of diseases selected from the group consisting of sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhea, congestive heart failure, arterial hypertension, liver cirrhosis, nephrotic hypertension, ocular hypertension, obsessive and behavioral disorders and neuropsychiatric disorders, and preferably selected from the group consisting of sexual dysfunction, sexual arousal disorder, orgasmic disorder, sexual pain disorder and premature ejaculation.

The pharmaceutical composition containing the active ingredient may be in a form suitable for oral administration, for example, a tablet, a troche, a lozenge, an aqueous or oily suspension, a dispersible powder or granule, an emulsion, a hard or soft capsule, or a syrup or elixir. The oral compositions can be prepared according to any known method in the art for the preparation of pharmaceutical compositions. Such compositions may contain one or more ingredients selected from the group consisting of sweeteners, flavoring agents, colorants and preservatives, in order to provide a pleasing and palatable pharmaceutical preparation. A tablet contains the active ingredient in admixture with nontoxic pharmaceutically acceptable excipients suitable for the manufacture of tablets. An aqueous suspension contains the active ingredient in admixture with excipients suitable for the manufacture of an aqueous suspension. Such excipient is a suspending agent.

An oil suspension can be formulated by suspending the active ingredient in a vegetable oil. The oil suspension may contain a thickener. The aforementioned sweeteners and flavoring agents may be added to provide a palatable preparation. These compositions can be preserved by adding an antioxidant, such as butylated hydroxyanisole or alpha-tocopherol.

The active ingredient in admixture with the dispersants or wetting agents, suspending agent or one or more preservatives can be provided as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, may also be added. These compositions can be preserved by adding an antioxidant, such as ascorbic acid.

The pharmaceutical composition of the present invention may also be in the form of an oil-in-water emulsion. The oil phase may be a vegetable oil such as olive oil or peanut oil, or mineral oil such as liquid paraffin, or a mixture thereof. The emulsion may also contain sweeteners, flavoring agents, preservatives and antioxidants. Such preparations may also contain moderator, preservatives, colorants, and antioxidants.

The pharmaceutical composition of the present invention may be in the form of a sterile injectable aqueous solution. The sterile injectable formulation may be a sterile injectable oil-in-water micro-emulsion in which the active ingredient is dissolved in the oil phase.

The pharmaceutical composition of the present invention may be in the form of a sterile injectable aqueous or oily suspension for intramuscular and subcutaneous administration. Such a suspension can be formulated with suitable dispersants or wetting agents and suspending agents as described above according to the known techniques. The sterile injectable preparation may also be a sterile injectable solution or suspension prepared in a nontoxic parenterally acceptable diluent or solvent. Sterile fixed oils may easily be used as a solvent or suspending medium.

The compound of the present invention can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug. It is well known to those skilled in the art that the dosage of a drug depends on a variety of factors including but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of the pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, and preferably cyclopropyl, cyclobutyl, cyclopentyl and cyclohexyl. Polycyclic cycloalkyl includes a cycloalkyl having a spiro ring, fused ring or bridged ring.

The term "spiro cycloalkyl" refers to a 5 to 20 membered polycyclic group with rings connected through one shared carbon atom (called a spiro atom), wherein the rings can contain one or more double bonds, but none of the rings has a completely conjugated π-electron system. The spiro cycloalkyl is preferably 6 to 14 membered spiro cycloalkyl, and more preferably 7 to 10 membered spiro cycloalkyl. According to the number of the spiro atoms shared between the rings, the spiro cycloalkyl can be divided into monospiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

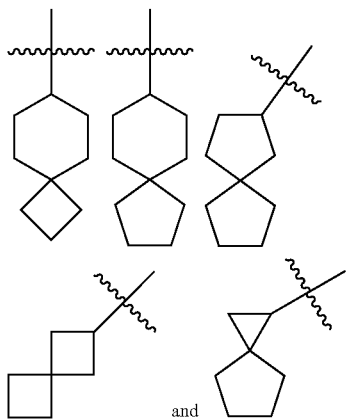

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated π-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and the fused cycloalkyl is preferably bicyclic or tricyclic fused cycloalkyl, and more preferably 5-membered/5-membered, or 5-membered/6-membered bicyclic fused cycloalkyl. Non-limiting examples of fused cycloalkyl include:

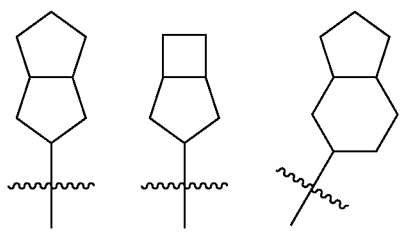

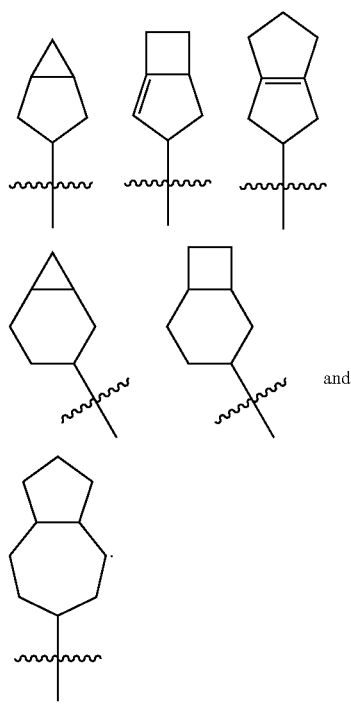

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and the bridged cycloalkyl is preferably bicyclic, tricyclic or tetracyclic bridged cycloalkyl, and more preferably bicyclic or tricyclic bridged cycloalkyl. Non-limiting examples of bridged cycloalkyls include:

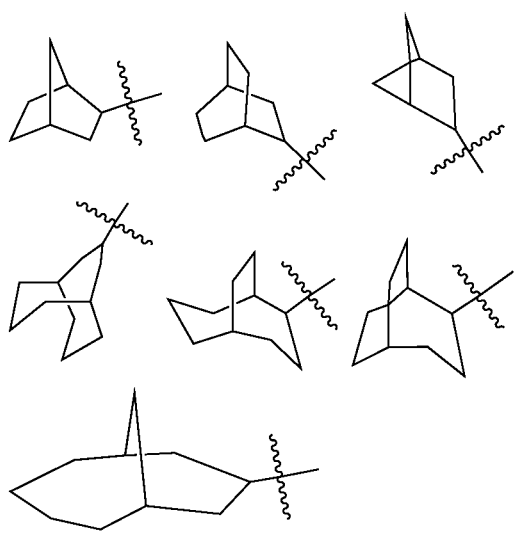

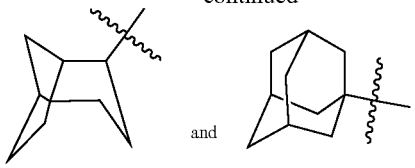

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio and —C(O)OR$^5$.

The term "heterocyclyl" refers to a 3 to 20 membered saturated or partially unsaturated monocyclic or polycyclic hydrocarbon group, wherein one or more ring atoms are heteroatoms selected from the group consisting of N, O and S(O)$_q$ (wherein q is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, the heterocyclyl has 3 to 10 ring atoms, and most preferably 3 to 6 ring atoms. Non-limiting examples of monocyclic heterocyclyl include oxacyclobutyl, azacyclobutyl, tetrahydrofuranyl, tetrahydropyranyl, pyrrolyl, piperidinyl, piperazinyl, morpholinyl, thiomorpholinyl, homopiperazinyl and the like, and preferably azacyclobutyl, oxacyclobutyl, pyrrolyl and piperidinyl. Polycyclic heterocyclyl includes a heterocyclyl having a spiro ring, fused ring or bridged ring.

The term "spiro heterocyclyl" refers to a 5 to 20 membered polycyclic heterocyclyl group with rings connected through one shared atom (called a spiro atom), wherein one or more ring atoms are heteroatoms selected from the group consisting of N, O and S(O)$_q$ (wherein q is an integer of 0 to 2), with the remaining ring atoms being carbon atoms, where the rings can contain one or more double bonds, but none of the rings has a completely conjugated π-electron system. The spiro heterocyclyl is preferably 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and the spiro heterocyclyl is preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

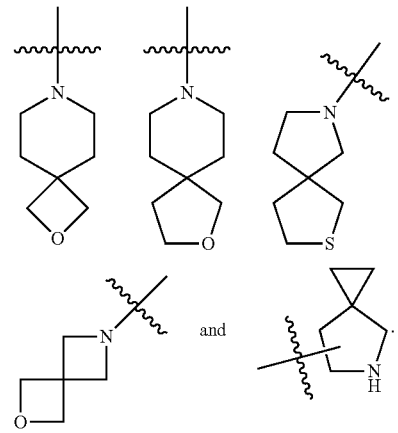

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and S(O)$_q$ (wherein q is an integer of 0 to 2), with the remaining ring atoms being carbon atoms. The fused heterocyclyl is preferably 6 to 14 membered fused heterocyclyl, and more preferably 7 to 10 membered fused heterocyclyl. According to the number of membered rings, the fused heterocyclyl can be divided into bicyclic, tricyclic, tetracyclic or polycyclic fused heterocyclyl, the fused heterocyclyl is preferably bicyclic or tricyclic fused heterocyclyl, and more preferably 5-membered/3-membered, 5-membered/4-membered or 5-membered/5-membered bicyclic fused heterocyclyl. Non-limiting examples of fused heterocyclyl include:

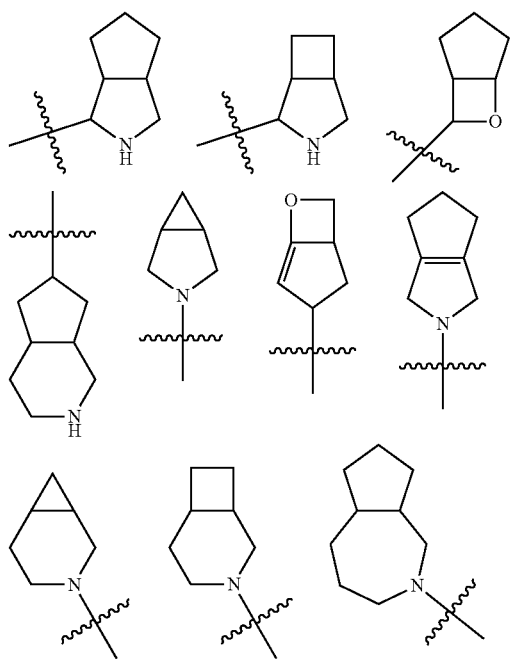

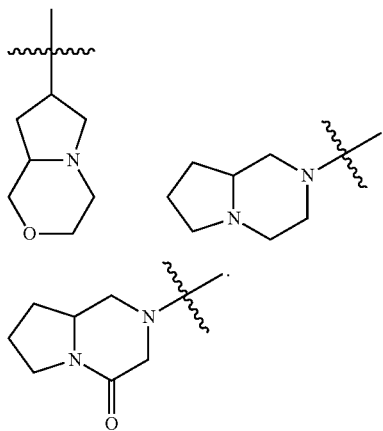

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and S(O)$_q$ (wherein q is an integer of 0 to 2), with the remaining ring atoms being carbon atoms. The bridged heterocyclyl is preferably 6 to 14 membered bridged heterocyclyl, and more preferably 7 to 10 membered bridged heterocyclyl. According to the number of membered rings, the bridged heterocyclyl can be divided into bicyclic, tricyclic, tetracyclic or polycyclic bridged heterocyclyl, and the bridged heterocyclyl is preferably bicyclic, tricyclic or tetracyclic bridged heterocyclyl, and more preferably bicyclic or tricyclic bridged heterocyclyl. Non-limiting examples of bridged heterocyclyls include:

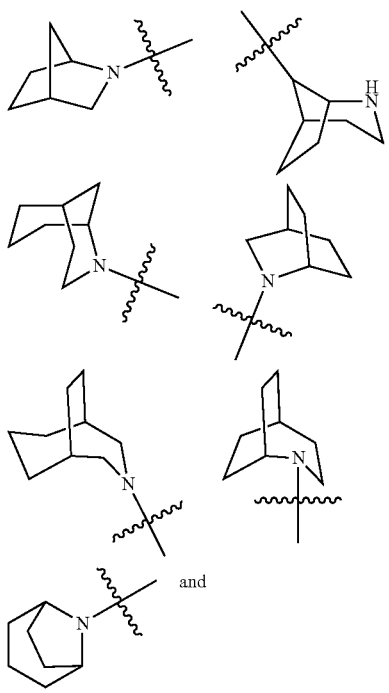

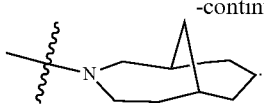

The ring of heterocyclyl can be fused to the ring of aryl, heteroaryl or cycloalkyl, wherein the ring bound to the parent structure is heterocyclyl. Non-limiting examples thereof include:

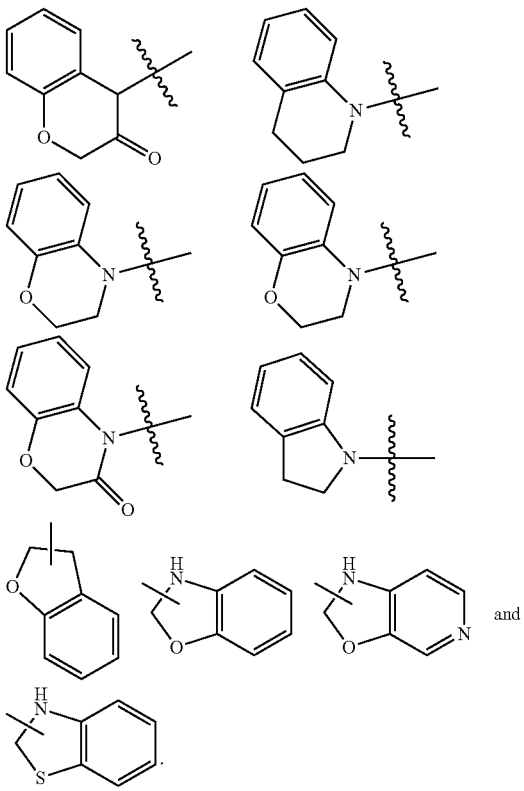

The heterocyclyl can be optionally substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio and —C(O)OR$^5$.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, for example, phenyl and naphthyl. The ring of aryl can be fused to the ring of heteroaryl, heterocyclyl or cycloalkyl, wherein the ring bound to the parent structure is aryl ring. Non-limiting examples thereof include:

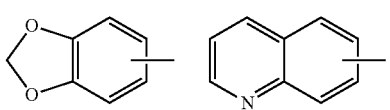

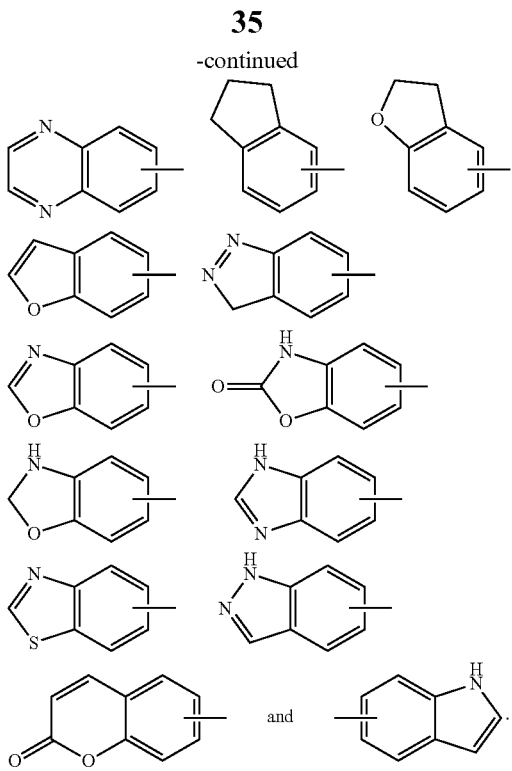

The aryl can be substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio and —C(O)OR$^5$.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, furanyl, thienyl, pyridyl, pyrrolyl, N-alkylpyrrolyl, pyrimidinyl, pyrazinyl, imidazolyl, pyrazolyl, tetrazolyl and the like, and preferably pyridyl. The ring of heteroaryl can be fused to the ring of aryl, heterocyclyl or cycloalkyl, wherein the ring bound to the parent structure is heteroaryl ring. Non-limiting examples thereof include:

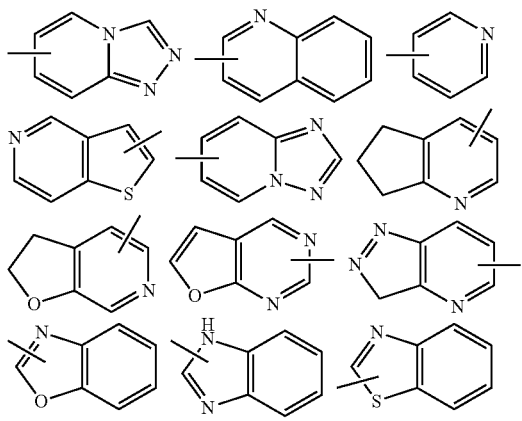

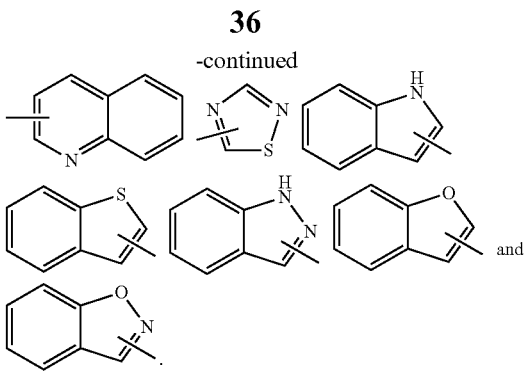

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio and —C(O)OR$^5$.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, and cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, amino, nitro, cyano, cycloalkyl, heterocyclyl, aryl, heteroaryl, cycloalkoxy, heteroalkoxy, cycloalkylthio, heterocyclylthio and —C(O)OR$^5$.

The term "haloalkyl" refers to an alkyl group substituted by one or more halogens, wherein the alkyl is as defined above.

The term "haloalkoxy" refers to an —O-(haloalkyl) group, wherein the haloalkyl is as defined above.

The term "heterocyclyloxy" refers to an —O-(heterocyclyl) group, wherein the heterocyclyl is as defined above.

The term "hydroxyalkyl" refers to an alkyl group substituted by hydroxy, wherein the alkyl is as defined above.

The term "hydroxy" refers to an —OH group.

The term "halogen" refers to fluorine, chlorine, bromine or iodine.

The term "amino" refers to a —NH$_2$ group.

The term "cyano" refers to a —CN group.

The term "nitro" refers to a —NO$_2$ group.

The term "oxo" refers to an =O group.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by the corresponding numbers of substituents. It goes without saying that the substituents only exist in their possible chemical position. The person skilled in the art is able to determine whether the substitution is possible or impossible by experiments or theory without paying excessive efforts. For example, the binding of an amino or hydroxy with free hydrogen to a carbon atom with unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate the administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity. $R^5$ is as defined in the formula (I).

DESCRIPTION OF THE DRAWING

FIG. 1 shows the pharmacodynamic effect of compound 2 on the uterine contraction model induced by OT in rat.

DETAILED DESCRIPTION OF THE INVENTION

Synthesis Methods of the Compounds of the Present Invention

In order to achieve the object of the present invention, the present invention applies the following technical solutions:

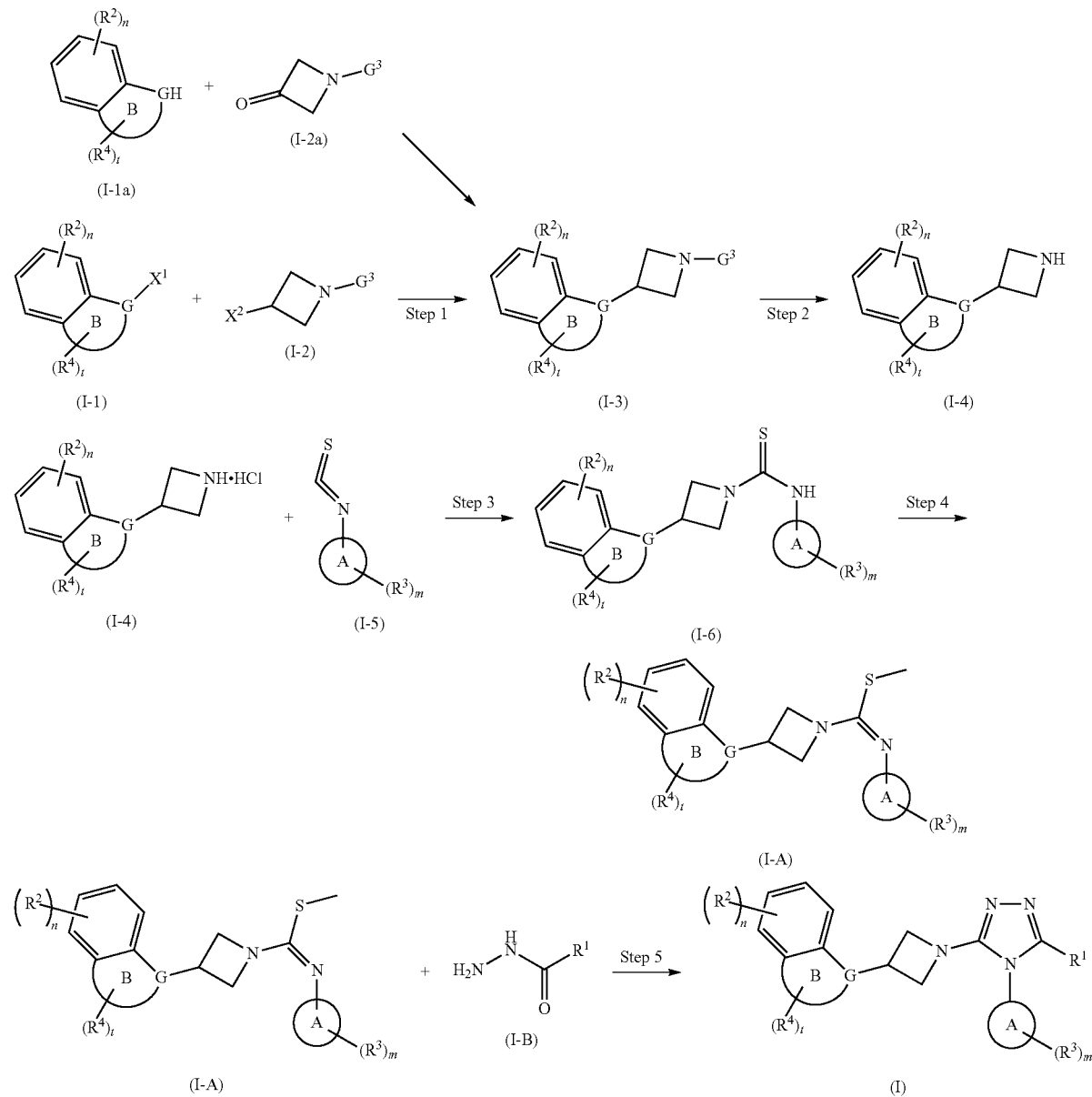

A method for preparing the compound of formula (I) of the present invention or a tautomer, mesomer, racemate, enantiomer, diastereomer thereof, or a mixture thereof, or a pharmaceutically acceptable salt thereof, comprises the following steps of:

Step 1: a compound of formula (I-1) and a compound of formula (I-2) are subjected to a coupling reaction in the presence of a catalyst to obtain a compound of formula (I-3); or a compound of formula (I-1a) and a compound of formula (I-2a) are subjected to a reduction reaction in the presence of a reducing reagent to obtain the compound of formula (I-3);

Step 2: the protecting group of the compound of formula (I-3) is removed under an acidic condition to obtain a compound of formula (I-4) or a salt thereof;

Step 3: the compound of formula (I-4) or a salt thereof and a compound of formula (I-5) are heated to obtain a compound of formula (I-6);

Step 4: the compound of formula (I-6) is reacted with a methylating agent under an alkaline condition to obtain a compound of formula (I-A);

Step 5: the compound of formula (I-A) and a compound of formula (I-B) or a salt thereof are subjected to a cyclization reaction under an acidic condition to obtain the compound of formula (I).

The catalyst includes, but is not limited to, palladium/carbon, Raney Ni, tetrakis(triphenylphosphine)palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-biphenyl)]palladium, [1,1'-bis(diphenylphosphino)ferrocene] palladium dichloride, 1,1'-bis(dibenzylphosphoryl) dichloroferrocene palladium or tris(dibenzylideneacetone) dipalladium, and preferably bis(dibenzylideneacetone) palladium.

The reducing reagent includes, but is not limited to, lithium aluminum hydride, sodium borohydride, DIBAL-H, $NaAlH(O-t-Bu)_3$, $AlH_3$, $NaCNBH_3$, $Na(AcO)_3BH$, $B_2H_5$, $Li(Et)_3BH$, $Pd/C/H_2$ and $Raney Ni/H_2$.

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The methylating agent includes, but is not limited to, methyl p-toluenesulfonate, methyl iodide, methyl Grignard reagent, dimethyl sulfate, methyl trifluoromethanesulfonate and diazomethane.

The reagent that provides an acidic condition includes, but is not limited to, hydrogen chloride, a solution of hydrogen chloride in 1,4-dioxane, trifluoroacetic acid, formic acid, acetic acid, hydrochloric acid, sulfuric acid, methanesulfonic acid, nitric acid, phosphoric acid, p-toluenesulfonic acid, $Me_3SiCl$ and $TMSOT_f$.

The above reactions are preferably carried out in a solvent. The solvent includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and the mixtures thereof Wherein:
G is selected from the group consisting of C, CH and N;
$X^1$ and $X^2$ are both halogen;

$G^3$ is selected from the group consisting of tert-butoxycarbonyl, acetyl, benzyl, allyl and p-methoxybenzyl;

ring A, ring B, $R^1$-$R^4$, n, m and t are as defined in formula (I).

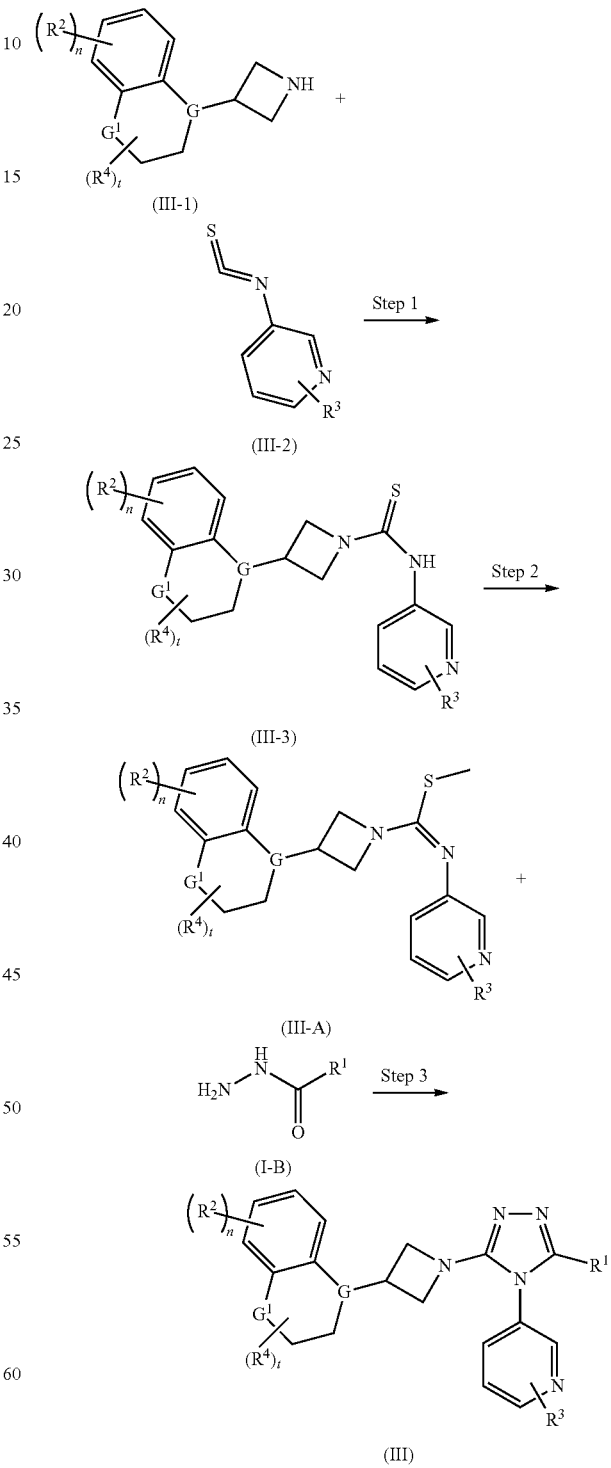

Scheme II

A method for preparing the compound of formula (III) of the present invention or a tautomer, mesomer, racemate, enantiomer, diastereomer thereof, or a mixture thereof, or a pharmaceutically acceptable salt thereof, comprises the following steps of:

Step 1: a compound of formula (III-1) or a salt thereof and a compound of formula (III-2) are heated to obtain a compound of formula (III-3);

Step 2: the compound of formula (III-3) is reacted with a methylating agent under an alkaline condition to obtain a compound of formula (III-A);

Step 3: the compound of formula (III-A) and a compound of formula (I-B) or a hydrochloride salt thereof are subjected to a cyclization reaction under an acidic condition to obtain the compound of formula (III).

The methylating agent includes, but is not limited to, methyl p-toluenesulfonate, methyl iodide, methyl Grignard reagent, dimethyl sulfate, methyl trifluoromethanesulfonate and diazomethane.

The reagent that provides an acidic condition includes, but is not limited to, hydrogen chloride, trifluoroacetic acid, formic acid, acetic acid, hydrochloric acid, sulfuric acid, methanesulfonic acid, nitric acid, phosphoric acid, p-toluenesulfonic acid, Me$_3$SiCl and TMSOT$_f$.

The above reactions are preferably carried out in a solvent. The solvent includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:
G is selected from the group consisting of C, CH and N;
G$^1$ is selected from the group consisting of N, NH, C, CH, CH$_2$ and O;
R$^1$-R$^4$, n and t are as defined in formula (I).

Scheme III

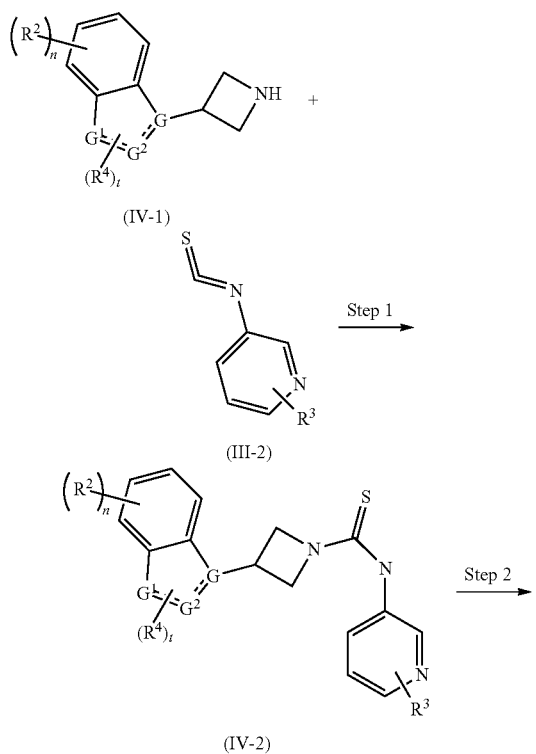

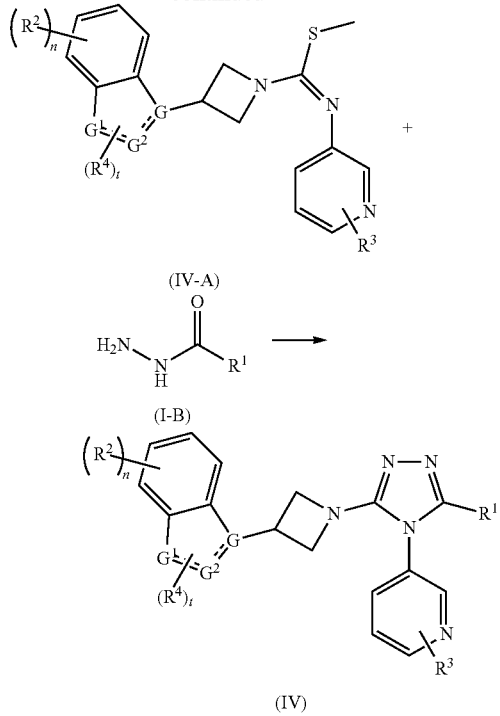

A method for preparing the compound of formula (IV) of the present invention or a tautomer, mesomer, racemate, enantiomer, diastereomer thereof, or a mixture thereof, or a pharmaceutically acceptable salt thereof, comprises the following steps of:

Step 1: a compound of formula (IV-1) or a salt thereof and a compound of formula (III-2) are heated to obtain a compound of formula (IV-2);

Step 2: the compound of formula (IV-2) is reacted with a methylating agent under an alkaline condition to obtain a compound of formula (IV-A);

Step 3: the compound of formula (IV-A) and a compound of formula (I-B) or a hydrochloride salt thereof are subjected to a cyclization reaction under an acidic condition to obtain the compound of formula (IV).

The methylating agent includes, but is not limited to, methyl p-toluenesulfonate, methyl iodide, methyl Grignard reagent, dimethyl sulfate, methyl trifluoromethanesulfonate and diazomethane.

The reagent that provides an acidic condition includes, but is not limited to, hydrogen chloride, trifluoroacetic acid, formic acid, acetic acid, hydrochloric acid, sulfuric acid, methanesulfonic acid, nitric acid, phosphoric acid, p-toluenesulfonic acid, Me$_3$SiCl and TMSOT$_f$.

The above reactions are preferably carried out in a solvent. The solvent includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:
⸺ is a single bond or a double bond;
G is selected from the group consisting of C, CH and N;
G$^1$ is selected from the group consisting of N, NH, C, CH, CH$_2$, O and S;
G$^2$ is selected from the group consisting of C, CH, CH$_2$, N and NH;
R$^1$-R$^4$, n and t are as defined in formula (I).

EXAMPLES

The structures of the compounds are identified by nuclear magnetic resonance (NMR) and/or mass spectrometry (MS). NMR shifts (δ) are given in $10^{-6}$ (ppm). NMR is determined by a Bruker AVANCE-400 machine. The solvent for determination is deuterated-dimethyl sulfoxide (DMSO-$d_6$), deuterated-chloroform (CDCl$_3$) or deuterated-methanol (CD$_3$OD), with tetramethylsilane (TMS) as the internal standard.

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Chiral HPLC is determined on a LC-10A vp (Shimadzu) or SFC-analytical (Berger Instruments Inc.).

Yantai Huanghai HSGF254 or Qingdao GF254 silica gel plate is used for the thin-layer silica gel chromatography (TLC). The dimension of the silica gel plate used in TLC is 0.15 mm to 0.2 mm, and 0.4 mm to 0.5 mm for purification of product.

Yantai Huanghai 200 to 300 mesh silica gel is generally used as a carrier for column chromatography.

Prep Star SD-1 (Varian Instruments Inc.) or SFC-multigram (Berger Instruments Inc.) is used for chiral preparative column chromatography.

CombiFlash rapid preparation instrument is Combiflash Rf200 (TELEDYNE ISCO).

The average kinase inhibition rates and IC$_{50}$ values are determined by a NovoStar microplate reader (BMG Co., Germany).

The known starting raw materials of the present invention may be prepared by the known methods in the art, or may be purchased from ABCR GmbH & Co. KG, Acros Organics, Aldrich Chemical Company, Accela ChemBio Inc., or Dari chemical Company, etc.

Unless otherwise stated, the reactions are carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reaction is performed on a Parr 3916EKX hydrogenation instrument and a Qinglan QL-500 hydrogen generator or HC2-SS hydrogenation instrument.

In hydrogenation reactions, the reaction system is generally vacuumed and filled with hydrogen, with the above operation is repeated three times.

CEM Discover-S 908860 type microwave reactor is used in microwave reactions.

Unless otherwise stated, the solution refers to an aqueous solution.

Unless otherwise stated, the reaction temperature is room temperature from 20° C. to 30° C.

The reaction process in the examples is monitored by thin layer chromatography (TLC). The developing solvent used during the reactions, the eluent system for the column chromatography and the developing solvent system for the thin layer chromatography for purification of the compounds include: A: dichloromethane/methanol system, B: n-hexane/ethyl acetate system, and C: petroleum ether/ethyl acetate system. The ratio of the volume of the solvent is adjusted according to the polarity of the compounds, and a small quantity of alkaline reagent such as triethylamine or acidic reagent such as acetic acid may also be added for adjustment.

Example 1

7-Fluoro-4-(1-(5-(methoxymethyl)-4-(6-methoxy-pyridin-3-yl)-4H-1,2,4-triazol-3-yl)azetidin-3-yl)quinoline 1

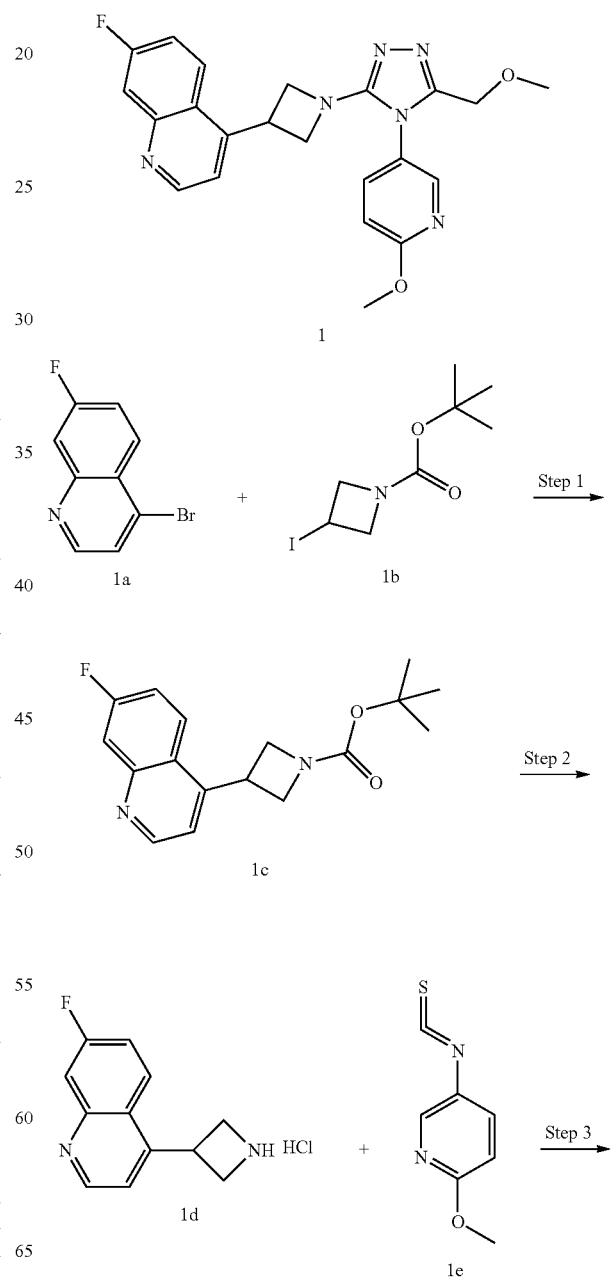

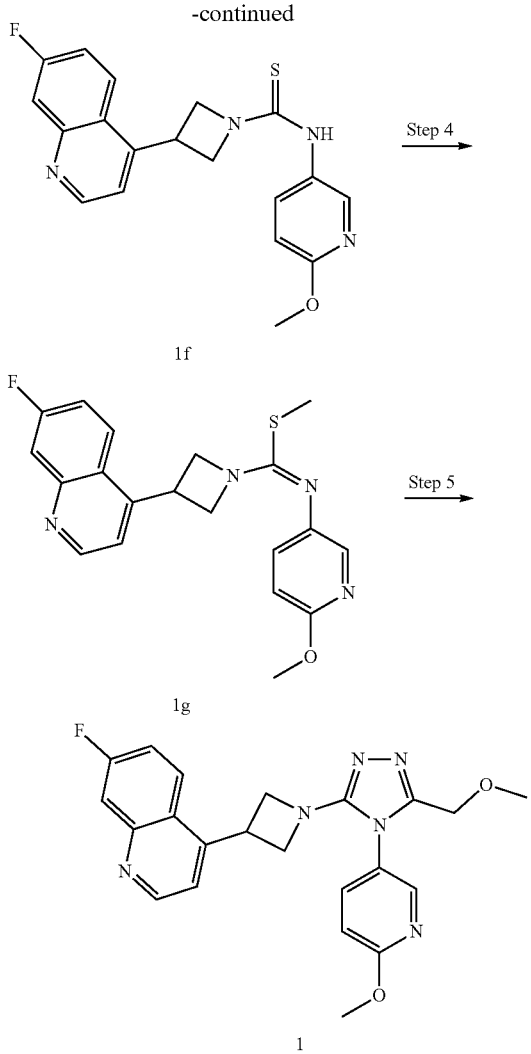

Step 1

Tert-butyl 3-(7-fluoroquinolin-4-yl)azetidine-1-carboxylate 1c

Zinc (173.54 mg, 2.65 mmol), iodine (112.28 mg, 0.4400 mmol) and tert-butyl 3-iodoazetidine-1-carboxylate 1b (250.48 mg, 0.88 mmol, prepared according to the known method disclosed in "*Organic Letters*, 2014, 16(23), 6160-6163") were dissolved in 30 mL of N,N-dimethylformamide. After addition, the reaction solution was reacted for 1 hour under argon atmosphere. The reaction solution was then added with bis(dibenzylideneacetone)palladium (405.1 mg, 0.4400 mmol), 2-dicyclohexylphosphine-2',4',6'-triisopropylbiphenyl (211 mg, 0.44 mmol) and 4-bromo-7-fluoroquinoline 1a (200 mg, 0.88 mmol, Accela ChemBio Inc.). After addition, the reaction solution was heated and stirred at 50° C. to react for 3 hours. The reaction solution was cooled to room temperature, and concentrated under reduced pressure to remove the organic solvent. The resulting residues were purified by silica gel column chromatography with elution system C to obtain the title product 1c (9.5 g, yellow solid), yield: 64.6%.

MS m/z (ESI): 303.2 [M+1].

Step 2

4-(Azetidin-3-yl)-7-fluoroquinoline Hydrochloride 1d

Compound 1c (100 mg, 0.33 mmol) and 0.83 mL solution of hydrogen chloride in 1,4-dioxane (4 M) were dissolved in 5 mL of dichloromethane successively, and the reaction solution was stirred for 3 hours. The above reaction solution was concentrated under reduced pressure to remove the solvent to give the crude title product 1d (100 mg, white solid), which was used directly in the next step without purification.

MS m/z (ESI): 203.4 [M+1].

Step 3

3-(7-Fluoroquinolin-4-yl)-N-(6-methoxypyridin-3-yl)azetidine-1-carbothioamide 1f 5-Isothiocyanato-2-methylpyridine 1e (82.18 mg, 0.49 mmol, prepared according to the known method disclosed in "*Bioorganic & Medicinal Chemistry Letters*, 2010, 20(2), 516-520") and the crude product 1d (100 mg, 0.49 mmol) were dissolved in 20 mL of dichloromethane. After addition, the reaction solution was stirred for 3 hours. The reaction solution containing the title product 1f was used directly in the next step without purification.

MS m/z (ESI): 369.2 [M+1].

Step 4

Methyl (E)-3-(7-fluoroquinolin-4-yl)-N-(6-methoxy-pyridin-3-yl)azetidine-1-carbimidothioate 1g The crude product 1f (100 mg, 0.27 mmol) and potassium tert-butoxide (60.91 mg, 0.54 mmol) were dissolved in 20 mL of tetrahydrofuran, and the reaction solution was stirred in an ice bath for 1 hour. The above reaction solution was added with methyl 4-methylbenzenesulfonate (101.09 mg, 0.54 mmol), and stirred at room temperature for 12 hours. The solvent was removed, and the resulting residues were purified by thin layer chromatography with developing solvent system C to obtain the title product 1g (50 mg, yellow oil), yield: 38.5%.

MS m/z (ESI): 383.4 [M+1].

Step 5

7-Fluoro-4-(1-(5-(methoxymethyl)-4-(6-methoxy-pyridin-3-yl)-4H-1,2,4-triazol-3-yl)azetidin-3-yl)quinoline 1

Compound 1g (50 mg, 0.13 mmol), trifluoroacetic acid (29.81 mg, 0.26 mmol) and 2-methoxyacetylhydrazine (27.22 mg, 0.26 mmol) were dissolved in 20 mL of tetrahydrofuran. After addition, the reaction solution was stirred at 65° C. for 3 hours. The reaction solution was cooled to room temperature, and concentrated under reduced pressure to remove the solvent. The resulting residues were purified by high performance liquid chromatography to obtain the title product 1 (10 mg, colorless paste), yield: 17.1%.

MS m/z (ESI): 421.4 [M+1].
$^1$H NMR (400 MHz, CD$_3$OD) δ 8.85 (d, 1H), 8.32 (d, 1H), 7.98-7.94 (m, 1H), 7.85-7.82 (m, 1H), 7.71-7.65 (m,

1H), 7.68-7.46 (m, 2H), 7.00 (d, 1H), 4.78-4.70 (m, 1H), 4.39-4.30 (m, 4H), 4.13-4.09 (m, 2H), 4.00 (s, 3H), 3.26 (s, 3H).

Example 2

5-(3-(3-(6-Fluoronaphthalen-1-yl)azetidin-1-yl)-5-(methoxymethyl)-4H-1,2,4-triazol-4-yl)-2-methoxypyridine 2

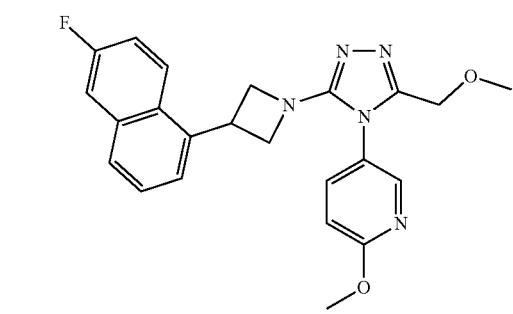

2

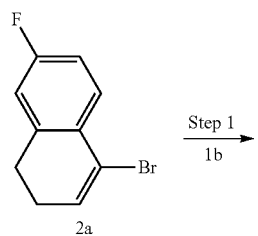

2a

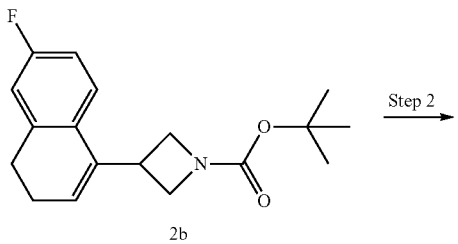

2b

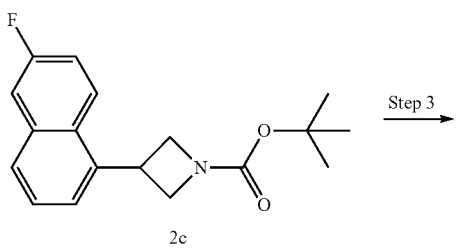

2c

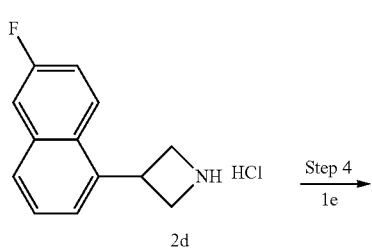

2d

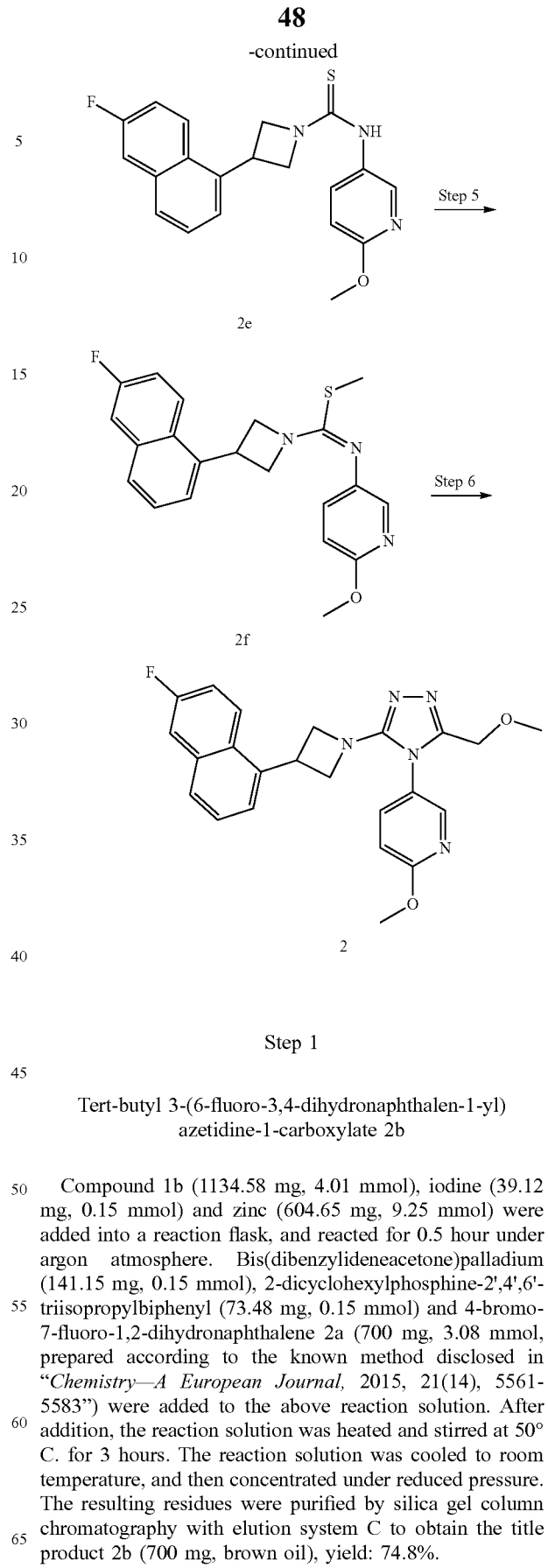

Step 1

Tert-butyl 3-(6-fluoro-3,4-dihydronaphthalen-1-yl)azetidine-1-carboxylate 2b

Compound 1b (1134.58 mg, 4.01 mmol), iodine (39.12 mg, 0.15 mmol) and zinc (604.65 mg, 9.25 mmol) were added into a reaction flask, and reacted for 0.5 hour under argon atmosphere. Bis(dibenzylideneacetone)palladium (141.15 mg, 0.15 mmol), 2-dicyclohexylphosphine-2',4',6'-triisopropylbiphenyl (73.48 mg, 0.15 mmol) and 4-bromo-7-fluoro-1,2-dihydronaphthalene 2a (700 mg, 3.08 mmol, prepared according to the known method disclosed in "*Chemistry—A European Journal*, 2015, 21(14), 5561-5583") were added to the above reaction solution. After addition, the reaction solution was heated and stirred at 50° C. for 3 hours. The reaction solution was cooled to room temperature, and then concentrated under reduced pressure. The resulting residues were purified by silica gel column chromatography with elution system C to obtain the title product 2b (700 mg, brown oil), yield: 74.8%.

MS m/z (ESI): 304.1 [M+1].

Step 2

Tert-butyl 3-(6-fluoronaphthalen-1-yl)azetidine-1-carboxylate 2c 2,3-Dichloro-5,6-dicyano-p-quinone (336.72 mg, 1.48 mmol) and 2b (300 mg, 0.99 mmol) were dissolved in 30 mL of toluene, and then reacted at 80° C. for 12 hours after addition. The reaction solution was cooled to room temperature, and then concentrated under reduced pressure to remove the solvent. The resulting residues were purified by thin layer chromatography with developing solvent system C to obtain the title product 2c (180 mg, brown oil), yield: 60.4%.

MS m/z (ESI): 302.2 [M+1].

Step 3

3-(6-Fluoronaphthalen-1-yl)azetidine Hydrochloride 2d

Compound 2c (180 mg, 0.60 mmol) and 0.5 mL solution of hydrogen chloride in 1,4-dioxane (4 M) were dissolved in 30 mL of dichloromethane, and reacted for 2 hours after addition. The above reaction solution was concentrated under reduced pressure to obtain the crude title product 2d (120 mg, brown solid), which was used directly in the next step without purification.

MS m/z (ESI): 202.1 [M+1].

Step 4

3-(6-Fluoronaphthalen-1-yl)-N-(6-methoxypyridin-3-yl)azetidine-1-carbothioamide 2e The crude product 2d (120 mg, 0.6) and 1e (99.11 mg, 0.60 mmol) were added to 50 mL of tetrahydrofuran, and the reaction solution was stirred for 2 hours after addition. The resulting reaction solution containing the title product 2e was used directly in the next step without purification.

MS m/z (ESI): 368.1 [M+1].

Step 5

Methyl (E)-3-(6-fluoronaphthalen-1-yl)-N-(6-methoxypyridin-3-yl)azetidine-1-carbimidothioate 2f The crude product 2e (200 mg, 0.54 mmol) was dissolved in 50 mL of tetrahydrofuran, and cooled to 0° C. The above solution was added with potassium tert-butoxide (183.23 mg, 1.63 mmol), and then reacted for 1 hour after addition. The above reaction solution was added with methyl 4-methylbenzenesulfonate (101.09 mg, 0.54 mmol), and stirred at room temperature for 12 hours. The reaction solution was then added with 50 mL of ethyl acetate, and washed with water (20 mL×3). The organic phases were combined, and concentrated under reduced pressure to remove the solvent. The resulting residues were purified by thin layer chromatography with developing solvent system C to obtain the title product 2f (100 mg, brown oil), yield: 48.2%.

MS m/z (ESI): 382.1 [M+1].

Step 6

5-(3-(3-(6-Fluoronaphthalen-1-yl)azetidin-1-yl)-5-(methoxymethyl)-4H-1,2,4-triazol-4-yl)-2-methoxypyridine 2

Compound 2f (100 mg, 0.26 mmol), trifluoroacetic acid (0.1 mL, 0.13 mmol) and 2-methoxyacetylhydrazine (27.29 mg, 0.26 mmol) were dissolved in 50 mL of tetrahydrofuran. After addition, the reaction solution was reacted under reflux for 3 hours. The reaction solution was cooled to room temperature, and concentrated under reduced pressure to remove the solvent. The resulting residues were purified by thin layer chromatography with developing solvent system A to obtain the title product 2 (30 mg, brown solid), yield: 26.7%.

MS m/z (ESI): 420.1 [M+1].

<sup>1</sup>H NMR (400 MHz, CD<sub>3</sub>OD) δ 8.32 (s, 1H), 7.75-7.84 (m, 3H), 7.51-7.55 (m, 2H), 7.43 (d, 1H), 7.25-7.32 (m, 1H), 7.00 (d, 1H), 4.51-4.66 (m, 1H), 4.35 (t, 4H), 4.10 (t, 2H), 4.00 (s, 3H), 3.26 (s, 3H).

Example 3

1-(1-(4-(Benzo[d][1,3]dioxolan-5-yl)-5-(methoxymethyl)-4H-1,2,4-triazol-3-yl)azetidin-3-yl)-3-chloro-5-fluoro-1H-indole 3

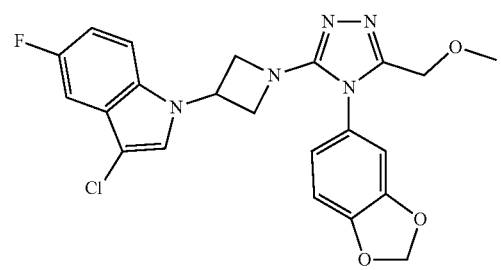

-continued

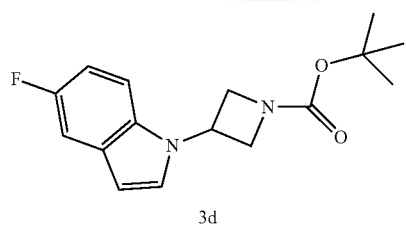

3d

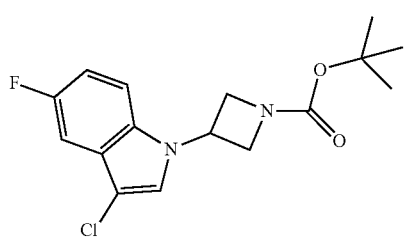

3e

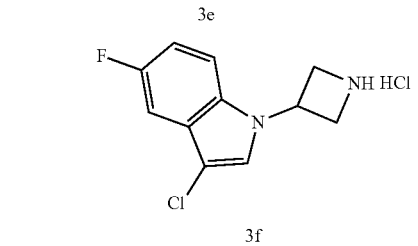

3f

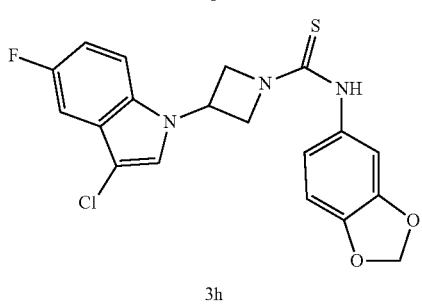

3h

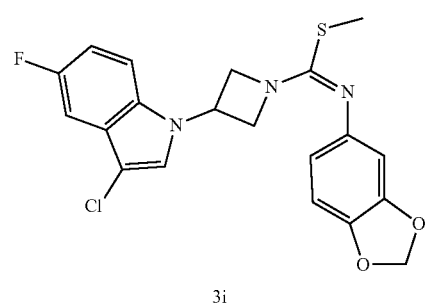

3i

-continued

3

Step 1

Tert-butyl 3-(5-fluoroindolin-1-yl)azetidine-1-carboxylate 3c

5-Fluoroindoline 3a (2000 mg, 7.44 mmol) and tert-butyl 3-oxoazetidine-1-carboxylate 3b (1273.16 mg, 7.44 mmol, prepared according to the known method disclosed in "*Organic Process Research & Development*, 2015, 19(11), 1548-1553") were dissolved in 30 mL of dichloromethane successively, and reacted for 1 hour. The reaction solution was then added with sodium triacetoxyborohydride (3.15 g, 14.88 mmol), and reacted for 12 hours after addition. The reaction solution was concentrated under reduced pressure, and the resulting residues were dissolved in 50 mL of ethyl acetate, and washed with saturated sodium bicarbonate solution (30 mL×2). The organic phase was dried over anhydrous sodium sulfate, and filtered to remove the drying agent. The filtrate was concentrated under reduced pressure, and the resulting residues were purified by silica gel column chromatography with elution system C to obtain the title product 3c (1.50 g, white solid), yield: 69.0%.

MS m/z (ESI): 293.1 [M+1].

Step 2

Tert-butyl 3-(5-fluoro-1H-indol-1-yl)azetidine-1-carboxylate 3d

Compound 3c (400 mg, 1.37 mmol) was dissolved in 20 mL of dichloromethane, and the solution was placed in an ice bath to cool to 0° C. The above solution was then added with 2,3-dichloro-5,6-dicyano-p-quinone (310.59 mg, 1.37 mmol), and reacted for 1 hour after addition. The reaction solution was concentrated under reduced pressure to remove the organic solvent. The resulting residues were purified by thin layer chromatography with developing solvent system C to obtain the title product 3d (100 mg, colorless oil), yield: 25.2%.

MS m/z (ESI): 291.3 [M+1].

Step 3

Tert-butyl 3-(3-chloro-5-fluoro-1H-indol-1-yl)azetidine-1-carboxylate 3e

Compound 3d (100 mg, 0.34 mmol) and N-chlorosuccinimide (68.99 mg, 0.52 mmol) were dissolved in 10 mL of tetrahydrofuran successively. After addition, the reaction solution was heated and reacted at 60° C. for 3 hours. The reaction solution was concentrated under reduced pressure to remove the solvent, and the resulting residues were purified by thin layer chromatography with developing solvent system C to obtain the title product 3e (100 mg, colorless oil), yield: 89.4%.

MS m/z (ESI): 325.5 [M+1].

Step 4

1-(Azetidin-3-yl)-3-chloro-5-fluoro-1H-indole Hydrochloride 3f

Compound 3e (80 mg, 0.25 mmol) and 2 mL solution of hydrogen chloride in 1,4-dioxane (4 M) were dissolved in 20 mL of dichloromethane, and reacted for 1 hour after addition. The reaction solution was concentrated under reduced pressure to remove the organic solvent. The crude title product 3f was obtained, which was used directly in the next step without purification.

MS m/z (ESI): 225.3 [M+1].

Step 5

N-(Benzo[d][1,3]dioxolan-5-yl)-3-(3-chloro-5-fluoro-1H-indol-1-yl)azetidine-1-carbothioamide 3h 5-Isothiocyanatobenzo[d][1,3]dioxole 3g (43.87 mg, 0.24 mmol, prepared according to the known method disclosed in "*Journal of Medicinal Chemistry*, 2015, 58(3), 1123-1139") and compound 3f (55 mg, 0.24 mmol) were dissolved in 30 mL of tetrahydrofuran, and reacted for 2 hours after addition. The reaction solution containing the title product 3h was used directly in the next step without purification.

MS m/z (ESI): 404.3 [M+1].

Step 6

Methyl (E)-N-benzo[d][1,3]dioxolan-5-yl-3-(3-chloro-5-fluoro-1H-indol-1-yl)azetidine-1-carbimidothioate 3i The crude product 3h (98 mg, 0.24 mmol) was dissolved in 30 mL of tetrahydrofuran, and cooled to 0° C. The above solution was added with potassium tert-butoxide (60.91 mg, 0.54 mmol), and reacted in an ice bath for 1 hour after addition. The above reaction solution was added with methyl 4-methylbenzenesulfonate (45.19 mg, 0.24 mmol), and stirred at room temperature for 12 hours. The reaction solution was concentrated under reduced pressure to remove the organic solvent. The resulting residues were added with ethyl acetate (50 mL×2), and washed with water (30 mL×2). The organic phase was dried over anhydrous sodium sulfate, and filtered to remove the drying agent. The filtrate was concentrated under reduced pressure, and the resulting residues were purified by thin layer chromatography with developing solvent system C to obtain the title product 3i (98 mg, yellow oil), yield: 96.6%.

MS m/z (ESI): 418.3 [M+1].

Step 7

1-(1-(4-(Benzo[d][1,3]dioxolan-5-yl)-5-(methoxymethyl)-4H-1,2,4-triazol-3-yl)azetidin-3-yl)-3-chloro-5-fluoro-1H-indole 3

Compound 3i (98 mg, 0.23 mmol), trifluoroacetic acid (29.81 mg, 0.26 mmol) and 2-methoxyacetylhydrazine (24.42 mg, 0.23 mmol) were dissolved in 30 mL of tetrahydrofuran. After addition, the reaction solution was heated to reflux and reacted for 3 hours. The reaction solution was concentrated under reduced pressure to remove the solvent, and the resulting residues were purified by thin layer chromatography with developing solvent system A to obtain the title product 3 (30 mg, brown oil), yield: 26.7%.

MS m/z (ESI): 456.4 [M+1].

$^1$H NMR (400 MHz, CD$_3$OD) δ 7.64 (s, 1H), 7.51-7.52 (m, 1H), 7.17-7.20 (m, 1H), 6.99-7.05 (m, 4H), 6.09 (s, 2H), 5.36-5.40 (m, 1H), 4.34-4.39 (m, 4H), 4.04-4.09 (m, 2H), 3.28 (s, 3H).

Example 4

3-Chloro-1-(1-(5-(ethoxymethyl)-4-(6-methoxypyridin-3-yl)-4H-1,2,4-triazol-3-yl)azetidin-3-yl)-5-fluoro-1H-indole 4

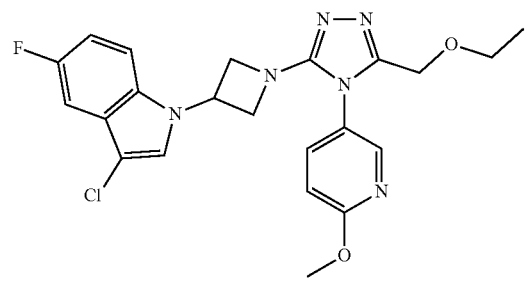

4

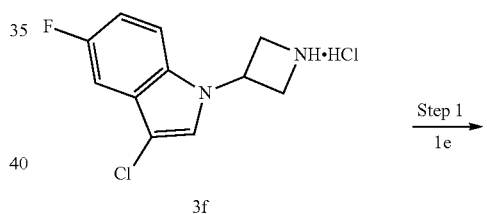

3f

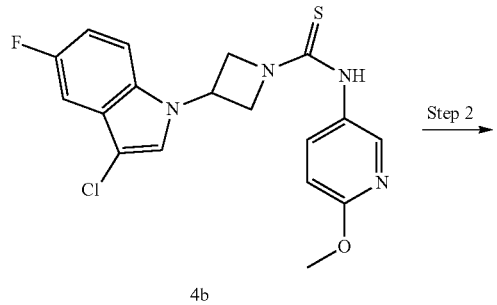

4b

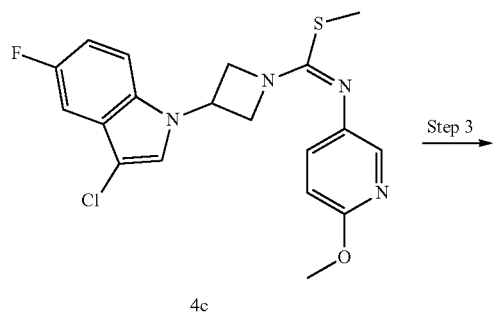

4c

-continued

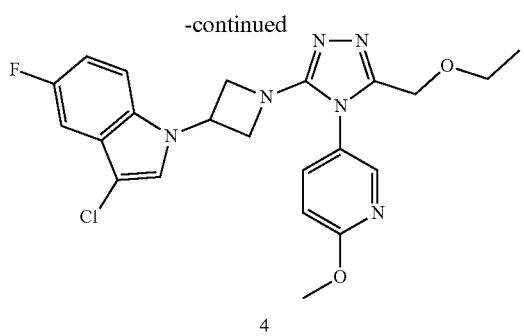

4

Step 1

3-(3-Chloro-5-fluoro-1H-indol-1-yl)-N-(6-methoxy-pyridin-3-yl)azetidine-1-carbothioamide 4a The crude product 3f (162 mg, 0.62 mmol) and compound 1e (201.43 mg, 0.62 mmol) were dissolved in 10 mL of dichloromethane, and reacted for 2 hours after addition. The reaction solution was concentrated under reduced pressure to remove the organic solvent to give the crude title product 4a (373 mg, brown solid), which was used directly in the next step without purification.

MS m/z (ESI): 391.2 [M+1].

Step 2

Methyl (E)-3-(3-chloro-5-fluoro-1H-indol-1-yl)-N-(6-methoxypyridin-3-yl)azetidine-1-carbimidothioate 4b The crude product 4a (373 mg, 0.62 mmol) was dissolved in 15 mL of tetrahydrofuran, and cooled to 0° C. The above solution was added with potassium tert-butoxide (208.17 mg, 1.86 mmol), and reacted for 1 hour after addition. The above reaction solution was added with methyl 4-methyl-benzenesulfonate (172.74 mg, 0.93 mmol), and then slowly warmed up to room temperature and stirred for 16 hours. The reaction solution was concentrated under reduced pressure to remove the organic solvent. The resulting residues were purified by thin layer chromatography with developing solvent system C to obtain the title product 4b (140 mg, yellow oil), yield: 55.9%.

MS m/z (ESI): 405.3 [M+1].

Step 3

3-Chloro-1-(1-(5-(ethoxymethyl)-4-(6-methoxypyridin-3-yl)-4H-1,2,4-triazol-3-yl)azetidin-3-yl)-5-fluoro-1H-indole 4

Compound 4b (70 mg, 0.17 mmol), trifluoroacetic acid (0.006 mL, 0.085 mmol) and 2-ethoxyacetylhydrazine (40.85 mg, 0.35 mmol) were dissolved in 30 mL of tetrahydrofuran successively. After addition, the reaction solution was heated to 70° C. and reacted for 3 hours. The reaction solution was concentrated under reduced pressure, and the resulting residues were purified by thin layer chromatography with developing solvent system A to obtain the title product 4 (60 mg, pale yellow oil), yield: 76.0%.

MS m/z (ESI): 457.1 [M+1].
$^1$H NMR (400 MHz, CD$_3$OD) δ 8.34 (d, 1H), 7.86 (d, 1H), 7.66 (s, 1H), 7.48 (d, 1H), 7.18 (d, 1H), 7.03 (d, 1H), 6.98 (d, 1H), 5.39-5.42 (m, 1H), 4.40 (s, 2H), 4.34 (t, 2H), 4.14 (d, 2H), 3.98 (s, 3H), 3.61-3.66 (m, 2H), 1.26 (t, 3H).

Example 5

1-(1-(5-(Ethoxymethyl)-4-(6-methoxypyridin-3-yl)-4H-1,2,4-triazol-3-yl)azetidin-3-yl)-5-fluoro-3-methyl-1H-indole 5

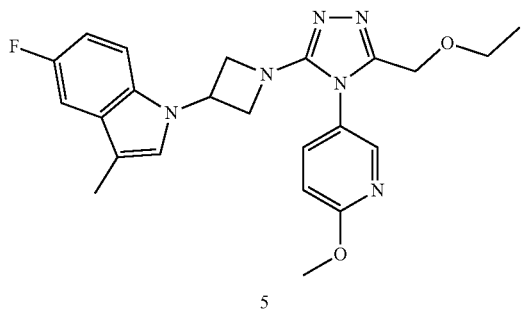

5

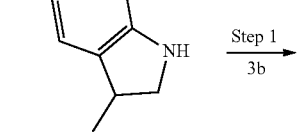

5a

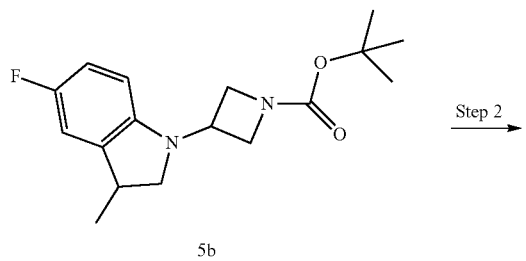

5b

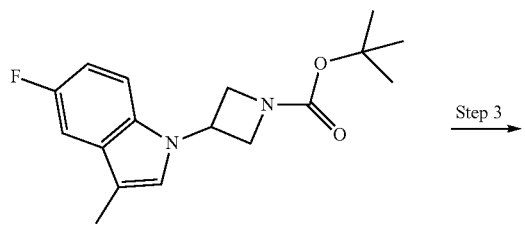

5c

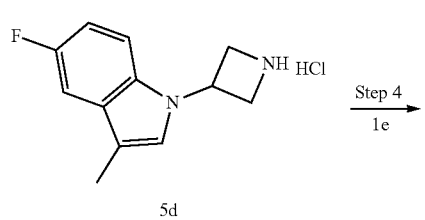

5d

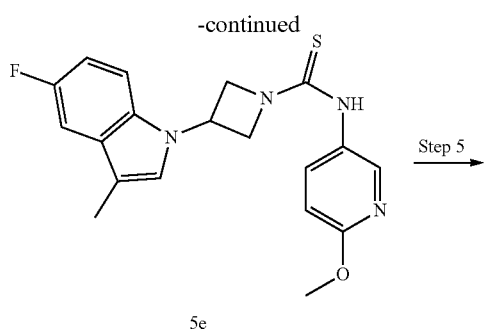

5e

5f

5

Step 1

Tert-butyl 3-(5-fluoro-3-methylindolin-1-yl)azetidine-1-carboxylate 5b

5-Fluoro-3-methylindoline 5a (1912.34 mg, 6.70 mmol, prepared according to the method disclosed in the patent application "WO2009065919") and compound 3b (1147.69 mg, 6.7 mmol) were dissolved in 30 mL of dichloromethane successively, and reacted for 1 hour. The reaction solution was then added with sodium triacetoxyborohydride (2.84 g, 13.4 mmol), and reacted for 12 hours after addition. The reaction solution was concentrated under reduced pressure to remove the organic solvent. The resulting residues were dissolved in 50 mL of ethyl acetate, and washed with saturated sodium bicarbonate solution (30 mL×2). The organic phases were combined, dried over anhydrous sodium sulfate, and filtered to remove the drying agent. The filtrate was concentrated under reduced pressure, and the resulting residues were purified by silica gel column chromatography with elution system C to obtain the title product 5b (1330 mg, colorless oil), yield: 64.8%.

MS m/z (ESI): 307.3 [M+1].

Step 2

Tert-butyl 3-(5-fluoro-3-methyl-1H-indol-1-yl)azetidine-1-carboxylate 5c

Compound 5b (1330 mg, 4.34 mmol) was dissolved in 30 mL of dichloromethane, and the solution was placed in an ice bath to cool to 0° C. The above solution was then added with 2,3-dichloro-5,6-dicyano-p-quinone (985.41 mg, 4.34 mmol), and reacted for 1 hour after addition. The reaction solution was concentrated under reduced pressure. The resulting residues were purified by thin layer chromatography with developing solvent system C to obtain the title product 5c (1160 mg, colorless oil), yield: 87.8%.

MS m/z (ESI): 305.1 [M+1].

Step 3

1-(Azetidin-3-yl)-5-fluoro-3-methyl-1H-indole Hydrochloride 5d

Compound 5c (500 mg, 1.64 mmol) was dissolved in 10 mL of dichloromethane. The above solution was then added with 2.05 mL solution of hydrogen chloride in 1,4-dioxane (4 M), and reacted for 2 hours after addition. The reaction solution was concentrated under reduced pressure to remove the organic solvent to give the crude title product 5d (400 mg, white solid), which was used directly in the next step without purification.

MS m/z (ESI): 205.1 [M+1].

Step 4

3-(5-Fluoro-3-methyl-1H-indol-1-yl)-N-(6-methoxypyridin-3-yl)azetidine-1-carbothioamide 5e The crude product 5d (400 mg, 1.66 mmol) and compound 1e (563.66 mg, 1.66 mmol) were dissolved in 40 mL of dichloromethane successively, and reacted for 2 hours after addition. The reaction solution was concentrated under reduced pressure to remove the organic solvent to give the crude title product 5e (980 mg, yellow solid), which was used directly in the next step without purification.

MS m/z (ESI): 371.2 [M+1].

Step 5

Methyl (E)-3-(5-fluoro-3-methyl-1H-indol-1-yl)-N-(6-methoxypyridin-3-yl)azetidine-1-carbimidothioate 5f The crude product 5e (980 mg, 1.66 mmol) was dissolved in 40 mL of tetrahydrofuran, and cooled to 0° C. The above solution was added with potassium tert-butoxide (372.25 mg, 3.32 mmol), and reacted for 1 hour after addition. The above reaction solution was added with methyl 4-methylbenzenesulfonate (370.69 mg, 1.99 mmol), and then slowly warmed up to room temperature, and reacted for 16 hours. The reaction solution was concentrated under reduced pressure to remove the organic solvent. The resulting residues were added with 60 mL of ethyl acetate, and washed with water (30 mL×2). The organic phases were combined, dried over anhydrous sodium sulfate, and filtered. The filtrate was concentrated under reduced pressure, and the resulting residues were purified by silica gel column chromatography with elution system C to obtain the title product 5f (555 mg, yellow), yield: 87.0%.

MS m/z (ESI): 385.3 [M+1].

Step 6

1-(1-(5-(Ethoxymethyl)-4-(6-methoxypyridin-3-yl)-4H-1,2,4-triazol-3-yl)azetidin-3-yl)-5-fluoro-3-methyl-1H-indole 5

Compound 5f (85 mg, 0.22 mmol), 2-ethoxyacetylhydrazine (26.12 mg, 0.22 mmol) and three drops of trifluoroacetic acid were dissolved in 10 mL of tetrahydrofuran successively. After addition, the reaction solution was heated to 70° C. and reacted for 3 hours. The reaction solution was concentrated under reduced pressure to remove the solvent, and the resulting residues were purified by thin layer chromatography with developing solvent system A to obtain the title product 5 (60 mg, yellow oil), yield: 62.2%.

MS m/z (ESI): 437.5 [M+1].

$^1$H NMR (400 MHz, CD$_3$OD) δ 8.34 (d, 1H), 7.86 (d, 1H), 7.36 (d, 1H), 7.32 (s, 1H), 7.17 (d, 1H), 7.15 (d, 1H), 6.97 (t, 1H), 5.31-5.41 (m, 1H), 4.40 (s, 2H), 4.33 (t, 2H), 4.13 (d, 2H), 3.98 (s, 3H), 3.41-3.45 (m, 2H), 2.27 (s, 3H), 1.10 (t, 3H).

Example 6

5-Fluoro-1-(1-(4-(6-methoxypyridin-3-yl)-5-methyl-4H-1,2,4-triazol-3-yl)azetidin-3-yl)-3-methyl-1H-indole 6

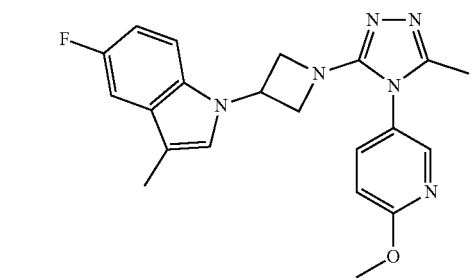

6

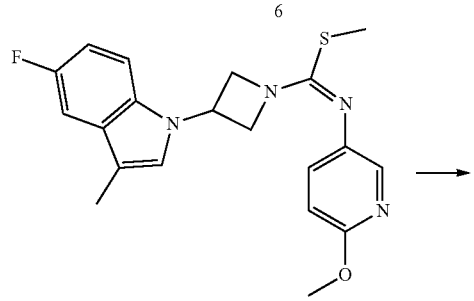

5f

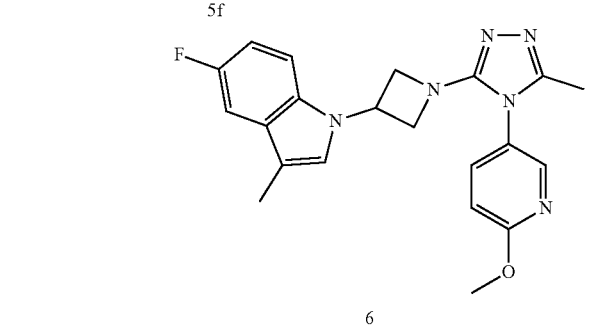

6

Compound 5f (75 mg, 0.20 mmol), acetylhydrazine (14.45 mg, 0.2 mmol) and three drops of trifluoroacetic acid were dissolved in 10 mL of tetrahydrofuran successively. After addition, the reaction solution was heated to 70° C. and reacted for 3 hours. The reaction solution was concentrated under reduced pressure to remove the solvent, and the resulting residues were purified by thin layer chromatography with developing solvent system A to obtain the title product 6 (12 mg, white solid), yield: 15.7%.

MS m/z (ESI): 393.1 [M+1].

$^1$H NMR (400 MHz, CD$_3$OD) δ 8.31 (d, 1H), 7.82 (d, 1H), 7.36 (d, 1H), 7.30 (s, 1H), 7.15 (d, 1H), 7.00 (d, 1H), 6.91 (t, 1H), 5.30-5.41 (m, 1H), 4.29 (t, 2H), 4.10 (d, 2H), 3.98 (s, 3H), 2.27 (s, 3H), 2.22 (t, 3H).

Example 7

5-Fluoro-1-(1-(5-(methoxymethyl)-4-(6-methoxypyridin-3-yl)-4H-1,2,4-triazol-3-yl)azetidin-3-yl)-3-(trifluoromethyl)-1H-indole 7

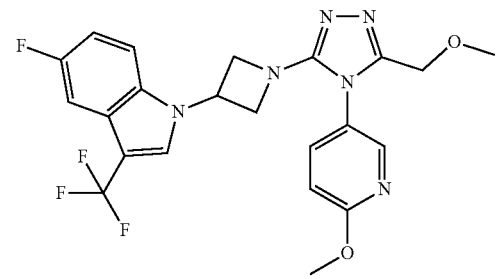

7

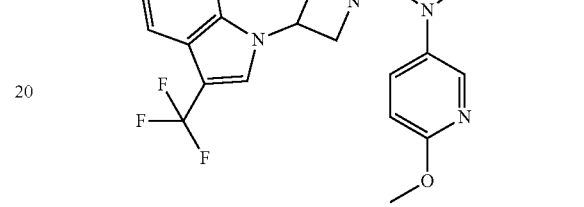

3d

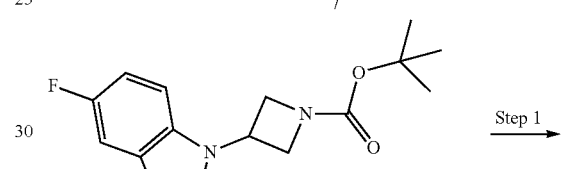

7a

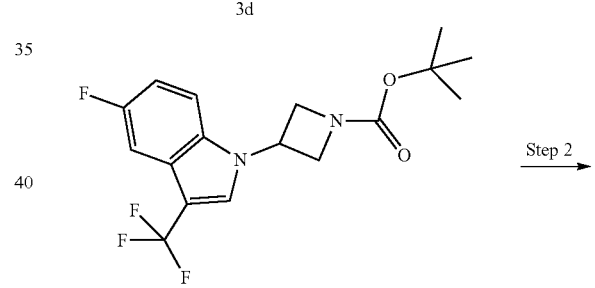

7b

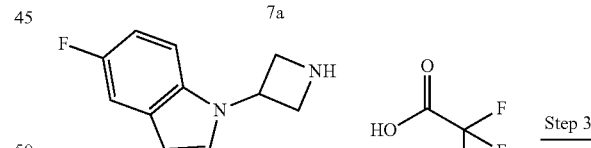

7c

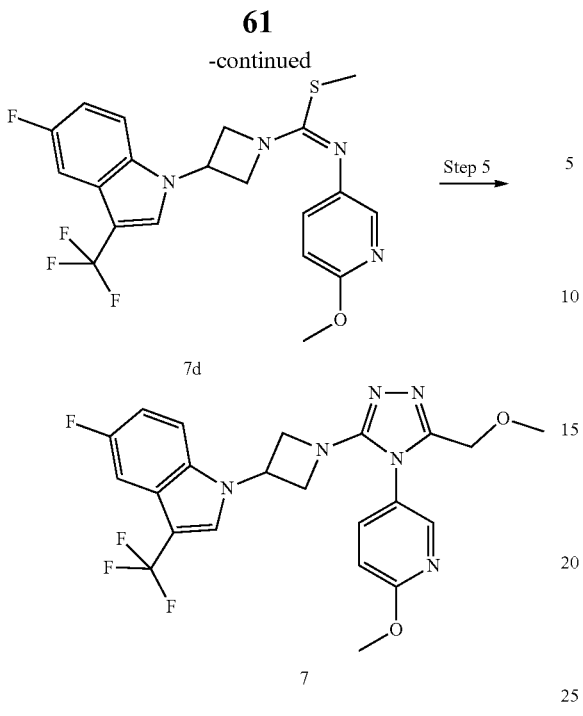

Step 1

Tert-butyl 3-(5-fluoro-3-(trifluoromethyl)-1H-indol-1-yl)azetidine-1-carboxylate 7a Compound 3d (110 mg, 0.38 mmol), cuprous thiophene-2-formate (7.22 mg, 0.04 mmol, prepared according to the known method disclosed in "*Chemistry—A European Journal,* 2013, 19(31), 10353-1035"), 1-(trifluoromethyl)-1,2-phenyliodo-3(1H)-one (178.47 mg, 0.57 mmol, prepared according to the known method disclosed in "*Angewandte Chemie, International Edition,* 2014, 53(52), 14559-14563") and 4,4,4',4',5,5,5',5'-octamethyl-2,2'-bis(1,3,2-dioxaborolane) (9.62 mg, 0.04 mmol) were added to 3 mL of chloroform. After addition, the reaction solution was reacted under argon atmosphere at 60° C. for 16 hours. The reaction solution was concentrated under reduced pressure, and the resulting residues were purified by thin layer chromatography with developing solvent system C to obtain the title product 7a (50 mg, yellow oil), yield: 33.1%.

MS m/z (ESI): 303.0 [M−55].

Step 2

1-(Azetidin-3-yl)-5-fluoro-3-(trifluoromethyl)-1H-indole 2,2,2-trifluoroacetate 7b Compound 7a (50 mg, 0.14 mmol) and trifluoroacetic acid (2 mL, 0.14 mmol) were added to 20 mL of dichloromethane, and reacted for 1 hour after addition. The reaction solution was concentrated under reduced pressure to remove the solvent to give the crude title product 7b (36 mg, yellow oil), which was used directly in the next step without purification.

MS m/z (ESI): 259.1 [M+1].

Step 3

3-(5-Fluoro-3-(trifluoromethyl)-1H-indol-1-yl)-N-(6-methoxypyridin-3-yl)azetidine-1-carbothioamide 7c The crude product 7b (80.1 mg, 0.31 mmol) and compound 1e (105.22 mg, 0.31 mmol) were dissolved in 10 mL of dichloromethane, and reacted for 2 hours after addition. The reaction solution was concentrated under reduced pressure to remove the organic solvent to give the crude title product 7c (135 mg, yellow oil), which was used directly in the next step without purification.

MS m/z (ESI): 425.1 [M+1].

Step 4

Methyl (E)-3-(5-fluoro-3-(trifluoromethyl)-1H-indol-1-yl)-N-(6-methoxypyridin-3-yl)azetidine-1-carbimidothioate 7d The crude product 7c (131.93 mg, 0.31 mmol) was dissolved in 10 mL of tetrahydrofuran, and cooled to 0° C. The above solution was added with potassium tert-butoxide (69.76 mg, 0.62 mmol), and reacted for 1 hour after addition. The above reaction solution was then added with methyl 4-methylbenzenesulfonate (69.47 mg, 0.37 mmol), and then slowly warmed up to room temperature, and reacted for 16 hours. The reaction solution was concentrated under reduced pressure to remove the organic solvent. The resulting residues were purified by thin layer chromatography with developing solvent system C to obtain the title product 7d (56 mg, yellow oil), yield: 41.1%.

MS m/z (ESI): 439.1 [M+1].

Step 5

5-Fluoro-1-(1-(5-(methoxymethyl)-4-(6-methoxypyridin-3-yl)-4H-1,2,4-triazol-3-yl) azetidin-3-yl)-3-(trifluoromethyl)-1H-indole 7

Compound 7d (20.42 mg, 0.050 mmol), trifluoroacetic acid (0.35 mg, 0.1 mmol) and 2-methoxyacetylhydrazine (9.7 mg, 0.09 mmol) were dissolved in 20 mL of tetrahydrofuran. After addition, the reaction solution was heated to 70° C. and reacted for 2 hours. The reaction solution was cooled to room temperature, and concentrated under reduced pressure. The resulting residues were purified by HPLC to obtain the title product 7 (20 mg, pale yellow oil), yield: 82.0%.

MS m/z (ESI): 477.2 [M+1].

$^1$H NMR (400 MHz, CDCl$_3$) δ 8.26-8.25 (m, 1H), 8.03-8.01 (m, 1H), 7.67-7.66 (m, 1H), 7.34-7.33 (m, 1H), 7.24-7.18 (m, 1H), 6.89-6.85 (m, 2H), 5.39-5.34 (m, 1H), 4.51-4.41 (m, 4H), 4.38 (s, 2H), 3.95 (s, 3H), 3.33 (s, 3H).

Example 8

Methyl 6-fluoro-3-(1-(5-(methoxymethyl)-4-(6-methoxypyridin-3-yl)-4H-1,2,4-triazol-3-yl) azetidin-3-yl)benzofuran-2-carboxylate 8

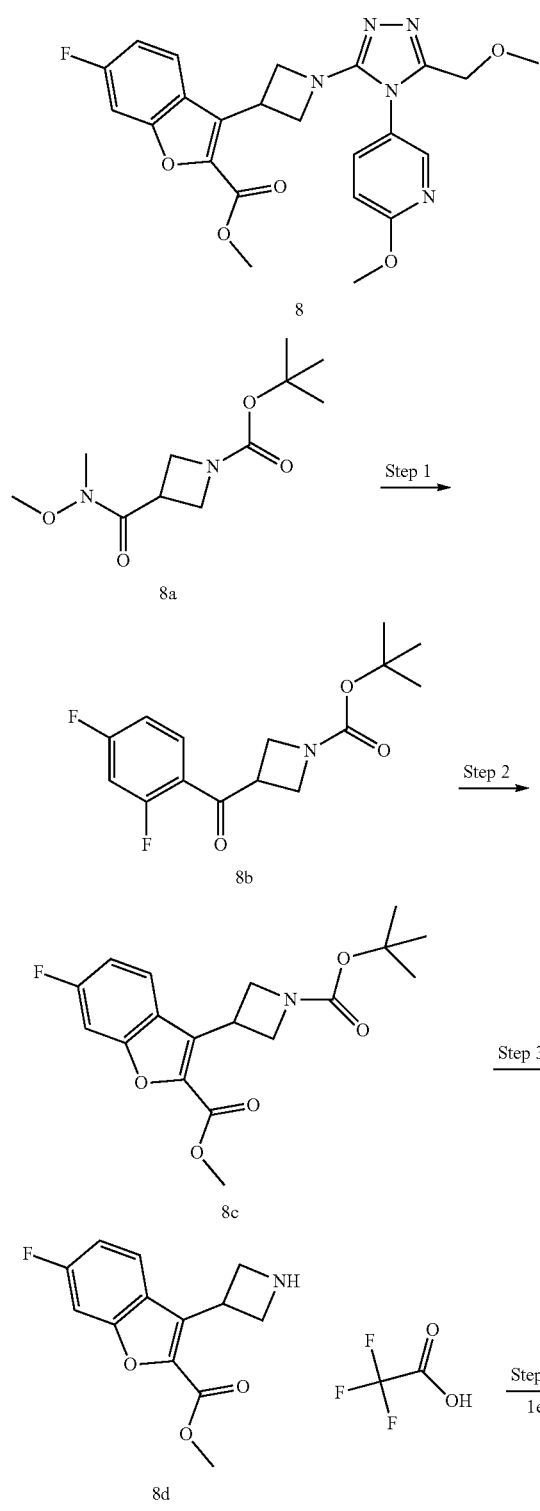

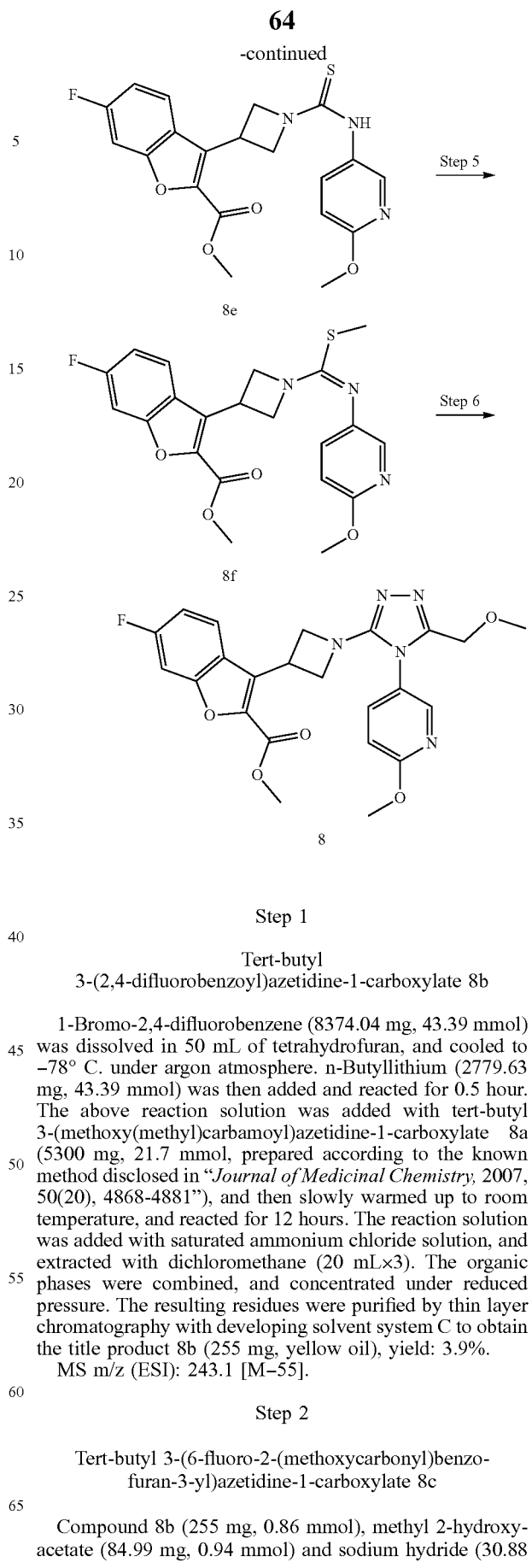

Step 1

Tert-butyl 3-(2,4-difluorobenzoyl)azetidine-1-carboxylate 8b

1-Bromo-2,4-difluorobenzene (8374.04 mg, 43.39 mmol) was dissolved in 50 mL of tetrahydrofuran, and cooled to −78° C. under argon atmosphere. n-Butyllithium (2779.63 mg, 43.39 mmol) was then added and reacted for 0.5 hour. The above reaction solution was added with tert-butyl 3-(methoxy(methyl)carbamoyl)azetidine-1-carboxylate 8a (5300 mg, 21.7 mmol, prepared according to the known method disclosed in "*Journal of Medicinal Chemistry*, 2007, 50(20), 4868-4881"), and then slowly warmed up to room temperature, and reacted for 12 hours. The reaction solution was added with saturated ammonium chloride solution, and extracted with dichloromethane (20 mL×3). The organic phases were combined, and concentrated under reduced pressure. The resulting residues were purified by thin layer chromatography with developing solvent system C to obtain the title product 8b (255 mg, yellow oil), yield: 3.9%.

MS m/z (ESI): 243.1 [M−55].

Step 2

Tert-butyl 3-(6-fluoro-2-(methoxycarbonyl)benzofuran-3-yl)azetidine-1-carboxylate 8c Compound 8b (255 mg, 0.86 mmol), methyl 2-hydroxyacetate (84.99 mg, 0.94 mmol) and sodium hydride (30.88 mg, 1.29 mmol) were dissolved in 50 mL of tetrahydrofuran. After addition, the reaction solution was heated to reflux and reacted for 3 hours. The reaction solution was added with 20 mL of ethyl acetate, washed with 40 mL of water, dried over anhydrous sodium sulfate, and filtered. The filtrate was concentrated under reduced pressure to remove the solvent, and the resulting residues were purified by thin layer chromatography with developing solvent system C to obtain the title product 8c (40 mg, yellow solid), yield: 13.4%.

MS m/z (ESI): 350.1 [M+1].

Step 3

Methyl 3-(azetidin-3-yl)-6-fluorobenzofuran-2-carboxylate Trifluoroacetate 8d

Compound 8c (200 mg, 0.65 mmol) and 2 mL of trifluoroacetic acid were mixed and reacted at 30° C. for 2 hours. The reaction solution was filtered and concentrated under reduced pressure to obtain the crude title product 8d (21 mg, yellow oil), which was used directly in the next step without purification.

MS m/z (ESI): 250.1 [M+1].

Step 4

Methyl 6-fluoro-3-(1-(((6-methoxypyridin-3-yl)carbamothioyl)azetidin-3-yl)benzofuran-2-carboxylate 8e Compound 1e (160.37 mg, 0.96 mmol) and the crude product 8d (21 mg, 0.080 mmol) were dissolved in 10 mL of tetrahydrofuran, and reacted for 16 hours after addition. The resulting reaction solution containing the title product 8e was used directly in the next step without purification.

MS m/z (ESI): 416.1 [M+1].

Step 5

Methyl (E)-6-fluoro-3-(1-(((6-methoxypyridin-3-yl)imino)(methylthio)methyl)azetidin-3-yl) benzofuran-2-carboxylate 8f The crude product 8e (35 mg, 0.08 mmol) and methyl 4-methylbenzenesulfonate (15.69 mg, 0.08 mmol) were dissolved in 10 mL of tetrahydrofuran, and reacted for 0.5 hour. The reaction solution was then added with potassium tert-butoxide (28.36 mg, 0.25 mmol), and reacted for 16 hours after addition. The reaction solution was added with 10 mL of water, and extracted with dichloromethane (10 mL×3). The organic phases were combined, dried over anhydrous sodium sulfate, and filtered. The filtrate was concentrated under reduced pressure to remove the solvent, and the resulting residues were purified by thin layer chromatography with developing solvent system C to obtain the title product 8f (20 mg, pale yellow solid), yield: 49.7%.

MS m/z (ESI): 430.1 [M+1].

Step 6

Methyl 6-fluoro-3-(1-(5-(methoxymethyl)-4-(6-methoxypyridin-3-yl)-4H-1,2,4-triazol-3-yl) azetidin-3-yl)benzofuran-2-carboxylate 8

Compound 8f (100 mg, 0.26 mmol), trifluoroacetic acid (0.53 mg, 0.1 mmol) and 2-methoxyacetylhydrazine (9.7 mg, 0.09 mmol) were dissolved in 20 mL of tetrahydrofuran. After addition, the reaction solution was reacted at 70° C. for 2 hours. The reaction solution was cooled to room temperature, and concentrated under reduced pressure to remove the solvent. The resulting residues were purified by HPLC to obtain the title product 8 (20 mg, pale yellow oil), yield: 91.9%.

MS m/z (ESI): 468.2[M+1].

$^1$H NMR (400 MHz, CDCl$_3$) δ 8.25-8.24 (m, 1H), 8.04-8.02 (m, 1H), 7.65-7.62 (m, 1H), 7.29-7.27 (m, 1H), 7.13-7.11 (m, 1H), 6.86-6.84 (m, 1H), 4.88-4.83 (m, 1H), 4.37-4.33 (m, 4H), 4.12-4.08 (m, 2H), 3.96 (s, 3H), 3.93 (s, 3H), 3.31 (s, 3H).

Example 9

5-(3-(3-(6-Fluorobenzo[b]thiophen-3-yl)azetidin-1-yl)-5-(methoxymethyl)-4H-1,2,4-triazol-4-yl)-2-methoxypyridine 9

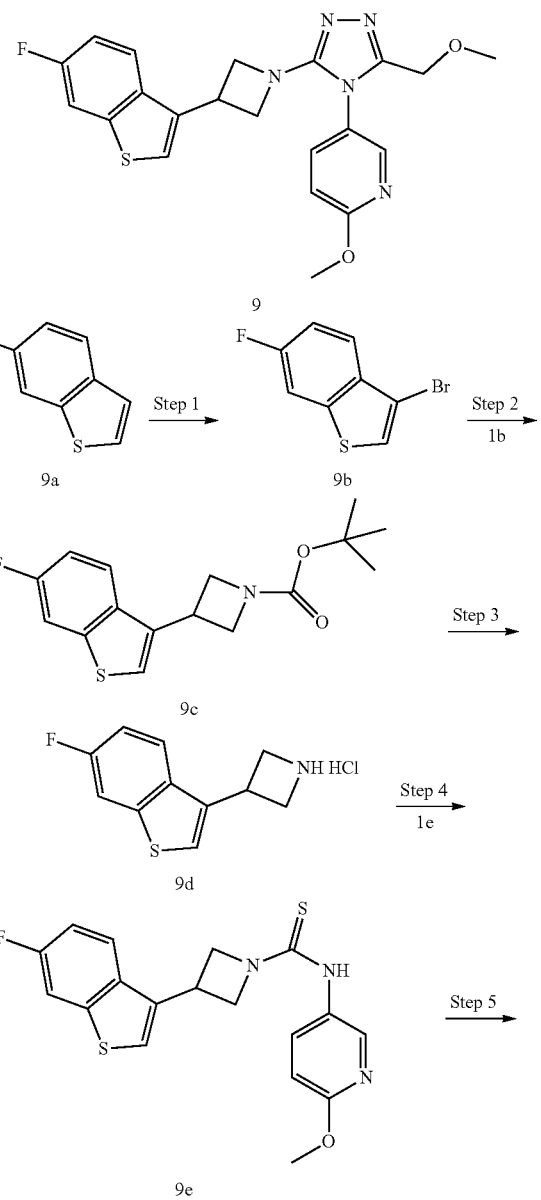

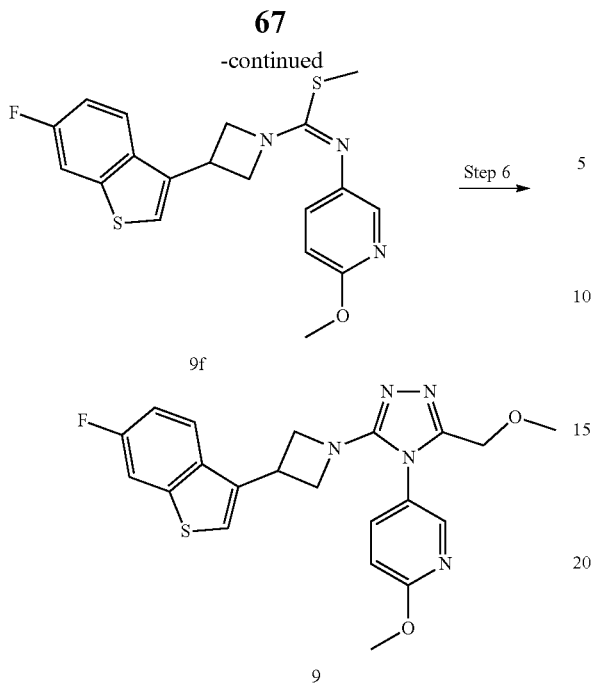

Step 1

3-Bromo-6-fluorobenzo[b]thiophene 9b

6-Fluorobenzothiophene 9a (500 mg, 3.29 mmol) and N-bromosuccinimide (584.73 mg, 3.29 mmol) were dissolved in 10 mL of N,N-dimethylformamide, and reacted for 16 hours after addition. The reaction solution was concentrated under reduced pressure, and the resulting residues were purified by thin layer chromatography with developing solvent system C to obtain the title product 9b (200 mg, colorless oil), yield: 23.4%.

Step 2

Tert-butyl 3-(6-fluorobenzo[b]thiophen-3-yl)azetidine-1-carboxylate 9c

Zinc (604.65 mg, 9.25 mmol), iodine (109.84 mg, 0.43 mmol) and compound 1b (245.03 mg, 0.87 mmol) were added to 30 mL of N,N-dimethylformamide, and reacted under argon atmosphere for 1 hour after addition. The above reaction solution was then added with compound 9b (200 mg, 0.87 mmol), bis(dibenzylideneacetone)palladium (792.56 mg, 0.87 mmol) and 2-dicyclohexylphosphine-2',4',6'-triisopropylbiphenyl (412.6 mg, 0.87 mmol). After addition, the reaction solution was heated at 50° C. for 3 hours. The reaction solution was cooled to room temperature, and filtered. The filtrate was collected, and concentrated under reduced pressure to remove the solvent. The resulting residues were purified by thin layer chromatography with developing solvent system C to obtain the title product 9c (100 mg, black oil), yield: 37.0%.

MS m/z (ESI): 308.4 [M+1].

Step 3

3-(6-Fluorobenzo[b]thiophen-3-yl)azetidine Hydrochloride 9d

Compound 9c (200 mg, 0.65 mmol) and 1.63 mL solution of hydrogen chloride in 1,4-dioxane (4 M) were dissolved in 5 mL of dichloromethane successively, and the reaction solution was stirred for 3 hours. The above reaction solution was concentrated under reduced pressure to remove the solvent to give the crude title product 9d (200 mg, yellow solid), which was used directly in the next step without purification.

MS m/z (ESI): 208.4 [M+1].

Step 4

3-(6-Fluorobenzo[b]thiophen-3-yl)-N-(6-methoxypyridin-3-yl)azetidine-1-carbothioamide 9e Compound 1e (160.37 mg, 0.96 mmol) and the crude product 9d (200 mg, 0.96 mmol) were dissolved in 20 mL of tetrahydrofuran, and reacted for 3 hours after addition. The resulting reaction solution containing the title product 9e was used directly in the next step without purification.

MS m/z (ESI): 374.2 [M+1].

Step 5

Methyl (E)-3-(6-fluorobenzo[b]thiophen-3-yl)-N-(6-methoxypyridin-3-yl)azetidine-1-carbimidothioate 9f The crude product 9e (200 mg, 0.54 mmol), potassium tert-butoxide (60.91 mg, 0.54 mmol) and methyl 4-methylbenzenesulfonate (101.09 mg, 0.54 mmol) were dissolved in 20 mL of tetrahydrofuran, and reacted for 16 hours after addition. The reaction solution was concentrated under reduced pressure, and the resulting residues were purified by thin layer chromatography with developing solvent system C to obtain the title product 9f (100 mg, colorless oil), yield: 38.6%.

MS m/z (ESI): 388.2 [M+1].

Step 6

5-(3-(3-(6-Fluorobenzo[b]thiophen-3-yl)azetidin-1-yl)-5-(methoxymethyl)-4H-1,2,4-triazol-4-yl)-2-methoxypyridine 9

Compound 9f (100 mg, 0.26 mmol), trifluoroacetic acid (58.85 mg, 0.52 mmol) and 2-methoxyacetylhydrazine (53.74 mg, 0.52 mmol) were dissolved in 20 mL of tetrahydrofuran. After addition, the reaction solution was reacted at 65° C. for 3 hours. The reaction solution was cooled to room temperature, and concentrated under reduced pressure to remove the solvent. The resulting residues were purified by HPLC to obtain the title product 9 (15 mg, brown paste), yield: 13.1%.

MS m/z (ESI): 426.4 [M+1].

$^1$H NMR (400 MHz, CD$_3$OD) δ 8.42 (d, 1H), 7.93-7.90 (m, 1H), 7.68-7.65 (m, 2H), 7.52 (s, 1H), 7.22-7.18 (m, 1H), 7.04-7.00 (m, 1H), 4.51-4.42 (m, 3H), 4.36 (s, 2H), 4.24-4.18 (m, 2H), 4.01 (s, 3H), 3.29 (s, 3H).

Example 10

3-Chloro-5-fluoro-1-(1-(5-(methoxymethyl)-4-(6-methoxypyridin-3-yl)-4H-1,2,4-triazol-3-yl)azetidin-3-yl)-1H-indole 10

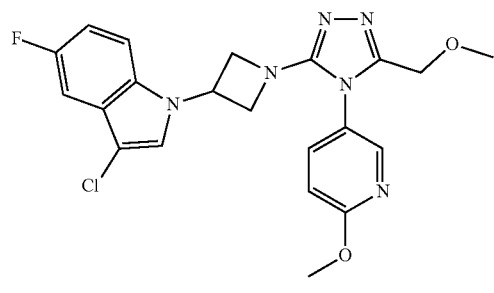

Compound 4b (56 mg, 0.14 mmol), 2-methoxyacetylhydrazine (14.4 mg, 0.14 mmol) and three drops of trifluoroacetic acid were dissolved in 10 mL of tetrahydrofuran successively. After addition, the reaction solution was heated to 70° C. and reacted for 3 hours. The reaction solution was concentrated under reduced pressure to remove the solvent, and the resulting residues were purified by thin layer chromatography with developing solvent system A to obtain the title product 10 (20 mg, white solid), yield: 31.9%.

MS m/z (ESI): 443.1 [M+1].

$^1$H NMR (400 MHz, CD$_3$OD) δ 8.34 (d, 1H), 7.85 (d, 1H), 7.66 (s, 1H), 7.50 (d, 1H), 7.19 (d, 1H), 7.03 (t, 1H), 6.98 (d, 1H), 5.35-5.45 (m, 1H), 4.34-4.39 (m, 4H), 4.14 (d, 2H), 3.98 (s, 3H), 3.27 (s, 3H).

Example 11

5-(3-(3-(6-Fluorobenzofuran-3-yl)azetidin-1-yl)-5-(methoxymethyl)-4H-1,2,4-triazol-4-yl)-2-methoxypyridine 11

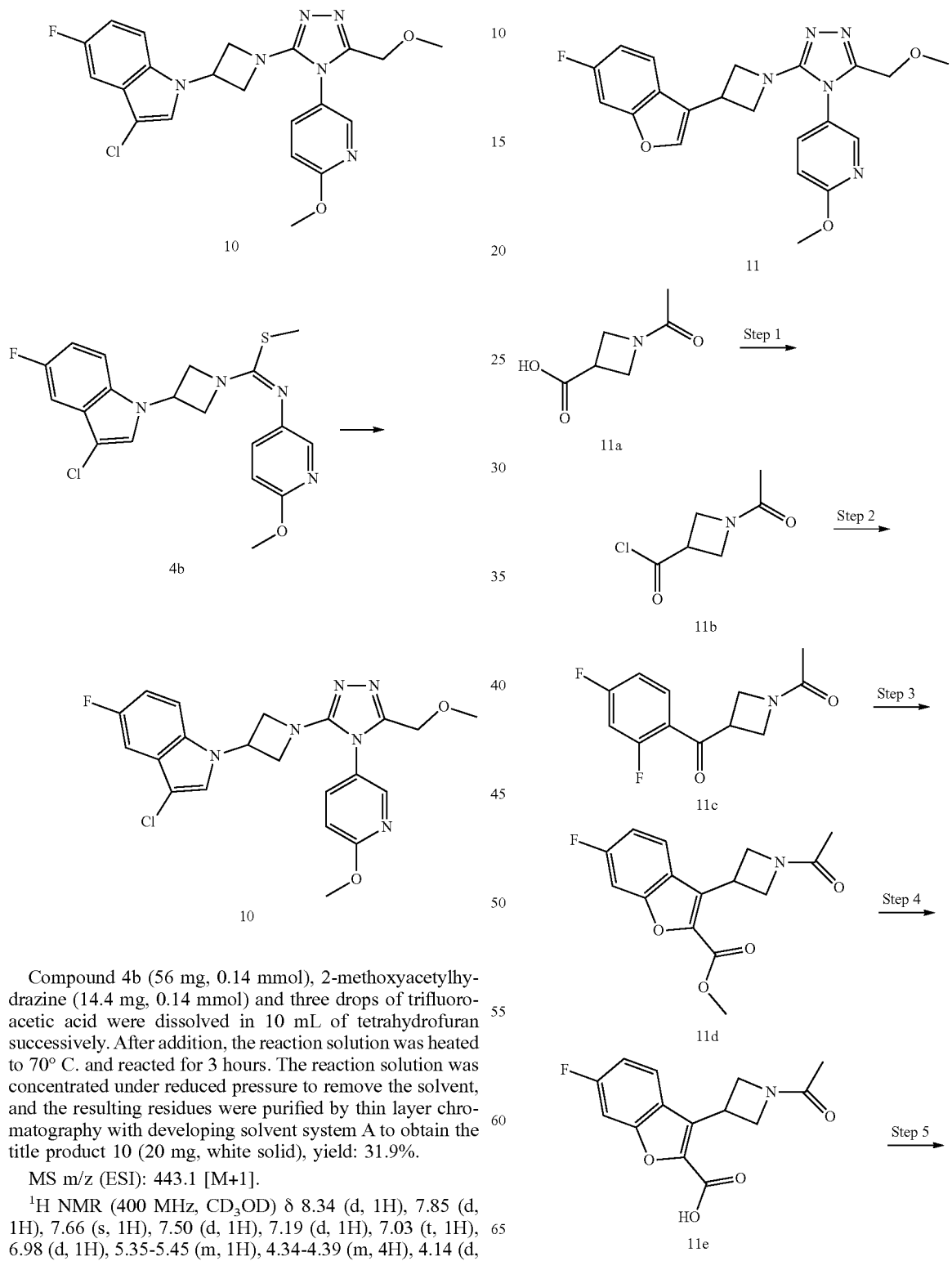

-continued

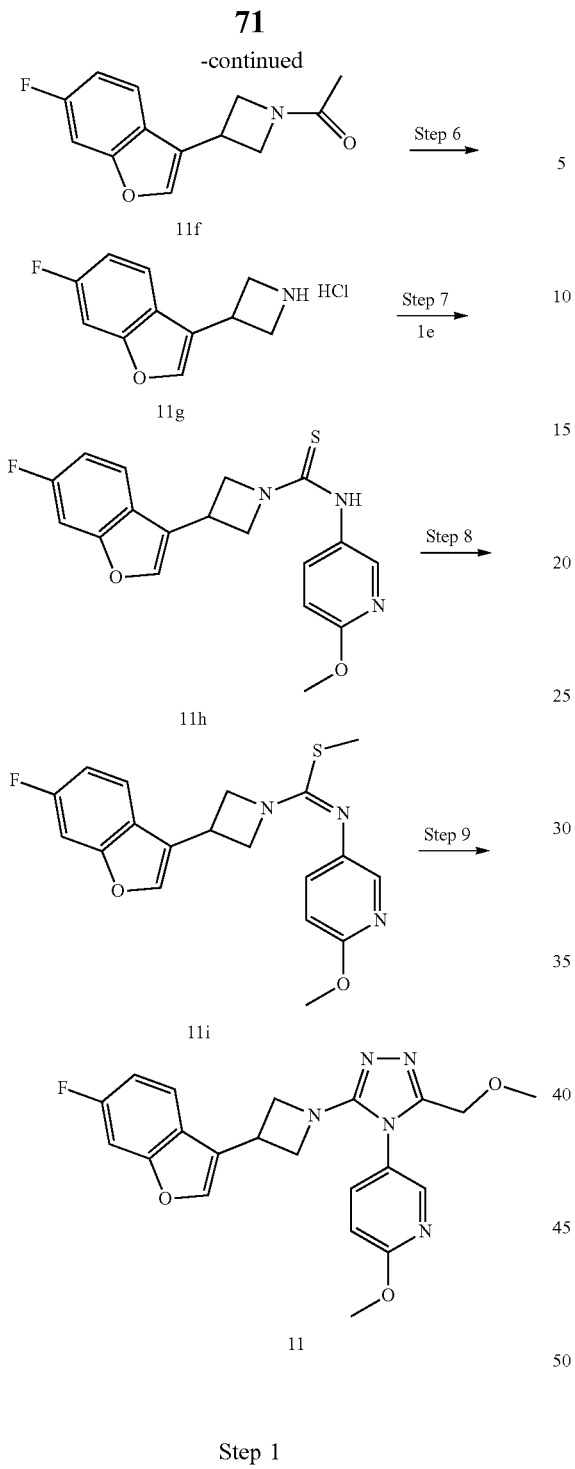

Step 1

1-Acetylazetidine-3-carbonyl chloride 11b

1-Acetylazetidine-3-carboxylic acid 11a (1500 mg, 10.48 mmol) was dissolved in 20 mL of dichloromethane, and cooled to 0° C. The above solution was then added with oxalyl chloride (1995.2 mg, 15.72 mmol), and reacted at room temperature for 1.5 hours. The reaction solution was concentrated under reduced pressure to remove the organic solvent to give the crude title product 11b (1600 mg, yellow solid), which was used directly in the next step without purification.

Step 2

1-(3-(2,4-Difluorobenzoyl)azetidin-1-yl)ethanone 11c

Aluminum trichloride (3465.73 mg, 25.99 mmol), the crude product 11b (2.1 g, 13 mmol) and 1,3-difluorobenzene were dissolved in 40 mL of dichloromethane, and reacted under reflux for 3 hours after addition. The reaction solution was poured into a mixture of ice water and hydrochloric acid (V:V=1:1), and extracted with dichloromethane (20 mL×3). The organic phases were combined, dried over anhydrous sodium sulfate, and filtered. The filtrate was concentrated under reduced pressure to remove the organic solvent to give the crude title product 11c (300 mg, yellow oil), which was used directly in the next step without purification.

MS m/z (ESI): 240.1 [M+1].

Step 3

Methyl 3-(1-acetylazetidin-3-yl)-6-fluorobenzofuran-2-carboxylate 11d

The crude product 11c (140 mg, 0.59 mmol) and methyl 2-hydroxyacetate (65.33 mg, 0.73 mmol) were dissolved in 200 mL of tetrahydrofuran. The reaction solution was then added with sodium hydride (20.18 mg, 0.88 mmol), and reacted under reflux for 3 hours. The reaction solution was concentrated under reduced pressure to remove tetrahydrofuran. The residues were dissolved in 200 mL of ethyl acetate, washed with water (100 mL×2) and saturated sodium chloride solution (100 mL×1) respectively, dried over anhydrous magnesium sulfate, and filtered. The filtrate was concentrated under reduced pressure to remove the organic solvent, and the resulting residues were purified by the CombiFlash rapid preparation instrument with elution system C to obtain the title product 11d (200 mg, yellow oil), yield: 100%.

MS m/z (ESI): 292.1 [M+1].

Step 4

3-(1-Acetylazetidin-3-yl)-6-fluorobenzofuran-2-carboxylic acid 11e

Compound 11d (200 mg, 0.69 mmol) and lithium hydroxide hydrate (86.44 mg, 20.6 mmol) were dissolved in 20 mL of a mixed solution of water and tetrahydrofuran (V:V=1:1), and reacted for 2 hours. The reaction solution was concentrated under reduced pressure. The residues were dissolved in 200 mL of ethyl acetate, washed with water (100 mL×2) and saturated sodium chloride solution (100 mL) respectively, dried over magnesium sulfate, and filtered. The filtrate was concentrated under reduced pressure, and the resulting residues were purified by the CombiFlash rapid preparation instrument with elution system C to obtain the title product 11e (100 mg, yellow oil), yield: 52.5%.

MS m/z (ESI): 278.1 [M+1].

Step 5

1-(3-(6-Fluorobenzofuran-3-yl)azetidin-1-yl)ethanone 11f

Compound 11e (30 mg, 0.11 mmol), quinoline (5 g, 38.71 mmol) and copper (20.63 mg, 0.32 mmol) were mixed, and reacted at 200° C. for 10 minutes. The reaction solution was filtered, and the filtrate was added with 1 N hydrochloric acid (20 mL) and dichloromethane (20 mL×3). The organic phases were combined, dried over anhydrous sodium sulfate, and filtered. The filtrate was concentrated under reduced pressure to remove the organic solvent, and the resulting residues were purified by thin layer chromatography with developing solvent system C to obtain the title product 11f (100 mg, yellow oil), yield: 100%.

MS m/z (ESI): 234.1 [M+1].

Step 6

3-(6-Fluorobenzofuran-3-yl)azetidine hydrochloride 11g

Compound 11f (20 mg, 0.09 mmol) and 10 mL of hydrochloric acid (12 M) were dissolved in 3 mL of ethanol, and reacted at 60° C. for 12 hours. The reaction solution was concentrated under reduced pressure until dryness. The residues were added dropwise with 12 M hydrochloric acid to adjust the pH to acidic, and filtered. The filter cake was collected to obtain the crude title product 11g (100 mg, white solid), which was used directly in the next step without purification.

MS m/z (ESI): 192.2 [M+1].

Step 7

3-(6-Fluorobenzofuran-3-yl)-N-(6-methoxypyridin-3-yl)azetidine-1-carbothioamide 11h The crude product 11g (30 mg, 0.16 mmol) and compound 1e (26.1 mg, 0.16 mmol) were dissolved in 10 mL of tetrahydrofuran, and reacted for 12 hours after addition. The reaction solution containing the title product 11h was used directly in the next step without purification.

Step 8

Methyl (E)-3-(6-fluorobenzofuran-3-yl)-N-(6-methoxypyridin-3-yl)azetidine-1-carbimidothioate 11i The crude product 11h (56 mg, 0.16 mmol) and methyl 4-methylbenzenesulfonate (58.36 mg, 0.31 mmol) were dissolved in 10 mL of tetrahydrofuran, and reacted for 0.5 hour. The reaction solution was then added with potassium tert-butoxide (35.16 mg, 0.31 mmol), and reacted for 12 hours after addition. The reaction solution was added with 20 mL of water, and extracted with ethyl acetate (20 mL×3). The organic phases were combined, dried over anhydrous sodium sulfate, and filtered. The filtrate was concentrated under reduced pressure to remove the solvent, and the resulting residues were purified by thin layer chromatography with developing solvent system A to obtain the title product 11i (40 mg, pale yellow solid), yield: 61.9%.

MS m/z (ESI): 372.1 [M+1].

Step 9

5-(3-(3-(6-Fluorobenzofuran-3-yl)azetidin-1-yl)-5-(methoxymethyl)-4H-1,2,4-triazol-4-yl)-2-methoxypyridine 11

Compound 11i (40 mg, 0.11 mmol), trifluoroacetic acid (1.23 mg, 0.01 mmol) and 2-methoxyacetylhydrazine (22.42 mg, 0.22 mmol) were dissolved in 20 mL of tetrahydrofuran. After addition, the reaction solution was reacted at 70° C. for 2 hours. The reaction solution was cooled to room temperature, and concentrated under reduced pressure to remove the solvent. The resulting residues were purified by HPLC to obtain the title product 11 (20 mg, pale yellow oil), yield: 45.4%.

MS m/z (ESI): 410.2 [M+1].

$^1$H NMR (400 MHz, CDCl$_3$) δ 8.23-8.22 (m, 1H), 7.63-7.62 (m, 1H), 7.61-7.60 (m, 1H), 7.53 (s, 1H) 7.24-7.14 (m, 1H), 7.07-6.95 (m, 1H), 6.86-6.84 (m, 1H), 4.34 (s, 2H), 4.25-4.21 (m, 2H), 4.03-3.85. (m, 6H), 3.31 (s, 3H).

Example 12

6-Fluoro-3-(1-(5-(methoxymethyl)-4-(6-methoxypyridin-3-yl)-4H-1,2,4-triazol-3-yl) azetidin-3-yl)benzo[d]isoxazole 12

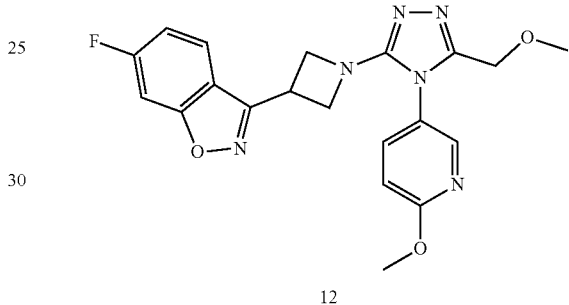

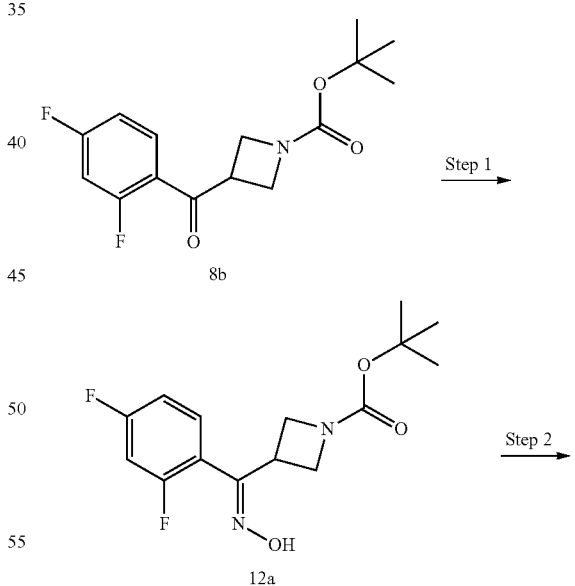

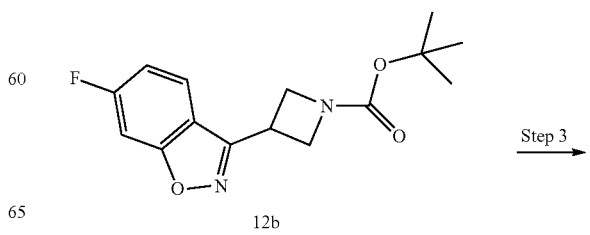

-continued

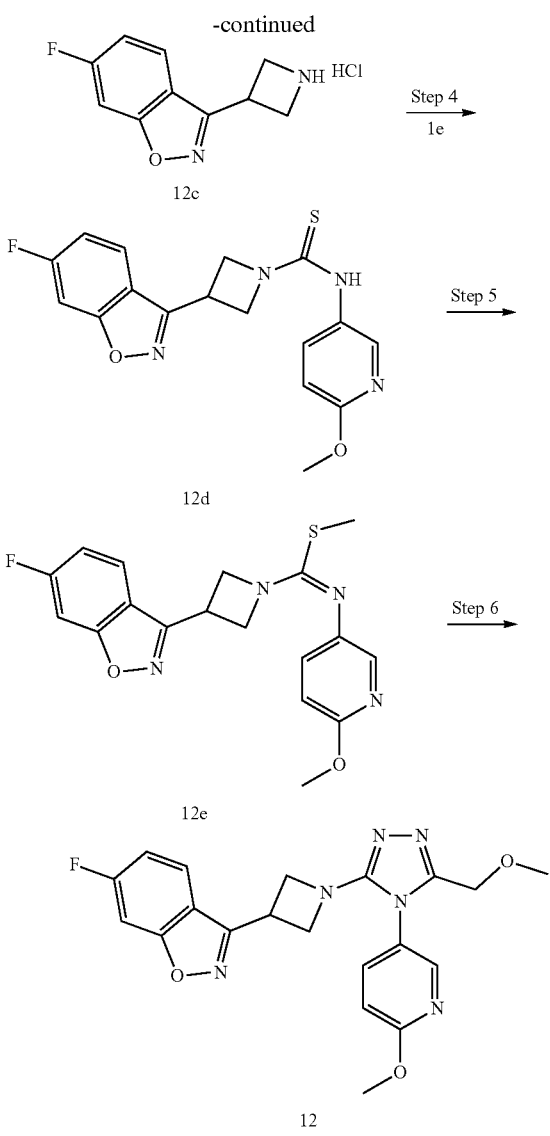

Step 1

Tert-butyl (E)-3-((2,4-difluorophenyl)(hydroxyimino)methyl)azetidine-1-carboxylate 12a Compound 8b (300 mg, 1.01 mmol), hydroxylamine hydrochloride (140.24 mg, 2.02 mmol) and sodium acetate (206.94 mg, 2.52 mmol) were dissolved in 12 mL of ethanol successively, and reacted for 12 hours. The reaction solution was concentrated under reduced pressure to remove the organic solvent, and the resulting residues were purified by thin layer chromatography with developing solvent system C to obtain the title product 12a (110 mg, pale yellow solid), yield: 34.9%.

MS m/z (ESI): 313.2 [M+1].

Step 2

Tert-butyl 3-(6-fluorobenzo[d]isoxazol-3-yl)azetidine-1-carboxylate 12b

Compound 12a (110 mg, 0.35 mmol) and potassium tert-butoxide (59.28 mg, 0.53 mmol) were added to 10 mL of tetrahydrofuran successively, and heated to 60° C. to react for 12 hours. The reaction solution was cooled to room temperature, and concentrated under reduced pressure. The resulting residues were purified by thin layer chromatography with developing solvent system C to obtain the title product 12b (40 mg, yellow oil), yield: 38.8%.

MS m/z (ESI): 293.1 [M+1].

Step 3

3-(Azetidin-3-yl)-6-fluorobenzo[d]isoxazole Hydrochloride 12c

Compound 12b (40 mg, 0.14 mmol) and 0.34 mL solution of hydrogen chloride in 1,4-dioxane (4 M) were added to 10 mL of dichloromethane successively, and reacted for 2 hour. The reaction solution was concentrated under reduced pressure to remove the organic solvent to give the crude title product 12c (32 mg, white solid), which was used directly in the next step without purification.

MS m/z (ESI): 193.3 [M+1].

Step 4

3-(6-Fluorobenzo[d]isoxazol-3-yl)-N-(6-methoxypyridin-3-yl)azetidine-1-carbothioamide 12d Compound 1e (47.47 mg, 0.14 mmol) and the crude product 12c (32 mg, 0.14 mmol) were dissolved in 10 mL of tetrahydrofuran, and reacted for 12 hours after addition. The above reaction solution was concentrated under reduced pressure to obtain the crude title product 12d (35 mg, yellow solid), which was used directly in the next step without purification.

MS m/z (ESI): 359.1 [M+1].

Step 5

Methyl (E)-3-(6-fluorobenzo[d]isoxazol-3-yl)-N-(6-methoxypyridin-3-yl)azetidine-1-carbimidothioate 12e The crude product 12d (80 mg, 0.14 mmol) was dissolved in 15 mL of tetrahydrofuran, and cooled to 0° C. in an ice bath. The above solution was then added with potassium tert-butoxide (31.31 mg, 0.28 mmol), and reacted at 0° C. for 1 hour after addition. The above solution was added with methyl 4-methylbenzenesulfonate (3.78 mg, 0.18 mmol), and then slowly warmed up to room temperature, and reacted for 12 hours. The reaction solution was concentrated under reduced pressure to remove the solvent. The crude title product 12e (60 mg, yellow oil) was obtained, which was used directly in the next step without purification.

MS m/z (ESI): 373.1 [M+1].

Step 6

6-Fluoro-3-(1-(5-(methoxymethyl)-4-(6-methoxypyridin-3-yl)-4H-1,2,4-triazol-3-yl) azetidin-3-yl)benzo[d]isoxazole 12

The crude product 12e (60 mg, 0.16 mmol), 2-methoxyacetylhydrazine (16.77 mg, 0.16 mmol) and three drops of trifluoroacetic acid were dissolved in 15 mL of tetrahydrofuran successively. After addition, the reaction solution was heated to 70° C. and reacted for 3 hours. The reaction solution was cooled to room temperature, and concentrated under reduced pressure to remove the solvent. The resulting residues were purified by thin layer chromatography with developing solvent system A to obtain the title product 12 (10 mg, pale yellow oil), yield: 15.1%.

MS m/z (ESI): 411.2 [M+1].

$^1$H NMR (400 MHz, CD$_3$OD) δ 8.34 (d, 1H), 7.83-7.88 (m, 2H), 7.44 (d, 1H), 7.20 (d, 1H), 6.98 (d, 1H), 4.35-4.39 (m, 4H), 4.12 (d, 2H), 3.98 (s, 3H), 3.46 (s, 1H), 3.27 (s, 3H).

Example 13

5-Fluoro-1-(1-(5-(methoxymethyl)-4-(6-methoxy-pyridin-3-yl)-4H-1,2,4-triazol-3-yl) azetidin-3-yl)-1H-indole-3-carbonitrile 13

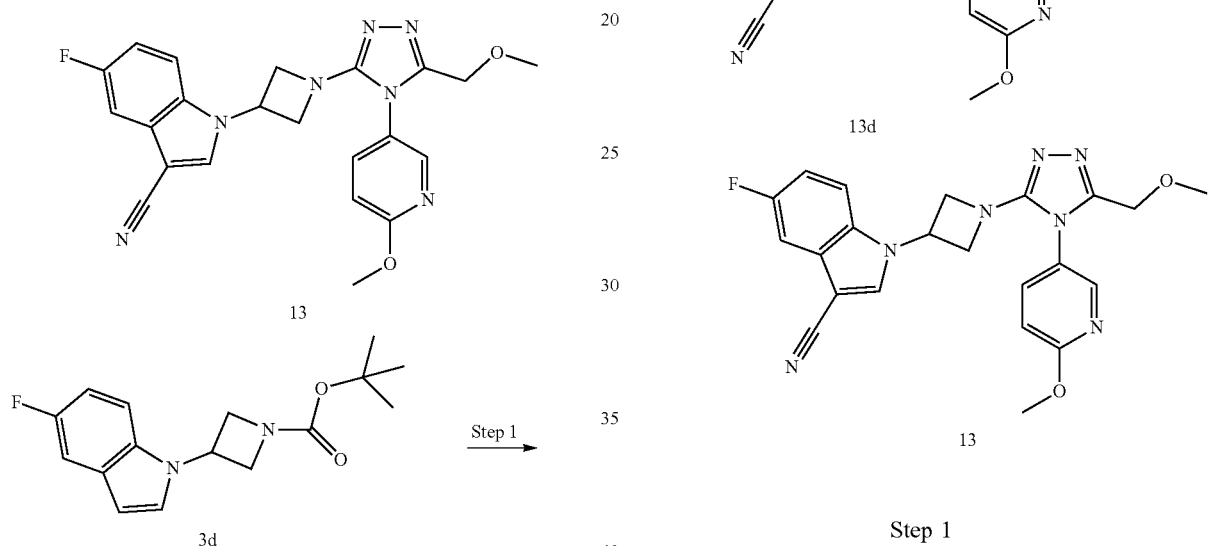

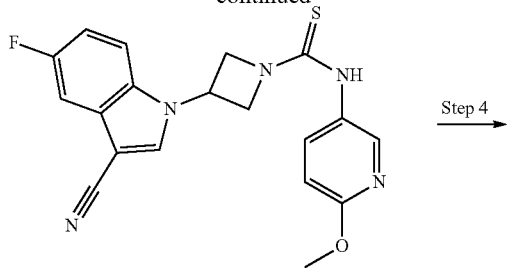

Step 1

Tert-butyl 3-(3-cyano-5-fluoro-1H-indol-1-yl)azetidine-1-carboxylate 13a

Compound 3d (300 mg, 1.03 mmol), phenylacetonitrile (242.1 mg, 2.07 mmol) and cuprous iodide (393.59 mg, 2.07 mmol) were dissolved in 20 mL of N,N-dimethylformamide, and reacted at 100° C. for 12 hours after addition. The reaction solution was concentrated under reduced pressure to remove the solvent, and the resulting residues were purified by thin layer chromatography with developing solvent system C to obtain the title product 13a (100 mg, yellow oil), yield: 30.7%.

MS m/z (ESI): 316.2 [M+1].

Step 2

1-(Azetidin-3-yl)-5-fluoro-1H-indole-3-carbonitrile Hydrochloride 13b

Compound 13a (100 mg, 0.32 mmol) was dissolved in 10 mL of dichloromethane. The above solution was then added with 0.79 mL solution of hydrogen chloride in 1,4-dioxane (4 M), and reacted for 3 hours. The reaction solution was concentrated under reduced pressure to obtain the crude title product 13b (215.23 mg, yellow solid), which was used directly in the next step without purification.

MS m/z (ESI): 216.2 [M+1].

Step 3

3-(3-Cyano-5-fluoro-1H-indol-1-yl)-N-(6-methoxy-pyridin-3-yl)azetidine-1-carbothioamide 13c The crude product 13b (100 mg, 0.46 mmol) and compound 1e (201.43 mg, 0.62 mmol) were dissolved in 10 mL of tetrahydrofuran, and reacted for 3 hours after addition. The reaction solution containing the title product 13c was used directly in the next step without purification.

MS m/z (ESI): 382.2 [M+1].

Step 4

Methyl (E)-3-(3-cyano-5-fluoro-1H-indol-1-yl)-N-(6-methoxypyridin-3-yl)azetidine-1-carbimidothioate 13d The crude product 13c (100 mg, 0.26 mmol), potassium tert-butoxide (88.25 mg, 0.79 mmol) and methyl 4-methylbenzenesulfonate (172.74 mg, 0.93 mmol) were dissolved in 20 mL of tetrahydrofuran, and reacted for 12 hours. The reaction solution was concentrated under reduced pressure to remove the organic solvent. The resulting residues were purified by thin layer chromatography with developing solvent system A to obtain the title product 13d (80 mg, yellow oil), yield: 38.9%.

MS m/z (ESI): 396.2 [M+1].

Step 5

5-Fluoro-1-(1-(5-(methoxymethyl)-4-(6-methoxy-pyridin-3-yl)-4H-1,2,4-triazol-3-yl) azetidin-3-yl)-1H-indole-3-carbonitrile 13

Compound 13d (50 mg, 0.13 mmol), trifluoroacetic acid (14.42 mg, 0.13 mmol) and 2-methylacetylhydrazine (19.75 mg, 0.19 mmol) were dissolved in 10 mL of tetrahydrofuran successively. After addition, the reaction solution was heated to 65° C. and reacted for 3 hours. The reaction solution was cooled to room temperature, and concentrated under reduced pressure to remove the solvent. The resulting residues were purified by HPLC to obtain the title product 13 (5 mg, white solid), yield: 8.2%.

MS m/z (ESI): 434.4 [M+1].

$^1$H NMR (400 MHz, CD$_3$OD) δ 8.35-8.33 (m, 2H), 7.87-7.84 (m, 1H), 7.64-7.60 (m, 1H), 7.36 (d, 1H), 7.18-7.14 (m, 1H), 7.04-7.00 (m, 1H), 4.61-4.59 (m, 3H), 4.46-4.40 (m, 2H), 4.20-4.16 (m, 2H), 3.98 (s, 3H), 3.26 (s, 3H).

Example 14

6-Fluoro-3-(1-(5-(methoxymethyl)-4-(6-methoxy-pyridin-3-yl)-4H-1,2,4-triazol-3-yl) azetidin-3-yl)-1-methyl-1H-indole 14

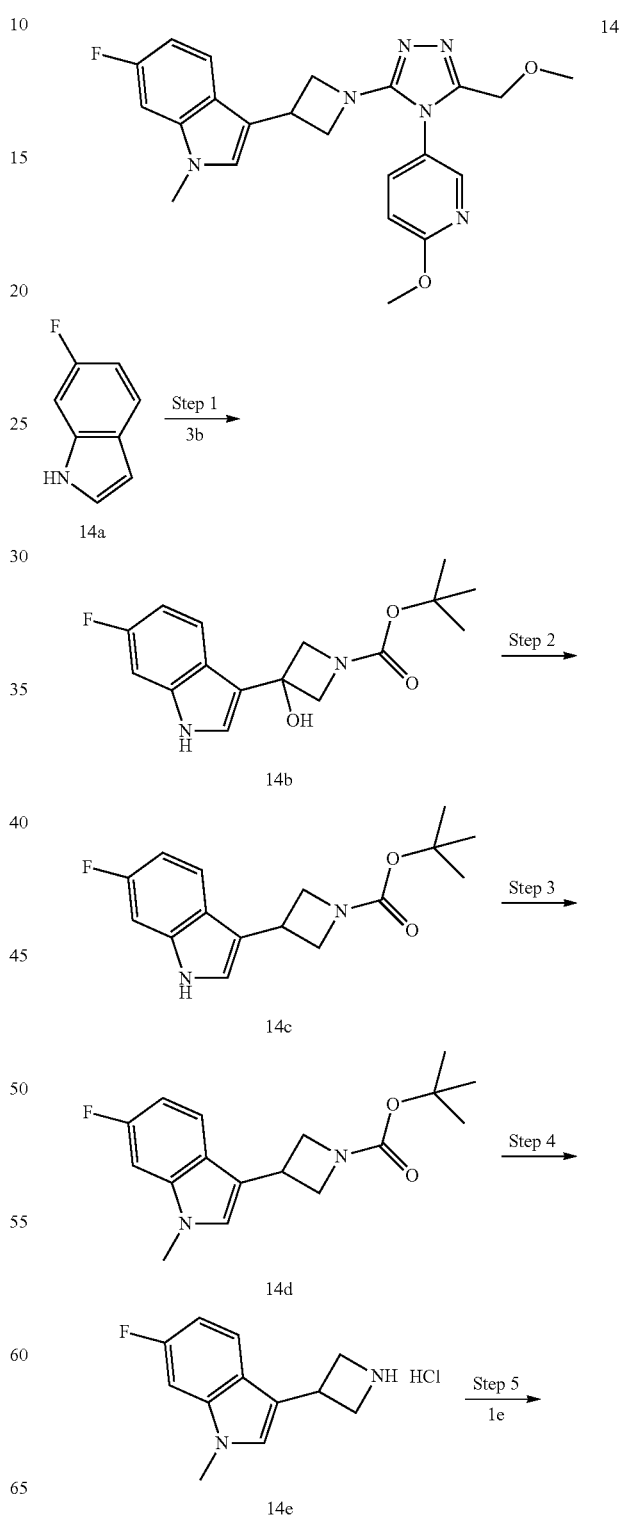

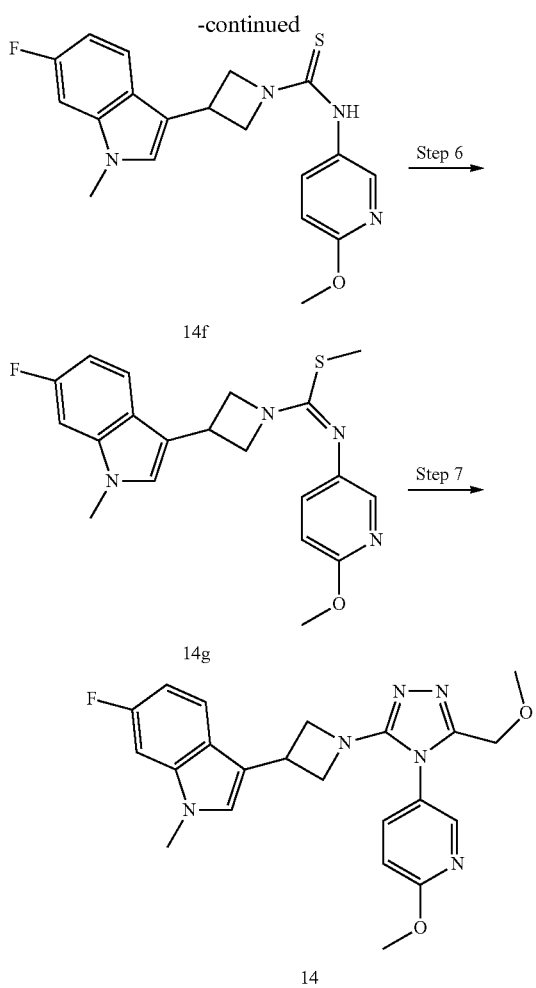

14f

14g

14

Step 1

Tert-butyl 3-(6-fluoro-1H-indol-3-yl)-3-hydroxy azetidine-1-carboxylate 14b

6-Fluoroindole 14a (1500 mg, 11.1 mmol) and potassium hydroxide (678.85 mg, 12.1 mmol) were dissolved in 30 mL of methanol, and stirred until potassium hydroxide dissolved. The above reaction solution was added with compound 3b (2071.15 mg, 12.10 mmol), and reacted at 50° C. after addition. The completion of the reaction was monitored by TLC. The reaction solution was cooled to room temperature, added with 100 mL of ethyl acetate, washed with water (50 mL×3) and saturated sodium chloride solution (50 mL×2) successively, dried over anhydrous sodium sulfate, and filtered. The filtrate was concentrated under reduced pressure, and the resulting residues were purified by thin layer chromatography with developing solvent system A to obtain the title product 14b (3300 mg, pale yellow oil), yield: 87.4%.

MS m/z (ESI): 307.2 [M+1].

Step 2

Tert-butyl 3-(6-fluoro-1H-indol-3-yl)azetidine-1-carboxylate 14c

Compound 14b (300 mg, 0.98 mmol) was dissolved in 2 mL of dichloromethane, and added with triethylsilane (1138.77 mg, 9.79 mmol) in an ice bath. When the reaction solution became turbid, it was added dropwise with trifluoroacetic acid (334.99 mg, 2.94 mmol) and reacted for 10 minutes. The reaction solution was added with 30 mL of saturated sodium bicarbonate solution to quench the reaction, and extracted with dichloromethane (30 mL×3). The organic phases were combined, washed with saturated sodium chloride solution (20 mL×2), dried over anhydrous sodium sulfate, and filtered. The filtrate was concentrated under reduced pressure to remove the organic solvent to give the crude title product 14c (290.33 mg, yellow oil), which was used directly in the next step without purification.

MS m/z (ESI): 291.2 [M+1].

Step 3

Tert-butyl 3-(6-fluoro-1-methyl-1H-indol-3-yl)azetidine-1-carboxylate 14d

The crude product 14c (300 mg, 1.03 mmol) was dissolved in 5 mL of N,N-dimethylformamide. The above solution was slowly added with sodium hydride (49.6 mg, 2.07 mmol) in portions at 0° C., and reacted for 0.5 hour. The reaction solution was then added with methyl iodide (220 mg, 1.55 mmol), and the reaction was monitored by LC-MS until the starting material was completely reacted. The reaction solution was added with 10 mL of water, stirred for 10 minutes, and extracted with ethyl acetate (20 mL×3). The organic phases were combined, dried over anhydrous sodium sulfate, and filtered. The filtrate was concentrated under reduced pressure to obtain the crude title product 14d (320 mg, yellow oil), which was used directly in the next step without purification.

MS m/z (ESI): 305.2 [M+1].

Step 4

3-(Azetidin-3-yl)-6-fluoro-1-methyl-1H-indole Hydrochloride 14e

The crude product 14d (140 mg, 0.46 mmol) and a solution of hydrogen chloride in 1,4-dioxane (1 mL, 4.60 mmol) were dissolved in 2.5 mL of dichloromethane, and reacted for 2 hours. The reaction was monitored by LC-MS until the starting material was completely reacted. The reaction solution was concentrated under reduced pressure to remove the solvent to give the crude title product 14e (100 mg, white solid), which was used directly in the next step without purification.

MS m/z (ESI): 205.3 [M+1].

Step 5

3-(6-Fluoro-1-methyl-1H-indol-3-yl)-N-(6-methoxypyridin-3-yl)azetidine-1-carbothioamide 14f The crude product 14e (100 mg, 0.49 mmol) and compound 1e (122.06 mg, 0.73 mmol) were dissolved in 5 mL of tetrahydrofuran, and reacted for 1.5 hours after addition. The reaction solution was concentrated under reduced pressure to obtain the crude title product 14f (180 mg, yellow oil), which was used directly in the next step without purification.

MS m/z (ESI): 371.4 [M+1].

Step 6

Methyl (E)-3-(6-fluoro-1-methyl-1H-indol-3-yl)-N-(6-methoxypyridin-3-yl)azetidine-1-carbimidothioate 14g

The crude product 14f (180 mg, 0.49 mmol) was dissolved in 5 mL of tetrahydrofuran, and then added with potassium tert-butoxide (75.18 mg, 0.67 mmol) in an ice bath, and reacted for 2 hours. The reaction solution was then added with methyl 4-methylbenzenesulfonate (93.58 mg, 0.50 mmol), and reacted for 15 hours. The reaction solution was poured into 30 mL of water to quench the reaction, and extracted with ethyl acetate (30 mL×3). The organic phases were combined, washed with saturated sodium chloride solution (30 mL×2), dried over anhydrous sodium sulfate, and filtered. The filtrate was concentrated under reduced pressure, and the resulting residues were purified by thin layer chromatography with developing solvent system C to obtain the title product 14g (150 mg, yellow liquid), yield: 72.0%.

MS m/z (ESI): 385.2 [M+1].

Step 7

6-Fluoro-3-(1-(5-(methoxymethyl)-4-(6-methoxypyridin-3-yl)-4H-1,2,4-triazol-3-yl) azetidin-3-yl)-1-methyl-1H-indole 14

Compound 14g (180 mg, 0.47 mmol), trifluoroacetic acid (5.34 mg, 0.050 mmol) and 2-methylacetylhydrazine (243.71 mg, 2.34 mmol) were dissolved in 6 mL of tetrahydrofuran successively. After addition, the reaction solution was reacted at 70° C. for 3 hours. The reaction solution was concentrated under reduced pressure to remove the solvent, and the resulting residues were purified by thin layer chromatography with developing solvent system A to obtain the title product 14 (15 mg, pale yellow solid), yield: 7.2%.

MS m/z (ESI): 423.1 [M+1].

$^1$H NMR (400 MHz, CDCl$_3$) δ 8.22 (d, 1H), 7.62 (d, 1H), 7.49 (d, 1H), 6.96-6.83 (m, 4H), 4.34 (s, 2H), 4.19 (d, 2H), 4.05 (m, 1H), 3.98 (s, 5H), 3.69 (s, 3H), 1.26 (s, 3H).

Example 15

5-Fluoro-1-(1-(5-(methoxymethyl)-4-(6-methoxypyridin-3-yl)-4H-1,2,4-triazol-3-yl) azetidin-3-yl)-1H-benzo[d]imidazole 15

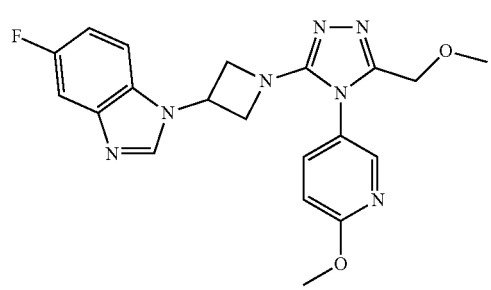

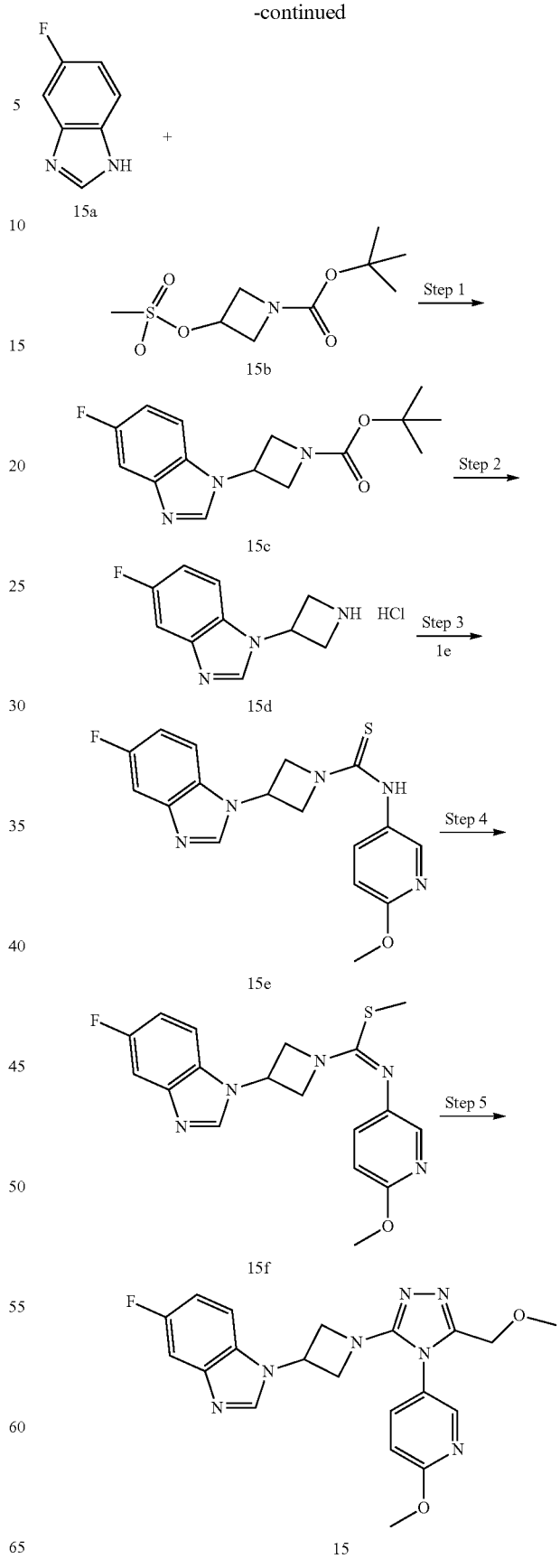

Step 1

Tert-butyl 3-(5-fluoro-1H-benzo[d]imidazol-1-yl) azetidine-1-carboxylate 15c

5-Fluoro-1H-benzo 15a (500 mg, 3.67 mmol), 1-(tert-butoxycarbonyl)-3-(methanesulfonyloxy)azabutane 15b (1015.32 mg, 4.04 mmol, prepared according to the known method disclosed in "*Organic Process Research & Development*, 2015, 19(12), 2067-2074") and cesium carbonate (2393.45 mg, 7.35 mmol) were dissolved in 50 mL of N,N-dimethylformamide, and reacted at 80° C. for 16 hours. The reaction solution was poured into ice water, and extracted with ethyl acetate (50 mL×3). The organic phases were combined, washed with saturated sodium chloride solution, dried over anhydrous sodium sulfate, and filtered. The filtrate was concentrated under reduced pressure, and the resulting residues were purified by silica gel column chromatography with elution system A to obtain the title product 15c (609 mg, pale yellow solid), yield: 56.9%.

MS m/z (ESI): 292.1 [M+1].

Step 2

1-(Azetidin-3-yl)-5-fluoro-1H-benzo[d]imidazole hydrochloride 15d

Compound 15c (609 mg, 2.09 mmol) and a solution of hydrogen chloride in 1,4-dioxane (3.05 mL, 12.18 mmol) were dissolved in 5 mL of dichloromethane, and reacted for 12 hours. The reaction solution was concentrated under reduced pressure to remove the solvent to give the crude title product 15d (450 mg, white solid), which was used directly in the next step without purification.

MS m/z (ESI): 192.0 [M+1].

Step 3

3-(5-Fluoro-1H-benzo[d]imidazol-1-yl)-N-(6-methoxypyridin-3-yl)azetidine-1-carbothioamide 15e

The crude product 15d (450 mg, 2.35 mmol) and compound 1e (586.74 mg, 3.53 mmol) were dissolved in 35 mL of tetrahydrofuran, and reacted for 2 hours after addition. The reaction solution was concentrated under reduced pressure to remove the organic solvent, and the resulting residues were purified by thin layer chromatography with developing solvent system A to obtain the title product 15e (700 mg, pale yellow paste), yield: 83.2%.

MS m/z (ESI): 358.5 [M+1].

Step 4

Methyl (E)-3-(5-fluoro-1H-benzo[d]imidazol-1-yl)-N-(6-methoxypyridin-3-yl)azetidine-1-carbimidothioate 15f

Compound 15e (700 mg, 1.96 mmol) was dissolved in 35 mL of tetrahydrofuran, and then added with potassium tert-butoxide (329.65 mg, 2.94 mmol) in an ice bath, and reacted for 0.5 hour. The reaction solution was then added with methyl 4-methylbenzenesulfonate (364.74 mg, 1.96 mmol), and reacted for 16 hours. The reaction solution was poured into 30 ml of water, and extracted with ethyl acetate (20 mL×3). The organic phases were combined, washed with saturated sodium chloride solution, dried over anhydrous sodium sulfate, and filtered. The filtrate was concentrated under reduced pressure to remove the solvent to give the crude title product 15f (800 mg, white paste), which was used directly in the next step without purification.

MS m/z (ESI): 372.1 [M+1].

Step 5

5-Fluoro-1-(1-(5-(methoxymethyl)-4-(6-methoxypyridin-3-yl)-4H-1,2,4-triazol-3-yl) azetidin-3-yl)-1H-benzo[d]imidazole 15

The crude product 15f (600 mg, 1.62 mmol), trifluoroacetic acid (18.42 mg, 0.16 mmol) and 2-methylacetylhydrazine (168.18 mg, 1.62 mmol) were dissolved in 50 mL of tetrahydrofuran successively. After addition, the reaction solution was heated to reflux and reacted for 2 hours. The reaction solution was cooled to room temperature, and concentrated under reduced pressure. The resulting residues were purified by HPLC to obtain the title product 15 (100 mg, pale yellow solid), yield: 15.1%.

MS m/z (ESI): 410.1[M+1].

¹HNMR (400 MHz, DMSO-d₆) δ 8.29 (s, 1H), 8.05 (d, 1H), 7.69-7.67 (m, 1H), 7.53-7.50 (m, 1H), 7.35-7.32 (m, 1H), 7.13-7.12 (m, 1H), 6.93-6.89 (m, 1H), 5.24-5.18 (m, 1H), 4.52-4.50 (m, 2H), 4.40 (s, 2H), 4.30-4.24 (m, 2H), 4.01 (s, 3H), 3.37 (s, 3H).

Example 16

5-Fluoro-1-(1-(5-(methoxymethyl)-4-(6-methoxypyridin-3-yl)-4H-1,2,4-triazol-3-yl) azetidin-3-yl)-2-methyl-1H-indole 16

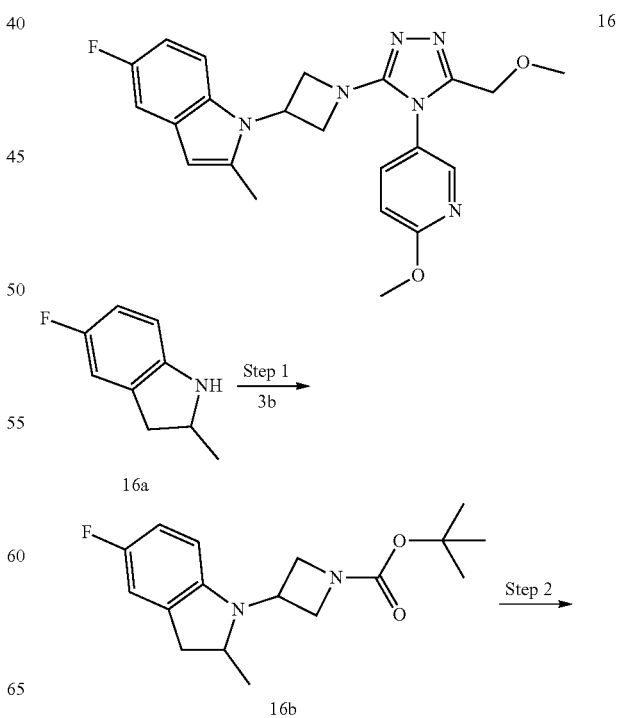

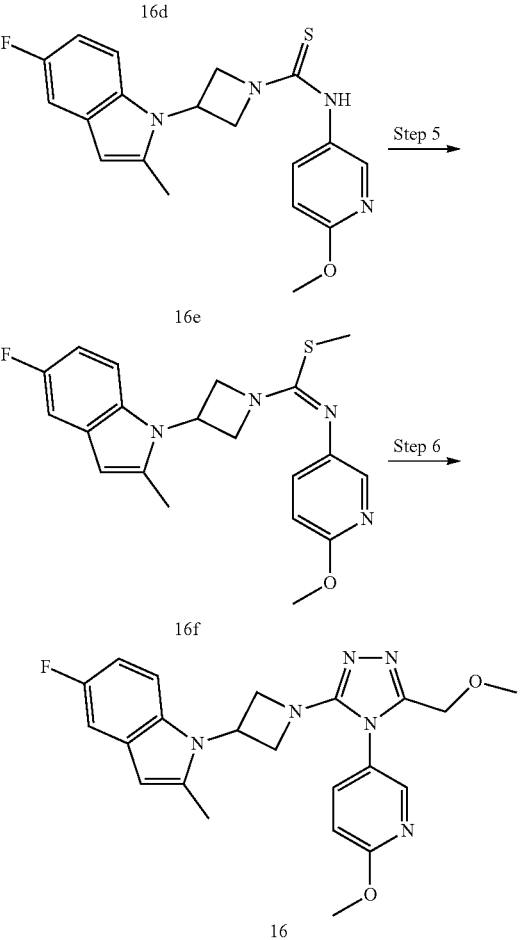

of water, and the water phase was extracted with dichloromethane (50 mL×2). The organic phases were combined, dried over anhydrous sodium sulfate, and filtered. The filtrate was concentrated under reduced pressure, and the resulting residues were purified by thin layer chromatography with developing solvent system A to obtain the title product 16b (1.80 g, yellow oil), yield: 64.3%.

MS m/z (ESI): 307.1 [M+1].

Step 2

Tert-butyl 3-(5-fluoro-2-methyl-1H-indol-1-yl)azetidine-1-carboxylate 16c

Compound 16b (270 mg, 0.88 mmol) was dissolved in 10 mL of dichloromethane, and the solution was placed in an ice bath to cool to 0° C. The above solution was then added with 2,3-dichloro-5,6-dicyano-p-quinone (300.07 mg, 1.32 mmol), and reacted for 1 hour after addition. The reaction solution was concentrated under reduced pressure, and the resulting residues were purified by thin layer chromatography with developing solvent system B to obtain the title product 16c (170 mg, yellow solid), yield: 57.0%.

MS m/z (ESI): 305.3 [M+1].

Step 3

1-(Azetidin-3-yl)-5-fluoro-2-methyl-1H-indole Hydrochloride 16d

Compound 16c (170 mg, 0.55 mmol) was dissolved in 10 mL of dichloromethane. The above solution was then added with 2 mL solution of hydrogen chloride in 1,4-dioxane (4 M), and reacted for 16 hours after addition. The reaction solution was concentrated under reduced pressure to give the crude title product 16d (100 mg, pale yellow solid), which was used directly in the next step without purification.

MS m/z (ESI): 205.1 [M+1].

Step 4

3-(5-Fluoro-2-methyl-1H-indol-1-yl)-N-(6-methoxypyridin-3-yl)azetidine-1-carbothioamide 16e The crude product 16d (100 mg, 0.49 mmol) and compound 1e (122.06 mg, 0.73 mmol) were dissolved in 15 mL of tetrahydrofuran successively, and reacted for 2 hours after addition. The reaction solution was concentrated under reduced pressure to give the crude title product 16e (980 mg, yellow solid), which was used directly in the next step without purification.

MS m/z (ESI): 371.1 [M+1].

Step 5

Methyl (E)-3-(5-fluoro-2-methyl-1H-indol-1-yl)-N-(6-methoxypyridin-3-yl)azetidine-1-carbimidothioate 16f Compound 16e (150 mg, 0.40 mmol) was dissolved in 15 mL of tetrahydrofuran, and cooled to 0° C. The above solution was then added with potassium tert-butoxide (90.87 mg, 0.81 mmol), and reacted for 0.5 hour after addition. The reaction solution was then added with methyl 4-methylbenzenesulfonate (113.11 mg, 0.61 mmol), and then slowly warmed up to room temperature, and reacted for 16 hours. The reaction solution was poured into 50 mL of water, and Step 1

Tert-butyl 3-(5-fluoro-2-methylindolin-1-yl)azetidine-1-carboxylate 16b

5-Fluoro-2-methylindoline 16a (1.30 g, 8.60 mmol, prepared according to the known method disclosed in "*Tetrahedron: Asymmetry,* 2006, 17(17), 2558-2564") and compound 3b (1.47 g, 8.60 mmol) were dissolved in 40 mL of dichloromethane successively, and stirred for 2 hours. The reaction solution was then added with sodium triacetoxyborohydride (2.73 g, 12.90 mmol), and reacted for 12 hours after addition. The reaction solution was poured into 50 ml extracted with ethyl acetate (50 mL×3). The organic phases were combined, dried over anhydrous sodium sulfate, and filtered. The filtrate was concentrated under reduced pressure to give the crude title product 16f (150 mg, yellow paste), which was used directly in the next step without purification.

MS m/z (ESI): 385.1 [M+1].

Step 6

5-Fluoro-1-(1-(5-(methoxymethyl)-4-(6-methoxy-pyridin-3-yl)-4H-1,2,4-triazol-3-yl) azetidin-3-yl)-2-methyl-1H-indole 16

The crude product 16f (150 mg, 0.39 mmol), 2-methoxy-acetylhydrazine (60.93 mg, 0.59 mmol) and trifluoroacetic acid (4.45 mg, 0.040 mmol) were dissolved in 15 mL of tetrahydrofuran successively. After addition, the reaction solution was heated to 70° C. and reacted for 2 hours. The reaction solution was concentrated under reduced pressure, and the resulting residues were purified by HPLC to obtain the title product 16 (30 mg, pale yellow solid), yield: 18.2%.

MS m/z (ESI): 423.1 [M+1].

$^1$HNMR (400 MHz, DMSO-$d_6$) δ 8.37 (s, 1H), 7.80 (d, 1H), 7.60-7.58 (m, 1H), 7.21 (d, 1H), 6.97-6.92 (m, 2H), 6.21 (s, 1H), 5.42-5.38 (m, 1H), 4.73-4.64 (m, 4H), 4.35 (s, 2H), 4.00 (s, 3H), 3.31 (s, 3H), 2.38 (s, 3H).

Example 17

5-Fluoro-1-(1-(5-(methoxymethyl)-4-(6-methoxy-pyridin-3-yl)-4H-1,2,4-triazol-3-yl) azetidin-3-yl)-3-methyl-1H-indole 17

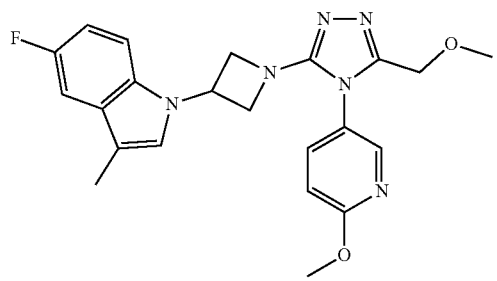

17

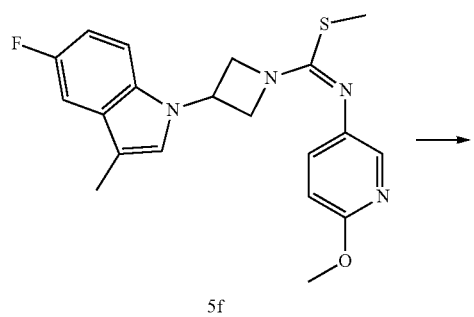

5f

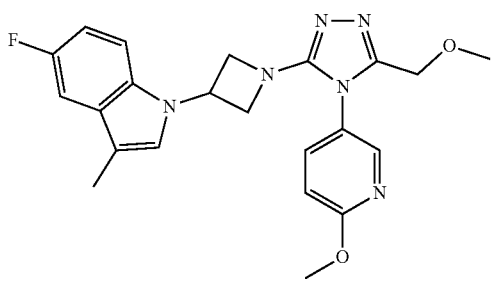

17

Compound 5f (60 mg, 0.16 mmol), 2-methoxyacetylhydrazine (16.25 mg, 0.16 mmol) and three drops of trifluoroacetic acid were dissolved in 10 mL of tetrahydrofuran successively. After addition, the reaction solution was heated to 66° C. and reacted for 3 hours. The reaction solution was concentrated under reduced pressure, and the resulting residues were purified by thin layer chromatography with developing solvent system A to obtain the title product 17 (15 mg, pale yellow oil), yield: 22.8%.

MS m/z (ESI): 423.5 [M+1].

$^1$H NMR (400 MHz, CD$_3$OD) δ 8.33 (d, 1H), 7.85 (d, 1H), 7.36 (d, 1H), 7.32 (s, 1H), 7.15 (d, 1H), 6.98 (d, 1H), 6.95 (t, 1H), 5.32-5.38 (m, 1H), 4.35 (s, 2H), 4.31 (d, 2H), 4.13 (t, 2H), 3.98 (s, 3H), 3.28 (s, 3H), 2.27 (s, 3H).

Example 18

7-Fluoro-4-(1-(5-(methoxymethyl)-4-(6-methoxy-pyridin-3-yl)-4H-1,2,4-triazol-3-yl) azetidin-3-yl)-2H-benzo[b][1,4]oxazin-3(4H)-one 18

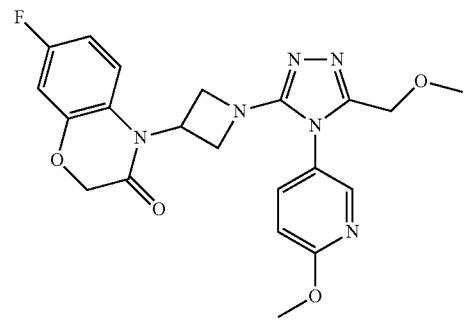

18

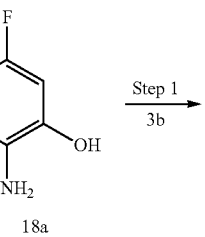

18a

Step 1
3b

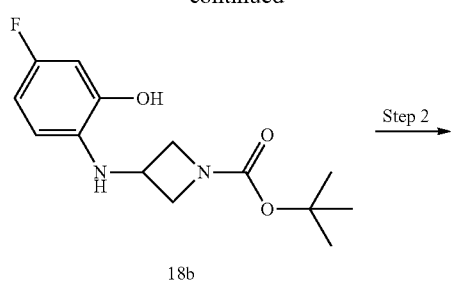

18b

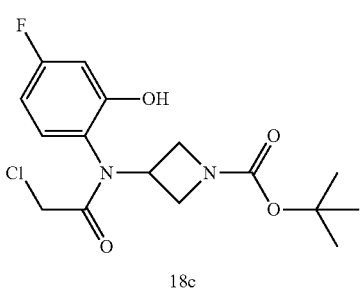

18c

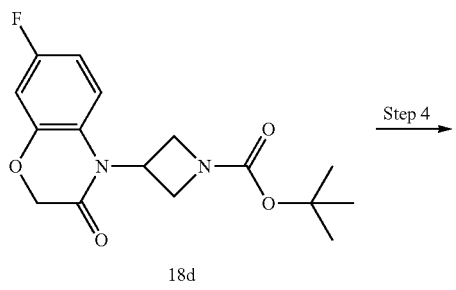

18d

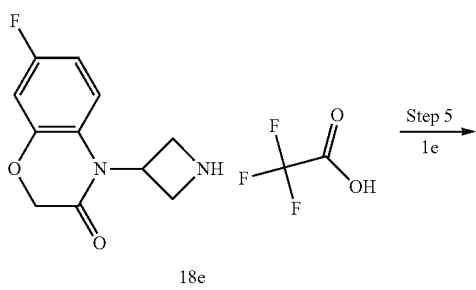

18e

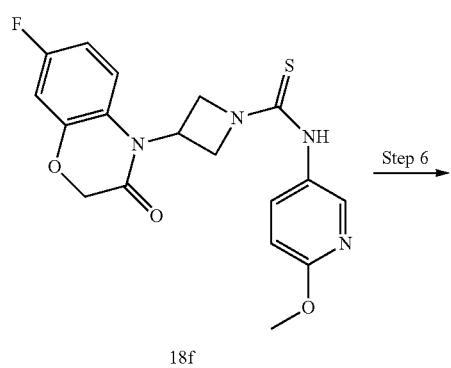

18f

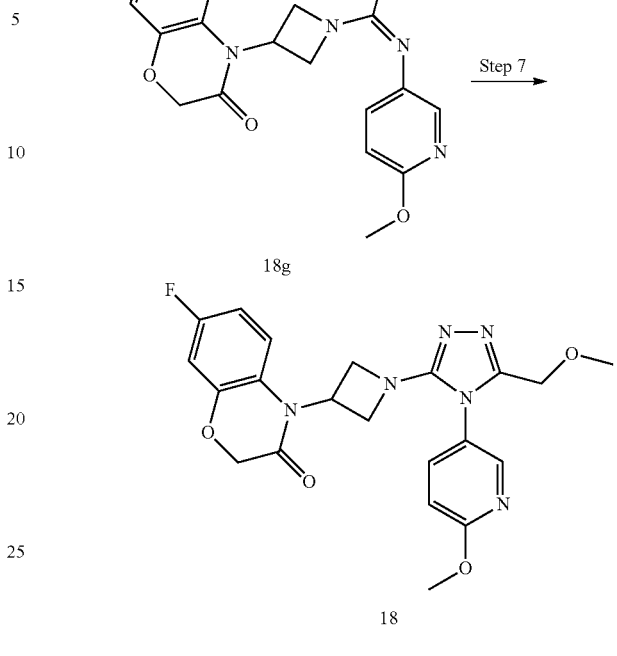

18g

18

Step 1

Tert-butyl 3-((4-fluoro-2-hydroxyphenyl)amino)azetidine-1-carboxylate 18b

2-Amino-5-fluorophenol 18a (1000 mg, 7.87 mmol) and compound 3b (1346.68 mg, 7.87 mmol) were dissolved in 40 mL of dichloromethane successively, and stirred for 2 hours. The reaction solution was then added with sodium triacetoxyborohydride (5001.73 mg, 23.6 mmol), and reacted for 12 hours after addition. The reaction solution was poured into 50 ml of water, and washed. The organic phases were combined, dried over anhydrous sodium sulfate, and filtered. The filtrate was concentrated under reduced pressure, and the resulting residues were purified by thin layer chromatography with developing solvent system A to obtain the title product 18b (1500 mg, brown solid), yield: 67.6%.

MS m/z (ESI): 283.1 [M+1].

Step 2

Tert-butyl 3-(2-chloro-N-(4-fluoro-2-hydroxyphenyl)acetamido)azetidine-1-carboxylate 18c Compound 18b (500 mg, 1.77 mmol) and triethylamine (202.38 mg, 2 mmol) were dissolved in 50 mL of dichloromethane. The above reaction solution was added with 2-chloroacetyl chloride (124.23 mg, 1.1 mmol) in an ice bath, then slowly warmed up to room temperature, and reacted for 1 hour. The reaction solution was washed with 30 mL of water, and the organic phase was dried over anhydrous sodium sulfate and filtered. The filtrate was concentrated under reduced pressure, and the resulting residues were purified by silica gel column chromatography with elution system C to obtain the title product 18c (500 mg, brown solid), yield: 78.6%.

MS m/z (ESI): 359.1 [M+1].

Step 3

Tert-butyl 3-(7-fluoro-3-oxo-2H-benzo[b][1,4]
oxazin-4(3H)-yl)azetidine-1-carboxylate 18d Compound 18c (500 mg, 1.39 mmol) and potassium carbonate (577.82 mg, 4.18 mmol) were dissolved in 30 mL of N,N-dimethylformamide, and reacted at 100° C. for 12 hours. The reaction solution was cooled to room temperature, and filtered. The filtrate was concentrated under reduced pressure, and the resulting residues were purified by thin layer chromatography with developing solvent system C to obtain the title product 18d (170 mg, brown oil), yield: 37.8%.

MS m/z (ESI): 323.2 [M+1].

Step 4

4-(Azetidin-3-yl)-7-fluoro-2H-benzo[b][1,4]oxazin-
3(4H)-one Trifluoroacetate 18e Compound 18d (50 mg, 0.16 mmol) and trifluoroacetic acid (176.87 mg, 1.55 mmol) were dissolved in 20 mL of dichloromethane, and reacted for 0.5 hour after addition. The reaction solution was concentrated under reduced pressure, and the resulting residues were purified by thin layer chromatography with developing solvent system A to obtain the title product 18e (34 mg, brown solid), yield: 98.6%.

MS m/z (ESI): 223.1 [M+1].

Step 5

3-(7-Fluoro-3-oxo-2H-benzo[b][1,4]oxazin-4(3H)-
yl)-N-(6-methoxypyridin-3-yl) azetidine-1-carboth-
ioamide 18f Compound 18e (100 mg, 0.45 mmol) and compound 1e (74.79 mg, 0.45 mmol) were dissolved in 30 mL of tetrahydrofuran successively, and reacted for 2 hours after addition. The reaction solution was concentrated under reduced pressure to remove the organic solvent, and the resulting residues were purified by thin layer chromatography with developing solvent system C to obtain the title product 18f (40 mg, brown oil), yield: 22.9%.

MS m/z (ESI): 389.3 [M+1].

Step 6

Methyl (E)-3-(7-fluoro-3-oxo-2H-benzo[b][1,4]
oxazin-4(3H)-yl)-N-(6-methoxypyridin-3-yl) azeti-
dine-1-carbimidothioate 18g Compound 18f (40 mg, 0.1 mmol) was dissolved in 20 mL of tetrahydrofuran, and cooled to 0° C. The above solution was then added with potassium tert-butoxide (12 mg, 0.10 mmol), and reacted for 0.5 hour after addition. The reaction solution was then added with methyl 4-methylbenzenesulfonate (19.18 mg, 0.10 mmol), and then slowly warmed up to room temperature, and reacted for 12 hours. The reaction solution was poured into 30 mL of water, extracted with ethyl acetate (30 mL×3), and washed with saturated sodium chloride solution (30 mL×2). The organic phases were combined, dried over anhydrous sodium sulfate, and filtered. The filtrate was concentrated under reduced pressure, and the resulting residues were purified by thin layer chromatography with developing solvent system C to obtain the title product 18g (10 mg, brown solid), yield: 24.1%.

MS m/z (ESI): 403.1 [M+1].

Step 7

7-Fluoro-4-(1-(5-(methoxymethyl)-4-(6-methoxy-
pyridin-3-yl)-4H-1,2,4-triazol-3-yl) azetidin-3-yl)-
2H-benzo[b][1,4]oxazin-3(4H)-one 18

Compound 18g (60 mg, 0.15 mmol), 2-methoxyacetylhydrazine (15.52 mg, 0.15 mmol) and trifluoroacetic acid (1.7 mg, 0.010 mmol) were dissolved in 20 mL of tetrahydrofuran successively. After addition, the reaction solution was heated to reflux and reacted for 3 hours. The reaction solution was concentrated under reduced pressure, and the resulting residues were purified by thin layer chromatography with developing solvent system A to obtain the title product 18 (20 mg, brown solid), yield: 28.9%.

MS m/z (ESI): 441.1[M+1].

$^1$H NMR (400 MHz, CD$_3$OD) δ 8.28 (d, 1H), 7.78-7.81 (m, 1H), 6.99 (d, 1H), 6.82-6.86 (m, 3H), 4.53 (s, 2H), 4.31 (s, 2H), 4.14-4.16 (m, 3H), 4.04 (s, 3H), 3.50-3.55 (m, 2H), 3.24 (s, 3H).

Example 19

5-Fluoro-1-(1-(5-(methoxymethyl)-4-(6-methoxy-
pyridin-3-yl)-4H-1,2,4-triazol-3-yl) azetidin-3-yl)-1,
2,3,4-tetrahydroquinoline 19

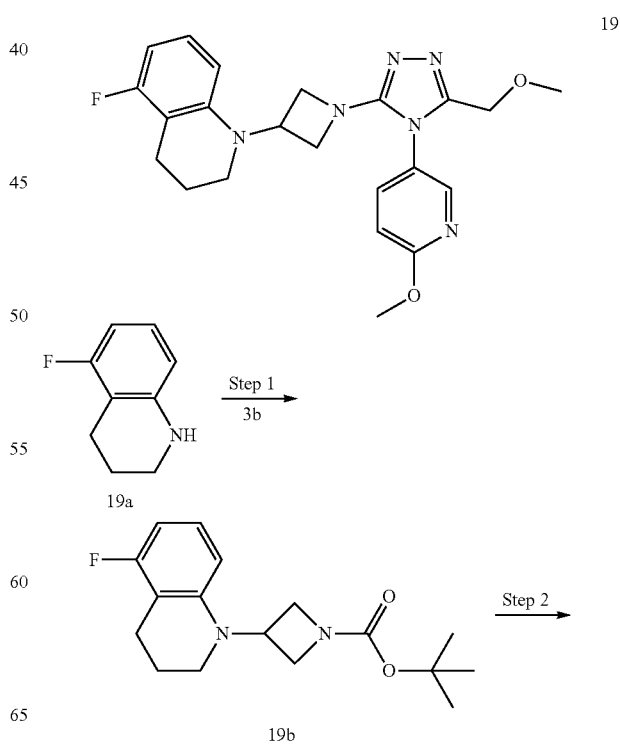

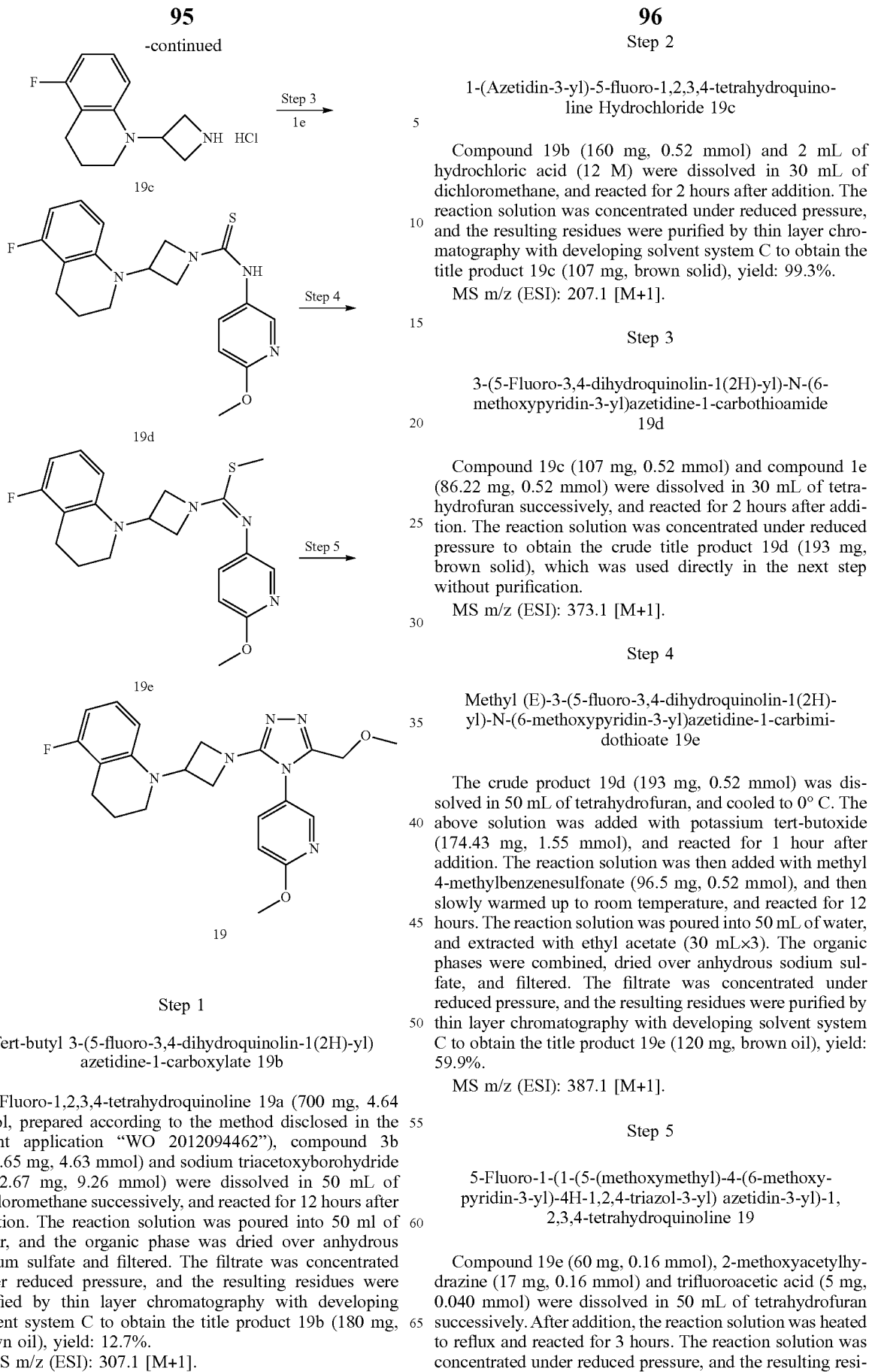

Step 1

Tert-butyl 3-(5-fluoro-3,4-dihydroquinolin-1(2H)-yl) azetidine-1-carboxylate 19b 5-Fluoro-1,2,3,4-tetrahydroquinoline 19a (700 mg, 4.64 mmol, prepared according to the method disclosed in the patent application "WO 2012094462"), compound 3b (792.65 mg, 4.63 mmol) and sodium triacetoxyborohydride (1962.67 mg, 9.26 mmol) were dissolved in 50 mL of dichloromethane successively, and reacted for 12 hours after addition. The reaction solution was poured into 50 ml of water, and the organic phase was dried over anhydrous sodium sulfate and filtered. The filtrate was concentrated under reduced pressure, and the resulting residues were purified by thin layer chromatography with developing solvent system C to obtain the title product 19b (180 mg, brown oil), yield: 12.7%.

MS m/z (ESI): 307.1 [M+1].

Step 2

1-(Azetidin-3-yl)-5-fluoro-1,2,3,4-tetrahydroquinoline Hydrochloride 19c

Compound 19b (160 mg, 0.52 mmol) and 2 mL of hydrochloric acid (12 M) were dissolved in 30 mL of dichloromethane, and reacted for 2 hours after addition. The reaction solution was concentrated under reduced pressure, and the resulting residues were purified by thin layer chromatography with developing solvent system C to obtain the title product 19c (107 mg, brown solid), yield: 99.3%.

MS m/z (ESI): 207.1 [M+1].

Step 3

3-(5-Fluoro-3,4-dihydroquinolin-1(2H)-yl)-N-(6-methoxypyridin-3-yl)azetidine-1-carbothioamide 19d Compound 19c (107 mg, 0.52 mmol) and compound 1e (86.22 mg, 0.52 mmol) were dissolved in 30 mL of tetrahydrofuran successively, and reacted for 2 hours after addition. The reaction solution was concentrated under reduced pressure to obtain the crude title product 19d (193 mg, brown solid), which was used directly in the next step without purification.

MS m/z (ESI): 373.1 [M+1].

Step 4

Methyl (E)-3-(5-fluoro-3,4-dihydroquinolin-1(2H)-yl)-N-(6-methoxypyridin-3-yl)azetidine-1-carbimidothioate 19e The crude product 19d (193 mg, 0.52 mmol) was dissolved in 50 mL of tetrahydrofuran, and cooled to 0° C. The above solution was added with potassium tert-butoxide (174.43 mg, 1.55 mmol), and reacted for 1 hour after addition. The reaction solution was then added with methyl 4-methylbenzenesulfonate (96.5 mg, 0.52 mmol), and then slowly warmed up to room temperature, and reacted for 12 hours. The reaction solution was poured into 50 mL of water, and extracted with ethyl acetate (30 mL×3). The organic phases were combined, dried over anhydrous sodium sulfate, and filtered. The filtrate was concentrated under reduced pressure, and the resulting residues were purified by thin layer chromatography with developing solvent system C to obtain the title product 19e (120 mg, brown oil), yield: 59.9%.

MS m/z (ESI): 387.1 [M+1].

Step 5

5-Fluoro-1-(1-(5-(methoxymethyl)-4-(6-methoxypyridin-3-yl)-4H-1,2,4-triazol-3-yl) azetidin-3-yl)-1,2,3,4-tetrahydroquinoline 19

Compound 19e (60 mg, 0.16 mmol), 2-methoxyacetylhydrazine (17 mg, 0.16 mmol) and trifluoroacetic acid (5 mg, 0.040 mmol) were dissolved in 50 mL of tetrahydrofuran successively. After addition, the reaction solution was heated to reflux and reacted for 3 hours. The reaction solution was concentrated under reduced pressure, and the resulting residues were purified by thin layer chromatography with developing solvent system A to obtain the title product 19 (30 mg, brown solid), yield: 44.1%.

MS m/z (ESI): 425.2 [M+1].

$^1$H NMR (400 MHz, CD$_3$OD) δ 8.29 (d, 1H), 7.79-7.82 (m, 1H), 6.95-7.00 (m, 2H), 6.39-6.41 (m, 1H), 6.19 (d, 1H), 4.49-4.50 (m, 1H), 4.32 (s, 2H), 3.93-4.04 (m, 7H), 3.26 (s, 3H), 3.15-3.18 (m, 2H), 2.69 (t, 2H), 1.93-1.96 (m, 2H).

Example 20

5-Fluoro-1-(1-(4-(6-methoxypyridin-3-yl)-5-methyl-4H-1,2,4-triazol-3-yl)azetidin-3-yl)-1,2,3,4-tetrahydroquinoline 20

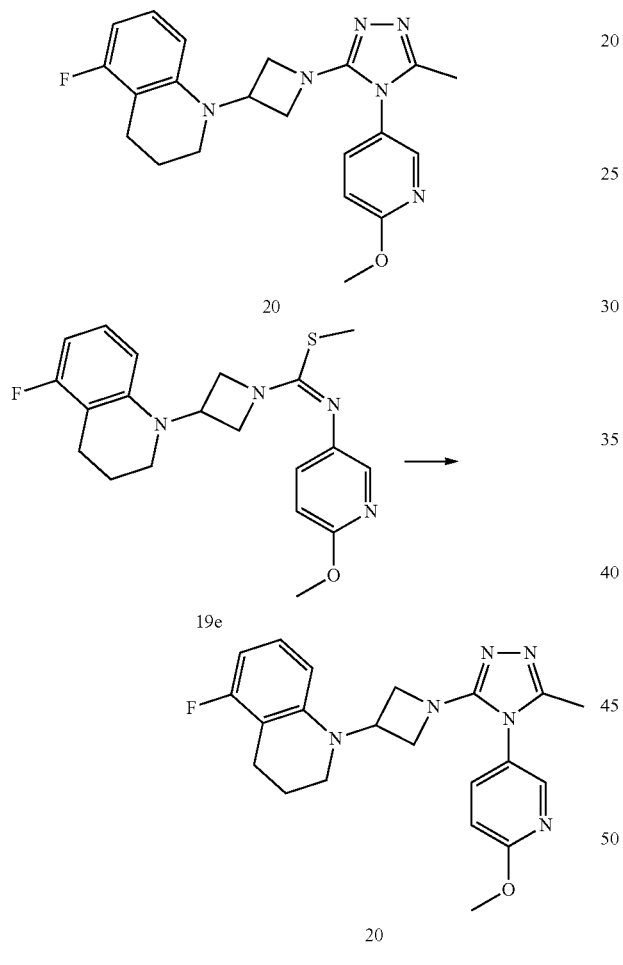

Compound 19e (60 mg, 0.16 mmol), acetylhydrazine (60 mg, 0.81 mmol) and trifluoroacetic acid (60 mg, 0.53 mmol) were dissolved in 50 mL of tetrahydrofuran successively. After addition, the reaction solution was heated to reflux and reacted for 3 hours. The reaction solution was concentrated under reduced pressure, and the resulting residues were purified by HPLC to obtain the title product 20 (10 mg, white solid), yield: 16.3%.

MS m/z (ESI): 395.2 [M+1].

$^1$H NMR (400 MHz, CDCl$_3$) δ 8.12-8.11 (m, 1H), 7.51-7.48 (m, 1H), 6.97-6.91 (m, 2H), 6.44-6.40 (m, 1H), 6.06-6.04 (m, 1H), 4.44-4.41 (m, 1H), 4.02 (s, 3H), 4.01-3.94 (m, 4H), 3.15-3.12 (m, 2H), 2.72-2.68 (m, 2H), 2.21 (s, 3H), 1.96-1.90 (m, 2H).

Example 21

5-(3-(3-(7-Fluorobenzodihydropyran-4-yl)azetidin-1-yl)-5-(methoxymethyl)-4H-1,2,4-triazol-4-yl)-2-methoxypyridine 21

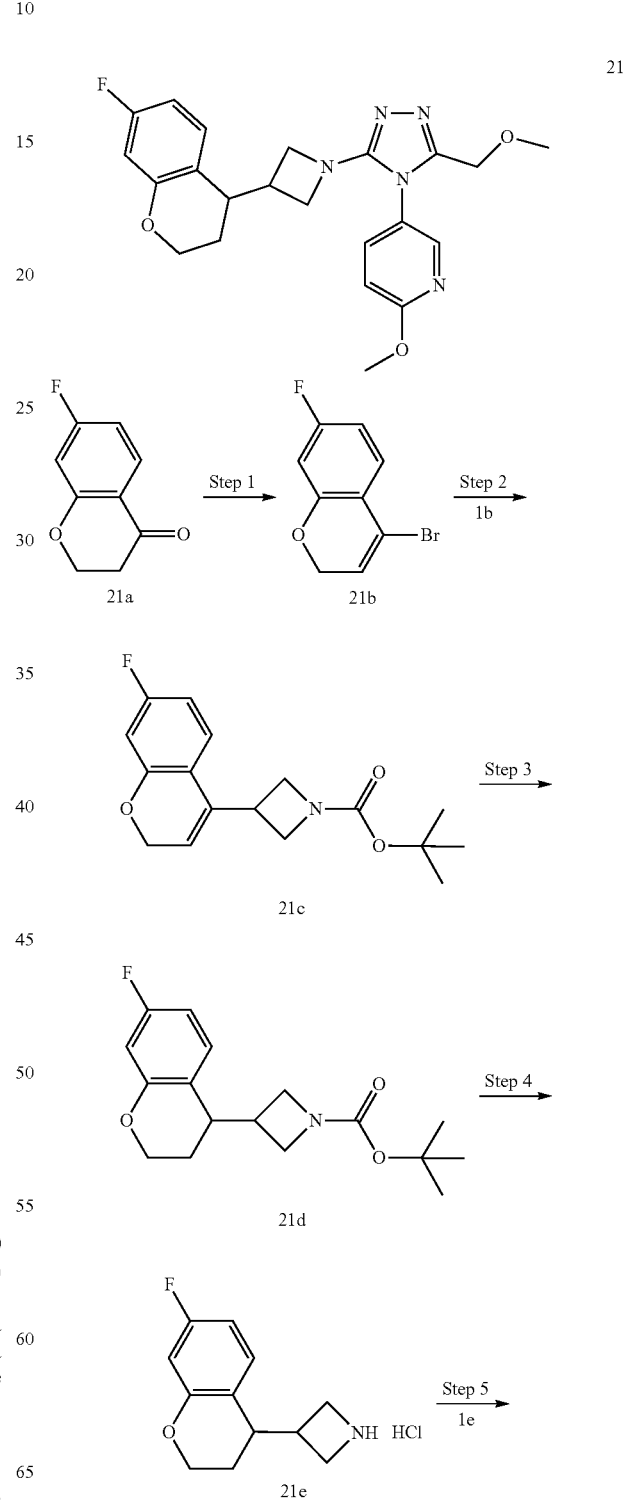

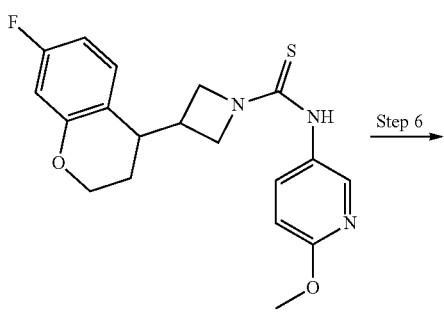

21f

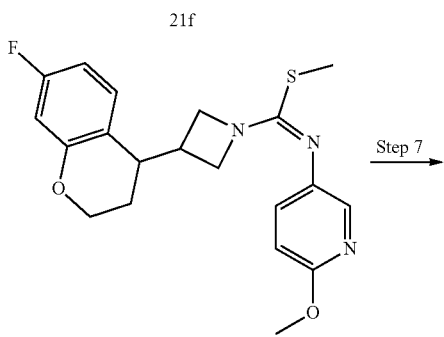

21g

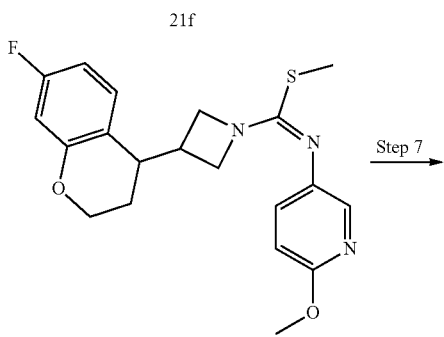

21

Step 1

4-Bromo-7-fluoro-2H-benzopyran 21b 10 mL of phosphorus tribromide and 7-fluorobenzodihydropyran-4-one 21a (2000 mg, 12.04 mmol, prepared according to the known method disclosed in "*European Journal of Medicinal Chemistry*, 2015, 90, 834-844") were mixed. The reaction solution was reacted at 90° C. for 16 hours. The reaction solution was poured into 50 mL of ice water, and added with saturated sodium bicarbonate solution to adjust the pH to >7, and extracted with ethyl acetate (30 mL×3). The organic phases were combined, dried over anhydrous sodium sulfate, and filtered. The filtrate was concentrated under reduced pressure, and the resulting residues were purified by silica gel column chromatography with elution system B to obtain the title product 21b (490 mg, white solid), yield: 17.6%.

Step 2

Tert-butyl 3-(7-fluoro-2H-benzopyran-4-yl)azetidine-1-carboxylate 21c

Compound 1b (741.61 mg, 2.62 mmol), iodine (83.11 mg, 0.33 mmol) and zinc (713.6 mg, 10.9 mmol) were added to 30 mL of N,N-dimethylformamide, and reacted under argon atmosphere for 0.5 hour. The above reaction solution was added with bis(dibenzylideneacetone)palladium (99.9 mg, 0.11 mmol), 2-dicyclohexylphosphine-2',4',6'-triisopropylbiphenyl (52.03 mg, 0.11 mmol) and 4-bromo-7-fluoro-1,2-dihydronaphthalene 21b (500 mg, 2.18 mmol). After addition, the reaction solution was heated to 55° C. for 5 hours. The reaction solution was cooled to room temperature, and concentrated under reduced pressure. The resulting residues were purified by silica gel column chromatography with elution system B to obtain the title product 21c (300 mg, pale yellow solid), yield: 40.5%.

MS m/z (ESI): 250.1 [M−55].

Step 3

Tert-butyl 3-(7-fluorodihydrobenzopyran-4-yl)azetidine-1-carboxylate 21d

Compound 21c (300 mg, 0.98 mmol) was dissolved in 10 mL of methanol. The above reaction solution was then added with platinum dioxide (22.31 mg, 0.98 mmol), and reacted under hydrogen atmosphere for 1 hour. The reaction solution was filtered, and the filtrate was concentrated under reduced pressure to give the crude title product 21d (300 mg, yellow solid), which was used directly in the next step without purification.

MS m/z (ESI): 252.1 [M−55].

Step 4

3-(7-Fluorodihydrobenzopyran-4-yl)azetidine Hydrochloride 21e

The crude product 21d (300 mg, 0.98 mmol) and 5 mL solution of hydrogen chloride in 1,4-dioxane (4 M) were dissolved in 5 mL of dichloromethane, and reacted for 2 hours after addition. The reaction solution was concentrated under reduced pressure to obtain the crude title product 21e (200 mg, white solid), which was used directly in the next step without purification.

MS m/z (ESI): 208.2 [M+1].

Step 5

3-(7-Fluorodihydrobenzopyran-4-yl)-N-(6-methoxypyridin-3-yl)azetidine-1-carbothioamide 21f The crude product 21e (200 mg, 0.97 mmol) and compound 1e (160.39 mg, 0.97 mmol) were dissolved in 15 mL of tetrahydrofuran successively, and reacted for 2 hours after addition. The reaction solution was concentrated under reduced pressure to obtain the crude title product 21f (360 mg, brown solid), which was used directly in the next step without purification.

MS m/z (ESI): 374.2 [M+1].

Step 6

Methyl (E)-3-(7-fluorodihydrobenzopyran-4-yl)-N-(6-methoxypyridin-3-yl)azetidine-1-carbimidothioate 21g The crude product 21f (360 mg, 0.96 mmol) was dissolved in 20 mL of tetrahydrofuran, and cooled to 0° C. The above solution was added with potassium tert-butoxide (269.29 mg, 1.45 mmol), and reacted for 0.5 hour after addition. The reaction solution was then added with methyl 4-methylbenzenesulfonate (269.29 mg, 1.45 mmol), and then slowly warmed up to room temperature, and reacted for 16 hours. The reaction solution was poured into 50 mL of water, and extracted with ethyl acetate (30 mL×3). The organic phases were combined, dried over anhydrous sodium sulfate, and filtered. The filtrate was concentrated under reduced pressure, and the resulting residues were purified by silica gel column chromatography with elution system A to obtain the title product 21g (150 mg, yellow oil), yield: 40.2%.

MS m/z (ESI): 388.1 [M+1].

Step 7

5-(3-(3-(7-Fluorobenzo dihydropyran-4-yl)azetidin-1-yl)-5-(methoxymethyl)-4H-1,2,4-triazol-4-yl)-2-methoxypyridine 21

Compound 21g (150 mg, 0.39 mmol), 2-methoxyacetyl-hydrazine (48.36 mg, 0.46 mmol) and trifluoroacetic acid (4.41 mg, 0.040 mmol) were dissolved in 20 mL of tetrahydrofuran successively. After addition, the reaction solution was heated to reflux and reacted for 2 hours. The reaction solution was concentrated under reduced pressure, and the resulting residues were purified by thin layer chromatography with developing solvent system A to obtain the title product 21 (30 mg, white paste), yield: 18.8%.

MS m/z (ESI): 426.2 [M+1].
$^1$H NMR (400 MHz, DMSO-$d_6$) δ 8.25 (s, 1H), 7.64 (d, 1H), 7.91 (d, 1H), 6.84-6.80 (m, 1H), 6.56-6.52 (m, 2H), 4.35 (s, 2H), 4.17-4.16 (m, 2H), 4.04 (s, 3H), 4.00-3.98 (m, 1H), 3.91-3.90 (m, 1H), 3.78-3.76 (m, 1H), 3.72-3.70 (m, 1H), 3.34 (s, 3H), 2.98-2.93 (m, 2H), 2.03-1.98 (m, 1H), 1.66-1.62 (m, 1H).

Example 22

8-Fluoro-4-(1-(5-(methoxymethyl)-4-(6-methoxy-pyridin-3-yl)-4H-1,2,4-triazol-3-yl) azetidin-3-yl)-3,4-dihydro-2H-benzo[b][1,4]oxazine 22

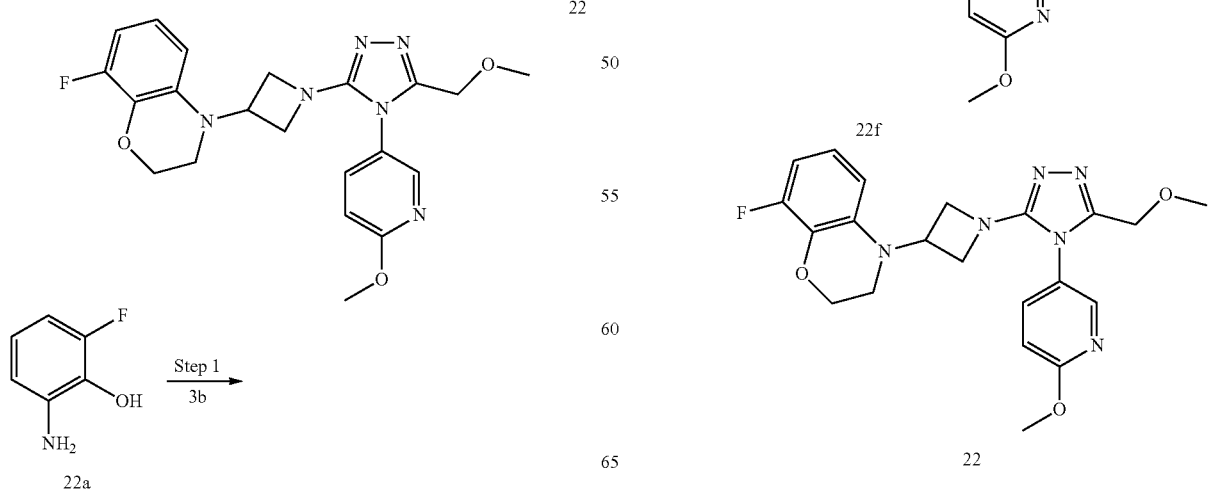

Step 1

Tert-butyl 3-((3-fluoro-2-hydroxyphenyl)amino) azetidine-1-carboxylate 22b

2-Amino-6-fluorophenol 22a (1000 mg, 7.87 mmol), sodium triacetoxyborohydride (1667.24 mg, 7.87 mmol) and compound 3b (1346.68 mg, 7.87 mmol) were dissolved in 100 mL of dichloromethane, and reacted for 12 hours after addition. The reaction solution was poured into 100 mL of water, extracted with dichloromethane (100 mL×3), and washed. The organic phases were combined, dried over anhydrous sodium sulfate, and filtered. The filtrate was concentrated under reduced pressure to obtain the crude title product 22b (1500 mg, brown paste), which was used directly in the next step without purification.

MS m/z (ESI): 283.2 [M+1].

Step 2

Tert-butyl 3-(8-fluoro-2H-benzo[b][1,4]oxazin-4 (3H)-yl)azetidine-1-carboxylate 22c

The crude product 22b (998.16 mg, 5.31 mmol), 1,2-dibromoethane (998.16, 5.31 mmol) and potassium carbonate (489.57 mg, 3.54 mmol) were dissolved in 50 mL of N,N-dimethylformamide. After addition, the reaction solution was reacted at 90° C. for 12 hours. The reaction solution was concentrated under reduced pressure, and the residues were added with 100 mL of water and extracted with dichloromethane (100 mL×3). The organic phases were combined, dried over anhydrous sodium sulfate, and filtered. The filtrate was concentrated under reduced pressure, and the resulting residues were purified by thin layer chromatography with developing solvent system C to obtain the title product 22c (1000 mg, brown solid), yield: 73.2%.

MS m/z (ESI): 309.4 [M+1].

Step 3

4-(Azetidin-3-yl)-8-fluoro-3,4-2H-benzo[b][1,4] oxazine Hydrochloride 22d

Compound 22c (1000 mg, 3.24 mmol) and 8.11 mL solution of hydrogen chloride in 1,4-dioxane (4 M) were dissolved in 20 mL of dichloromethane, and reacted for 3 hours after addition. The reaction solution was concentrated under reduced pressure to obtain the crude title product 22d (900 mg, black solid), which was used directly in the next step without purification.

MS m/z (ESI): 209.2 [M+1].

Step 4

3-(8-Fluoro-2H-benzo[b][1,4]oxazin-4(3H)-yl)-N-(6-methoxypyridin-3-yl)azetidine-1-carbothioamide 22e

Compound 22d (500 mg, 2.40 mmol) and 1e (399.08 mg, 2.40 mmol) were dissolved in 50 mL of tetrahydrofuran successively, and reacted for 3 hours after addition. The reaction solution was concentrated under reduced pressure to obtain the crude title product 22e (600 mg, black solid), which was used directly in the next step without purification.

MS m/z (ESI): 375.4 [M+1].

Step 5

Methyl (E)-3-(8-fluoro-2H-benzo[b][1,4]oxazin-4 (3H)-yl)-N-(6-methoxypyridin-3-yl)azetidine-1-carbimidothioate 22f

The crude product 22e (300 mg, 0.80 mmol) and potassium tert-butoxide (179.81 mg, 1.6 mmol) were dissolved in 30 mL of tetrahydrofuran, cooled to 0° C., and reacted for 1 hour after addition. The reaction solution was then added with methyl 4-methylbenzenesulfonate (149.21 mg, 0.80 mmol), and then slowly warmed up to room temperature, and reacted for 16 hours. The reaction solution was poured into 25 mL of water, and extracted with dichloromethane (30 mL×3). The organic phases were combined, dried over anhydrous sodium sulfate, and filtered. The filtrate was concentrated under reduced pressure, and the resulting residues were purified by thin layer chromatography with developing solvent system C to obtain the title product 22f (100 mg, yellow oil), yield: 22.5%.

MS m/z (ESI): 389.2 [M+1].

Step 6

8-Fluoro-4-(1-(5-(methoxymethyl)-4-(6-methoxypyridin-3-yl)-4H-1,2,4-triazol-3-yl) azetidin-3-yl)-3,4-dihydro-2H-benzo[b][1,4]oxazine 22

Compound 22f (100 mg, 0.26 mmol), 2-methoxyacetylhydrazine (53.6 mg, 0.51 mmol) and trifluoroacetic acid (29.35 mg, 0.26 mmol) were dissolved in 20 mL of tetrahydrofuran successively. After addition, the reaction solution was heated to 65° C. and reacted for 3 hours. The reaction solution was concentrated under reduced pressure, and the resulting residues were purified by thin layer chromatography with developing solvent system A to obtain the title product 22 (15 mg, brown solid), yield: 12.7%.

MS m/z (ESI): 427.4 [M+1].

$^1$H NMR (400 MHz, CD$_3$OD) δ 8.30 (d, 1H), 7.82-7.79 (m, 1H), 7.00 (m, 1H), 6.69-6.67 (m, 1H), 6.55-6.50 (m, 1H), 6.25 (d, 1H), 4.48-4.45 (m, 1H), 4.37-4.30 (m, 4H), 4.06-3.97 (m, 7H), 3.30-3.25 (m, 5H).

Example 23

5-Fluoro-1-(1-(5-(methoxymethyl)-4-(6-methoxypyridin-3-yl)-4H-1,2,4-triazol-3-yl) azetidin-3-yl) indoline 23

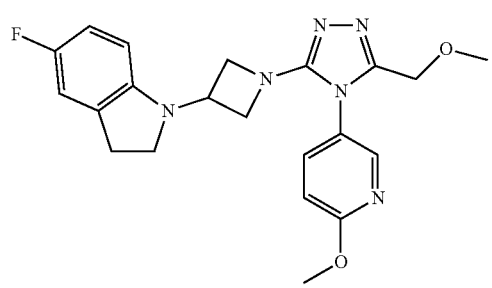

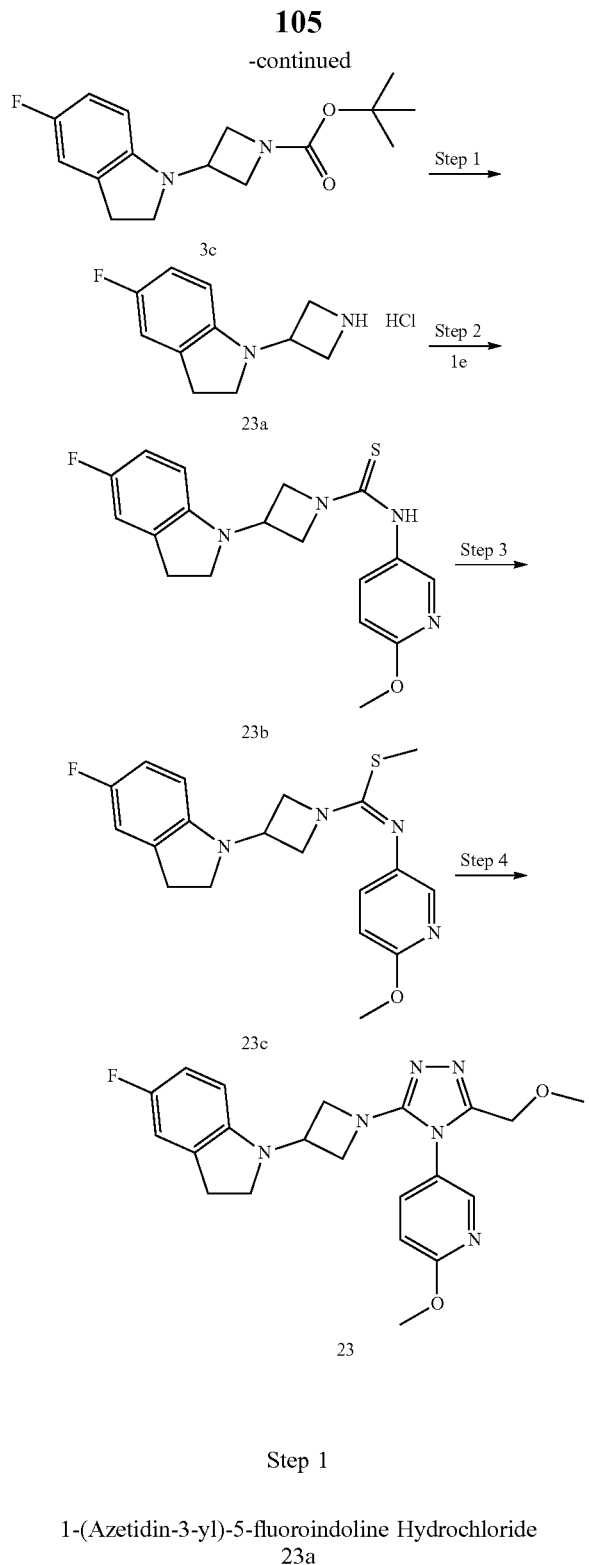

Step 1

1-(Azetidin-3-yl)-5-fluoroindoline Hydrochloride 23a

Compound 3c (0.48 g, 1.64 mmol) and 3 mL solution of hydrogen chloride in 1,4-dioxane (4 M) were dissolved in 10 mL of dichloromethane, and reacted for 12 hours after addition. The reaction solution was concentrated under reduced pressure to obtain the crude title product 23a (588 mg, yellow solid), which was used directly in the next step without purification.

MS m/z (ESI): 193.1 [M+1].

Step 2

3-(5-Fluoroindolin-1-yl)-N-(6-methoxypyridin-3-yl) azetidine-1-carbothioamide 23b The crude product 23a (400 mg, 1.64 mmol) and compound 1e (272 mg, 1.64 mmol) were dissolved in 20 mL of tetrahydrofuran successively, and stirred for 3 hours after addition. The reaction solution was then warmed up to 50° C. and reacted for 12 hours. The reaction solution was concentrated under reduced pressure to obtain the crude title product 23b (588 mg, black solid), which was used directly in the next step without purification.

MS m/z (ESI): 359.2 [M+1].

Step 3

Methyl (E)-3-(5-fluoroindolin-1-yl)-N-(6-methoxypyridin-3-yl)azetidine-1-carbimidothioate 23c The crude product 23b (500 mg, 1.64 mmol) was dissolved in 15 mL of tetrahydrofuran, and cooled to 0° C. The above solution was added with potassium tert-butoxide (550 mg, 4.92 mmol), and reacted for 2 hours after addition. The reaction solution was then added with methyl 4-methylbenzenesulfonate (0.46 g, 2.46 mmol), and reacted for 12 hours. The reaction solution was concentrated under reduced pressure, and the resulting residues were purified by thin layer chromatography with developing solvent system C to obtain the title product 23c (20 mg, yellow solid), yield: 3.0%.

MS m/z (ESI): 372.1 [M+1].

Step 4

5-Fluoro-1-(1-(5-(methoxymethyl)-4-(6-methoxypyridin-3-yl)-4H-1,2,4-triazol-3-yl) azetidin-3-yl) indoline 23

Compound 23c (20 mg, 53.7 μmol), 2-methoxyacetylhydrazine (6 mg, 0.51 μmol) and three drops of trifluoroacetic acid were dissolved in 10 mL of tetrahydrofuran successively. After addition, the reaction solution was heated to 70° C. and reacted for 2 hours. The reaction solution was concentrated under reduced pressure, and the resulting residues were purified by thin layer chromatography with developing solvent system A to obtain the title product 23 (5 mg, yellow oil), yield: 22.7%.

MS m/z (ESI): 411.2 [M+1].

$^1$H NMR (400 MHz, CD$_3$OD) δ 8.29 (s, 1H), 7.80 (d, 1H), 6.97 (d, 1H), 6.84 (d, 1H), 6.71 (d, 1H), 6.30 (d, 1H), 4.36 (d, 1H), 4.32 (s, 2H), 4.25 (t, 1H), 3.97-4.00 (m, 6H), 3.46 (t, 2H), 3.29 (s, 3H), 2.92 (t, 2H).

107

Example 24

7-Fluoro-4-(1-(5-(methoxymethyl)-4-(6-methoxy-pyridin-3-yl)-4H-1,2,4-triazol-3-yl) azetidin-3-yl)-3,4-dihydro-2H-benzo[b][1,4]oxazine 24

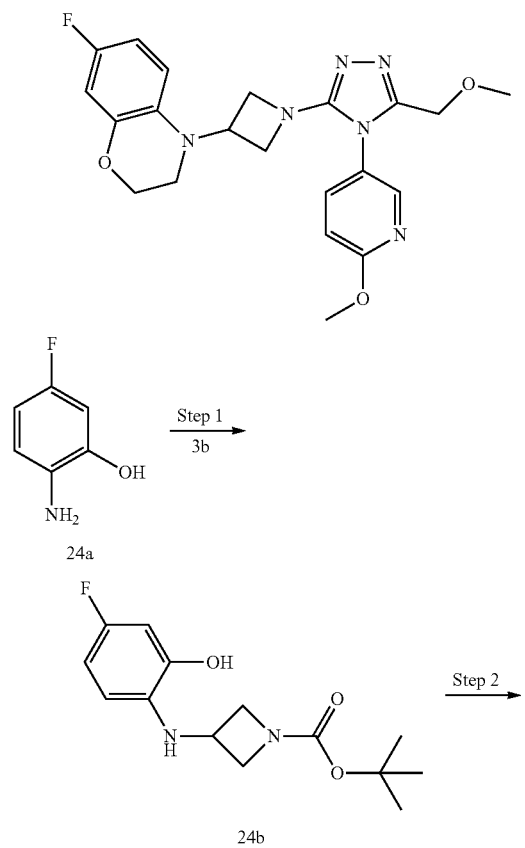

108

-continued

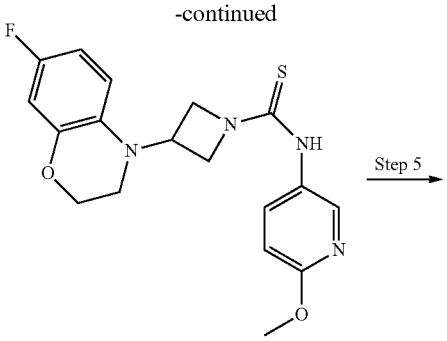

Step 1

Tert-butyl 3-((4-fluoro-2-hydroxyphenyl)amino)azetidine-1-carboxylate 24b

2-Amino-5-fluorophenol 24a (1000 mg, 7.87 mmol), sodium triacetoxyborohydride (1667.24 mg, 7.87 mmol) and compound 3b (1346.68 mg, 7.87 mmol) were dissolved in 60 mL of dichloromethane, and reacted for 12 hours after addition. The reaction solution was added with 50 mL of water, extracted with dichloromethane (50 mL×2), and washed. The organic phases were combined, dried over anhydrous sodium sulfate, and filtered. The filtrate was concentrated under reduced pressure to obtain the crude title product 24b (1500 mg, brown paste), which was used directly in the next step without purification.

MS m/z (ESI): 283.2 [M+1].

Step 2

Tert-butyl 3-(7-fluoro-2H-benzo[b][1,4]oxazin-4(3H)-yl)azetidine-1-carboxylate 24c The crude product 24b (1000 mg, 3.54 mmol), 1,2-dibromoethane (1330.88 mg, 7.08 mmol) and potassium carbonate (979.14 mg, 7.08 mmol) were dissolved in 50 mL of N,N-dimethylformamide. After addition, the reaction solution was reacted at 90° C. for 12 hours. The reaction solution was concentrated under reduced pressure, and the residues were added with 100 mL of water and extracted with dichloromethane (100 mL×3). The organic phases were combined, dried over anhydrous sodium sulfate, and filtered. The filtrate was concentrated under reduced pressure, and the resulting residues were purified by thin layer chromatography with developing solvent system C to obtain the title product 24c (700 mg, brown solid), yield: 54.5%.

MS m/z (ESI): 309.2 [M+1].

Step 3

4-(Azetidin-3-yl)-7-fluoro-3,4-2H-benzo[b][1,4]oxazine hydrochloride 24d

Compound 24c (600 mg, 1.95 mmol) and 4.86 mL solution of hydrogen chloride in 1,4-dioxane (4 M) were dissolved in 5 mL of dichloromethane, and reacted for 3 hours after addition. The reaction solution was concentrated under reduced pressure to obtain the crude title product 24d (900 mg, black solid), which was used directly in the next step without purification.

MS m/z (ESI): 209.2 [M+1].

Step 4

3-(7-Fluoro-2H-benzo[b][1,4]oxazin-4(3H)-yl)-N-(6-methoxypyridin-3-yl)azetidine-1-carbothioamide 24e The crude product 24d (500 mg, 2.40 mmol) and compound 1e (399.08 mg, 2.40 mmol) were dissolved in 50 mL of tetrahydrofuran successively, and reacted for 3 hours after addition. The reaction solution was concentrated under reduced pressure to obtain the crude title product 24e (600 mg, black solid), which was used directly in the next step without purification.

MS m/z (ESI): 375.4 [M+1].

Step 5

Methyl (E)-3-(7-Fluoro-2H-benzo[b][1,4]oxazin-4(3H)-yl)-N-(6-methoxypyridin-3-yl)azetidine-1-carbimidothioate 24f The crude product 24e (250 mg, 0.67 mmol) and potassium tert-butoxide (149.84 mg, 1.34 mmol) were dissolved in 30 mL of tetrahydrofuran, and cooled to 0° C. and reacted for 1 hour after addition. The reaction solution was then added with methyl 4-methylbenzenesulfonate (249.68 mg, 1.34 mmol), and then slowly warmed up to room temperature, and reacted for 12 hours. The reaction solution was poured into 25 mL of water, and extracted with dichloromethane (30 mL×3). The organic phases were combined, dried over anhydrous sodium sulfate, and filtered. The filtrate was concentrated under reduced pressure, and the resulting residues were purified by thin layer chromatography with developing solvent system C to obtain the title product 24f (100 mg, yellow oil), yield: 30.8%.

MS m/z (ESI): 389.2 [M+1].

Step 6

7-Fluoro-4-(1-(5-(methoxymethyl)-4-(6-methoxypyridin-3-yl)-4H-1,2,4-triazol-3-yl) azetidin-3-yl)-3,4-dihydro-2H-benzo[b][1,4]oxazine 24

Compound 24f (900 mg, 2.32 mmol), 2-methoxyacetylhydrazine (482.41 mg, 4.62 mmol) and trifluoroacetic acid (528.33 mg, 4.63 mmol) were dissolved in 40 mL of tetrahydrofuran successively. After addition, the reaction solution was heated to 65° C. and reacted for 3 hours. The reaction solution was concentrated under reduced pressure, and the resulting residues were purified by HPLC to obtain the title product 24 (220 mg, yellow solid), yield: 21.8%.

MS m/z (ESI): 427.4 [M+1].

$^1$H NMR (400 MHz, CD$_3$OD) δ 8.30 (d, 1H), 7.83-7.80 (m, 1H), 7.00 (d, 1H), 6.51-6.47 (m, 2H), 6.39-6.36 (m, 1H), 4.35-4.29 (m, 5H), 4.04-4.00 (m, 5H), 3.98-3.94 (m, 2H), 3.26 (s, 3H), 3.16-3.14 (m, 2H).

Example 25

5-Fluoro-1-(1-(5-(methoxymethyl)-4-(6-methoxypyridin-3-yl)-4H-1,2,4-triazol-3-yl) azetidin-3-yl)-1H-indole 25

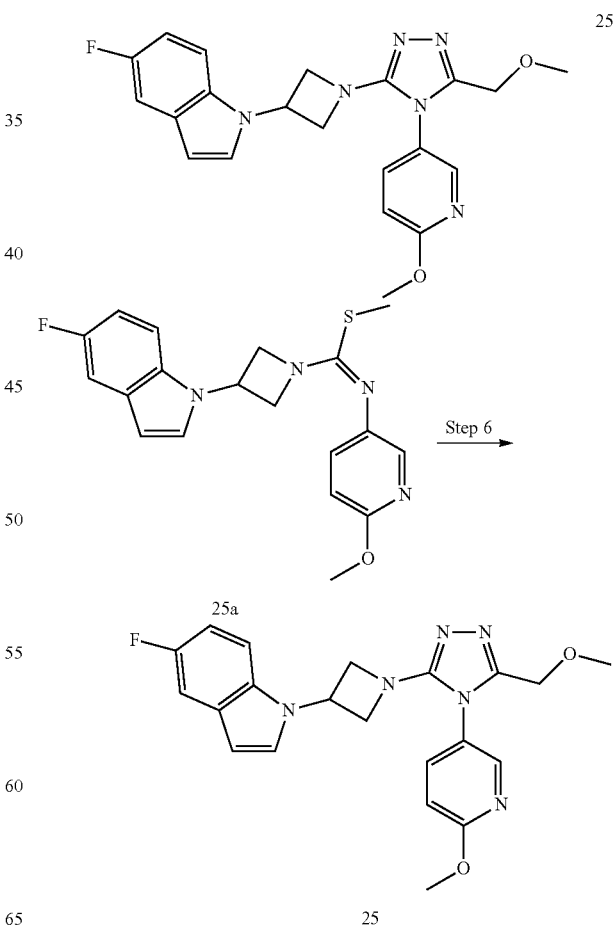

The synthetic route of Example 5 was applied except that the starting material 5a in Step 1 was replaced with compound 3a, to obtain the product methyl (E)-3-(5-fluoro-1H-indol-1-yl)-N-(6-methoxypyridin-3-yl)azetidine-1-carbimidothioate 25a (76 mg, yellow solid) in Step 5, yield: 23%.

MS m/z (ESI): 371.2 [M+1].

Compound 25a (76 mg, 0.205 mmol), 2-methoxyacetylhydrazine (21 mg, 0.205 mmol) and 0.05 mL of trifluoroacetic acid were dissolved in 15 mL of tetrahydrofuran. After addition, the reaction solution was heated to 70° C. and reacted for 2 hours. The reaction solution was concentrated under reduced pressure, and the resulting residues were purified by thin layer chromatography with developing solvent system A to obtain the title product 25 (15 mg, yellow oil), yield: 18%.

MS m/z (ESI): 409.4 [M+1].

$^1$H NMR (400 MHz, CD$_3$OD) δ 8.33 (d, 1H), 7.85 (d, 1H), 7.53 (d, 1H), 7.43 (d, 1H), 7.22 (d, 1H), 6.98 (d, 1H), 6.94 (t, 1H), 6.52 (d, 1H), 5.35-5.45 (m, 1H), 4.33-4.39 (m, 4H), 4.15 (d, 2H), 3.98 (s, 3H), 3.28 (s, 3H).

Example 26

1-(1-(5-(Ethoxymethyl)-4-(6-methoxypyridin-3-yl)-4H-1,2,4-triazol-3-yl)azetidin-3-yl)-6-fluoro-1,2,3,4-tetrahydroquinoline 26

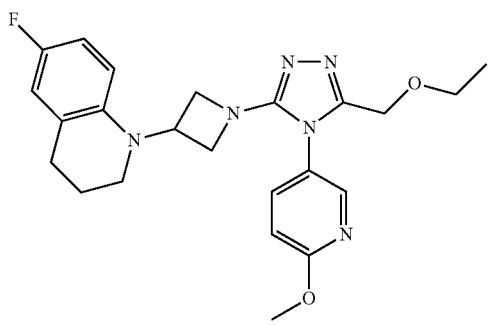

26

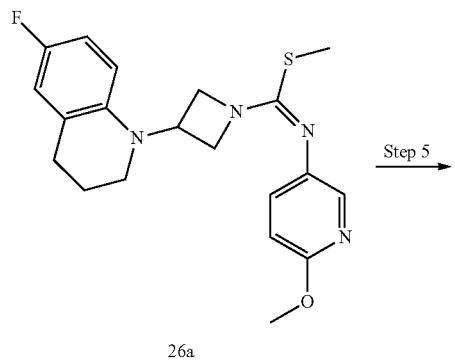

26a

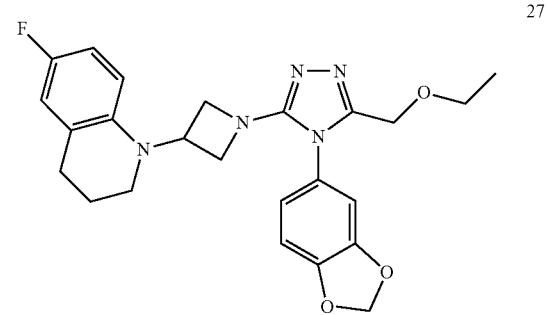

26

The synthetic route of Example 19 was applied except that the starting material 19a in Step 1 was replaced with 6-fluoro-1,2,3,4-tetrahydroquinoline, to obtain the product methyl (E)-3-(6-fluoro-3,4-dihydroquinolin-1(2H)-yl)-N-(6-methoxypyridin-3-yl)azetidine-1-carbimidothioate 26a (500 mg, brown oil) in Step 4, yield: 26.77%.

MS m/z (ESI): 387.1 [M+1].

Compound 26a (200 mg, 0.52 mmol), 2-ethoxyacetylhydrazine (61.13 mg, 0.52 mmol) and 0.1 mL of trifluoroacetic acid were dissolved in 30 mL of tetrahydrofuran, and reacted under reflux for 3 hours. The reaction solution was concentrated under reduced pressure, and the resulting residues were purified by thin layer chromatography with developing solvent system A to obtain the title product 26 (50 mg, white solid), yield: 20.93%.

MS m/z (ESI): 439.2 [M+1].

$^1$H NMR (400 MHz, CD$_3$OD) δ 8.29 (d, 1H), 7.79-7.82 (m, 1H), 6.98 (d, 1H), 6.69-6.75 (m, 2H), 6.27-6.30 (m, 1H), 4.34-4.38 (m, 3H), 3.91-4.03 (m, 7H), 3.34-3.40 (m, 2H), 3.07 (t, 2H), 2.71 (t, 2H), 1.91-1.96 (m, 2H), 1.07-1.10 (t, 3H).

Example 27

1-(1-(4-(Benzo[d][1,3]dioxolan-5-yl)-5-(ethoxymethyl)-4H-1,2,4-triazol-3-yl)azetidin-3-yl)-6-fluoro-1,2,3,4-tetrahydroquinoline 27

113
-continued

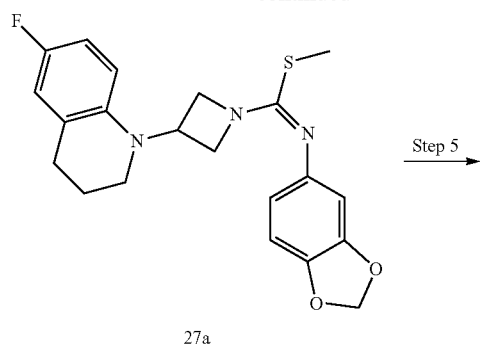

27a

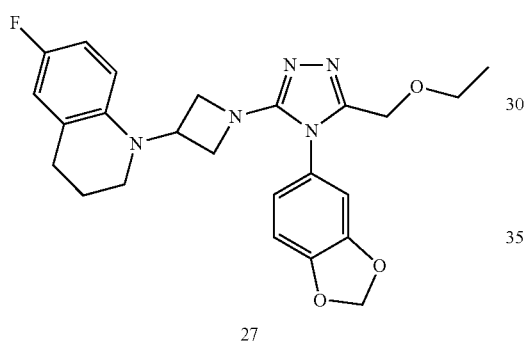

27

The synthetic route of Example 19 was applied except that the starting material 19a in Step 1 was replaced with 6-fluoro-1,2,3,4-tetrahydroquinoline and the compound 1e in Step 3 was replaced with compound 3g, to obtain the product methyl (E)-N-benzo[d][1,3]dioxolan-5-yl-3-(6-fluoro-3,4-dihydroquinolin-1(2H)-yl)azetidine-1-carbimidothioate 27a (200 mg, yellow solid) in Step 4, yield: 48.25%.

MS m/z (ESI): 400.1 [M+1].

Compound 27a (200 mg, 0.5 mmol), 2-ethoxyacetylhydrazine (88.71 mg, 0.75 mmol) and 0.1 mL of trifluoroacetic acid were dissolved in 20 mL of tetrahydrofuran, heated to 70° C. and stirred to react for 2 hours. The reaction solution was concentrated under reduced pressure, and the resulting residues were purified by HPLC to obtain the title product 27 (20 mg, yellow solid), yield: 8.28%.

MS m/z (ESI): 452.2 [M+1].

$^1$H NMR (400 MHz, DMSO-$d_6$) δ 6.94-6.89 (m, 3H), 6.89-6.73 (m, 2H), 6.22-6.20 (m, 1H), 6.14 (s, 2H), 4.40 (s, 2H), 4.38-4.34 (m, 1H), 4.03-3.97 (m, 4H), 3.55-3.50 (m, 2H), 3.12-3.09 (m, 2H), 2.75-2.72 (m, 2H), 1.99-1.93 (m, 2H), 1.19-1.16 (t, 3H).

114
Example 28

1-(1-(4-(Benzo[d][1,3]dioxolan-5-yl)-5-(methoxymethyl)-4H-1,2,4-triazol-3-yl)azetidin-3-yl)-6-fluoro-1,2,3,4-tetrahydroquinoline 28

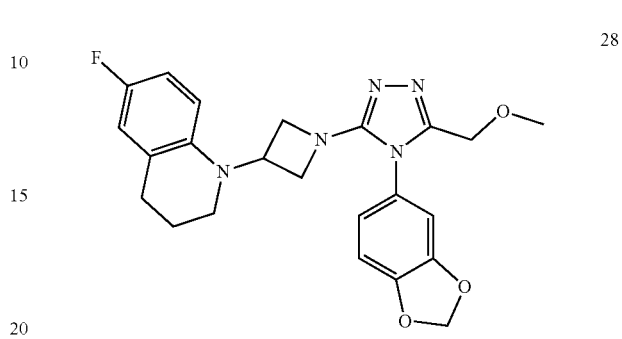

28

The synthetic route of Example 19 was applied except that the starting material 19a in Step 1 was replaced with 6-fluoro-1,2,3,4-tetrahydroquinoline and the compound 1e in Step 3 was replaced with compound 3g, to obtain the title product 28 (8 mg, pale yellow solid) was prepared.

MS m/z (ESI): 438.1 [M+1].

$^1$H NMR (400 MHz, CDCl$_3$) δ 6.93-6.89 (m, 3H), 6.76-6.70 (m, 2H), 6.15-6.11 (m, 3H), 4.49-4.45 (m, 1H), 4.15-4.09 (m, 4H), 4.08-4.04 (m, 2H), 3.29 (s, 3H), 3.10-3.07 (m, 2H), 2.72-2.69 (m, 2H), 1.97-1.91 (m, 2H).

Example 29

6-Fluoro-1-(1-(4-(6-methoxypyridin-3-yl)-5-methyl-4H-1,2,4-triazol-3-yl)azetidin-3-yl)-1,2,3,4-tetrahydroquinoline 29

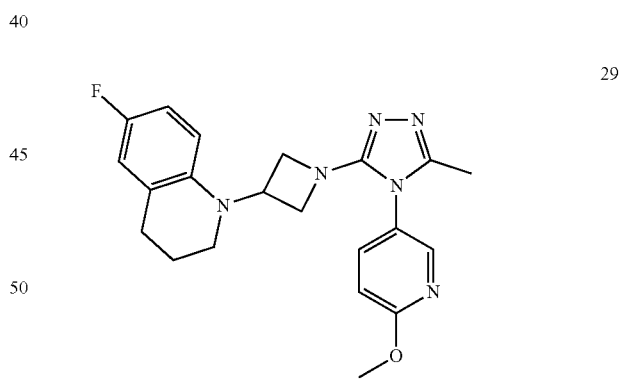

29

The synthetic route of Example 19 was applied except that the starting material 19a in Step 1 was replaced with 6-fluoro-1,2,3,4-tetrahydroquinoline and the starting material 2-methoxyacetylhydrazine in Step 5 was replaced with acetylhydrazine, to obtain the title product 29 (10 mg, white solid).

MS m/z (ESI): 395.2 [M+1].

$^1$H NMR (400 MHz, CD$_3$OD) δ 8.27 (d, 1H), 7.80-7.77 (m, 1H), 7.02 (d, 1H), 6.75-6.72 (m, 2H), 6.30-6.27 (m, 1H), 4.37-4.33 (m, 1H), 4.01-3.98 (m, 5H), 3.93-3.90 (m, 2H), 3.07-3.04 (m, 2H), 2.72-2.69 (m, 2H), 2.19 (s, 3H), 1.94-1.91 (m, 2H).

Example 30

6-Fluoro-1-(1-(5-(methoxymethyl)-4-(6-methoxy-pyridin-3-yl)-4H-1,2,4-triazol-3-yl) azetidin-3-yl)-1,2,3,4-tetrahydroquinoline 30

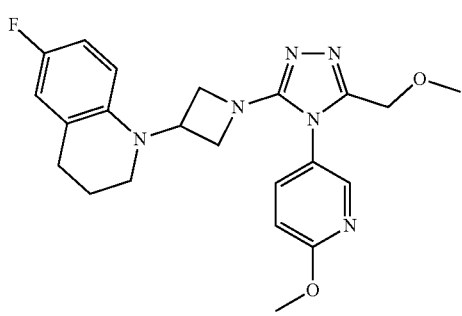

The synthetic route of Example 19 was applied except that the starting material 19a in Step 1 was replaced with 6-fluoro-1,2,3,4-tetrahydroquinoline, to obtain the title product 30 (20 mg, brown solid).

MS m/z (ESI): 425.2 [M+1].

$^1$H NMR (400 MHz, CD$_3$OD) δ 8.29 (d, 1H), 7.78-7.81 (m, 1H), 6.97 (d, 1H), 6.70-6.73 (m, 2H), 6.27-6.30 (m, 1H), 4.329-4.38 (m, 3H), 3.91-4.04 (m, 7H), 3.25 (s, 3H), 3.05 (t, 2H), 2.70 (t, 2H), 1.90-1.96 (m, 2H).

Example 31

4-(1-(5-(Ethoxymethyl)-4-(6-methoxypyridin-3-yl)-4H-1,2,4-triazol-3-yl)azetidin-3-yl)-7-fluoro-3,4-dihydro-2H-benzo[b][1,4]oxazine 31

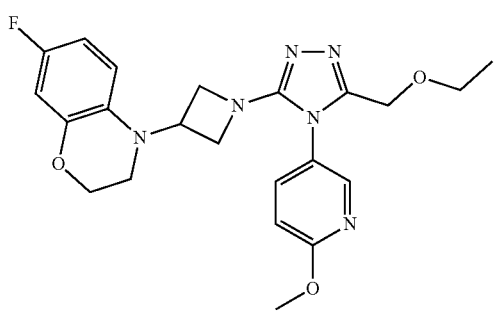

The synthetic route of Example 24 was applied except that the starting material 2-methoxyacetylhydrazine in Step 6 was replaced with 2-ethoxyacetylhydrazine, to obtain the title product 31 (25 mg, brown paste).

MS m/z (ESI): 441.4 [M+1].

$^1$H NMR (400 MHz, CD$_3$OD) δ 8.31 (d, 1H), 7.83-7.80 (m, 1H), 7.00 (d, 1H), 6.51-6.47 (m, 2H), 6.39-6.36 (m, 1H), 4.35-4.30 (m, 5H), 4.02-4.00 (m, 5H), 3.97-3.63 (m, 2H), 3.47-3.40 (m, 2H), 3.16-3.14 (m, 2H), 1.11-1.08 (m, 3H).

Example 32

7-Fluoro-4-(1-(4-(6-methoxypyridin-3-yl)-5-methyl-4H-1,2,4-triazol-3-yl)azetidin-3-yl)-3,4-dihydro-2H-benzo[b][1,4]oxazine 32

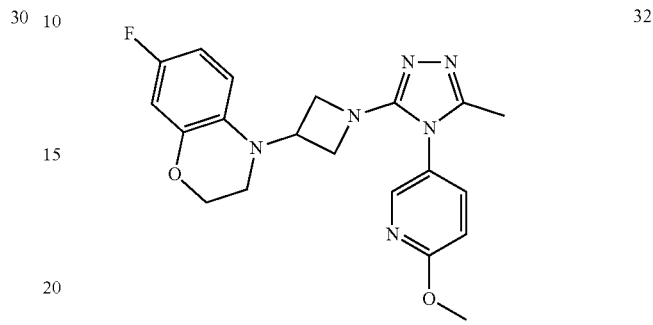

The synthetic route of Example 24 was applied except that the starting material 2-methoxyacetylhydrazine in Step 6 was replaced with acetylhydrazine, to obtain the title product 32 (25 mg, brown paste).

MS m/z (ESI): 397.4 [M+1].

$^1$H NMR (400 MHz, CD$_3$OD) δ 8.28 (d, 1H), 7.80-7.77 (m, 1H), 7.00 (d, 1H), 6.51-6.47 (m, 2H), 6.39-6.36 (m, 1H), 4.31-4.28 (m, 3H), 4.02-4.00 (m, 5H), 3.97-3.63 (m, 2H), 3.16-3.14 (m, 2H), 2.20 (s, 3H).

Example 33

5-Fluoro-1-(1-(5-(methoxymethyl)-4-(6-methoxy-pyridin-3-yl)-4H-1,2,4-triazol-3-yl) azetidin-3-yl)-1H-indazole 33

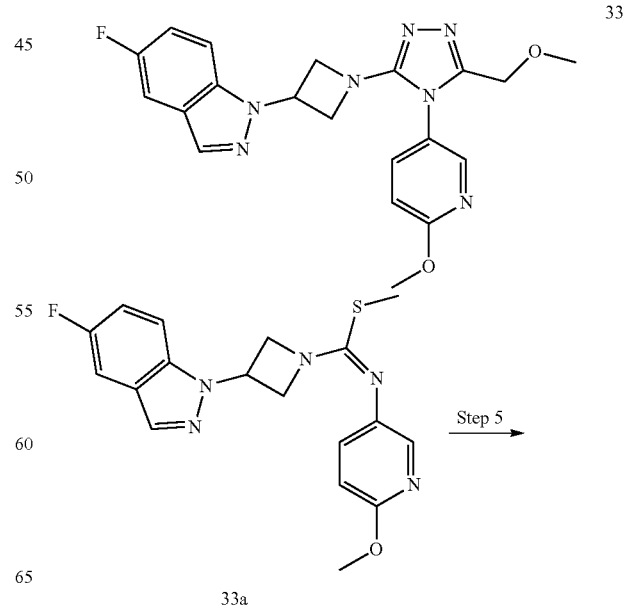

-continued

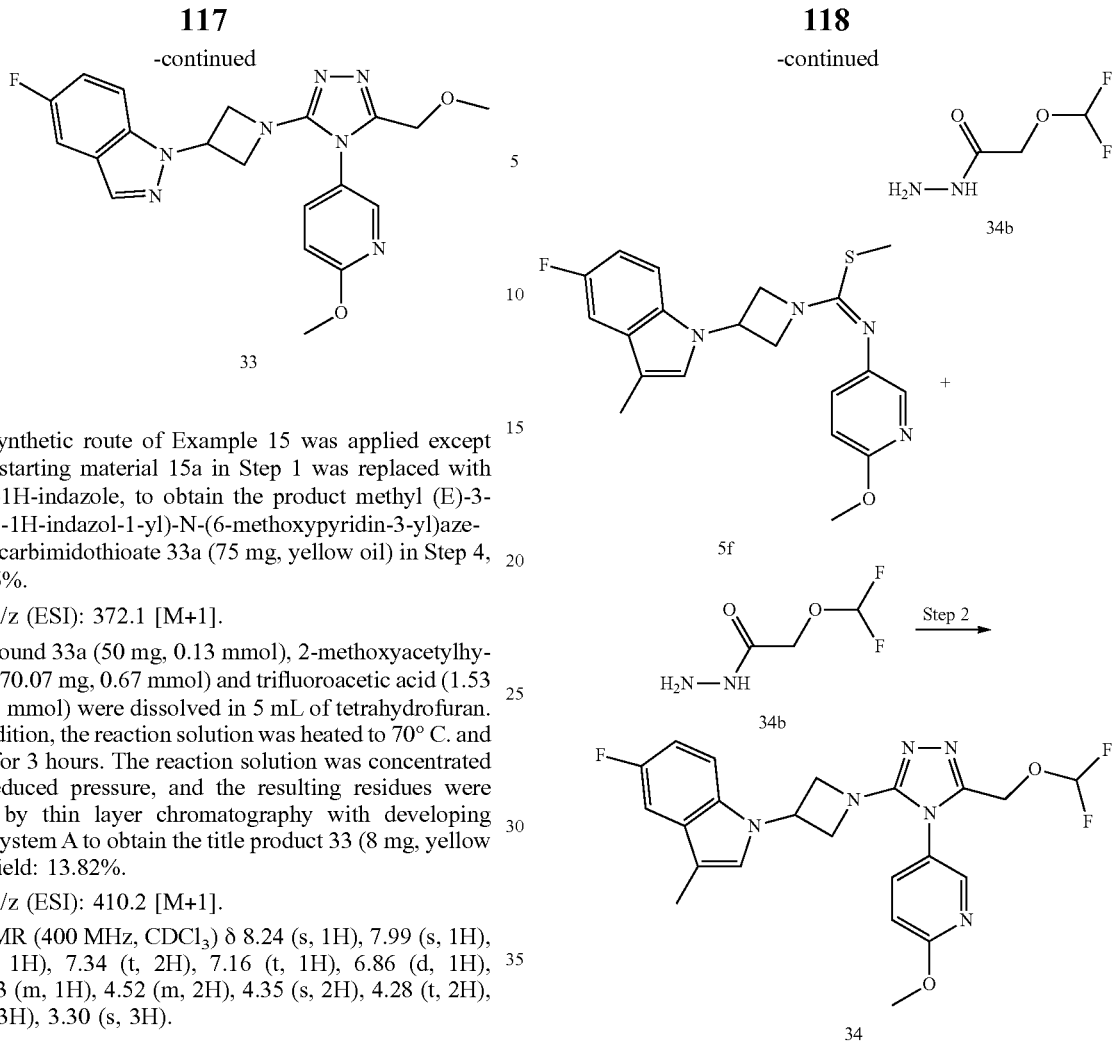

The synthetic route of Example 15 was applied except that the starting material 15a in Step 1 was replaced with 5-fluoro-1H-indazole, to obtain the product methyl (E)-3-(5-fluoro-1H-indazol-1-yl)-N-(6-methoxypyridin-3-yl)azetidine-1-carbimidothioate 33a (75 mg, yellow oil) in Step 4, yield: 26%.

MS m/z (ESI): 372.1 [M+1].

Compound 33a (50 mg, 0.13 mmol), 2-methoxyacetylhydrazine (70.07 mg, 0.67 mmol) and trifluoroacetic acid (1.53 mg, 0.01 mmol) were dissolved in 5 mL of tetrahydrofuran. After addition, the reaction solution was heated to 70° C. and reacted for 3 hours. The reaction solution was concentrated under reduced pressure, and the resulting residues were purified by thin layer chromatography with developing solvent system A to obtain the title product 33 (8 mg, yellow solid), yield: 13.82%.

MS m/z (ESI): 410.2 [M+1].

$^1$H NMR (400 MHz, CDCl$_3$) δ 8.24 (s, 1H), 7.99 (s, 1H), 7.65 (d, 1H), 7.34 (t, 2H), 7.16 (t, 1H), 6.86 (d, 1H), 5.45-5.43 (m, 1H), 4.52 (m, 2H), 4.35 (s, 2H), 4.28 (t, 2H), 3.97 (s, 3H), 3.30 (s, 3H).

Example 34

1-(1-(5-((Difluoromethoxy)methyl)-4-(6-methoxypyridin-3-yl)-4H-1,2,4-triazol-3-yl) azetidin-3-yl)-5-fluoro-3-methyl-1H-indole 34

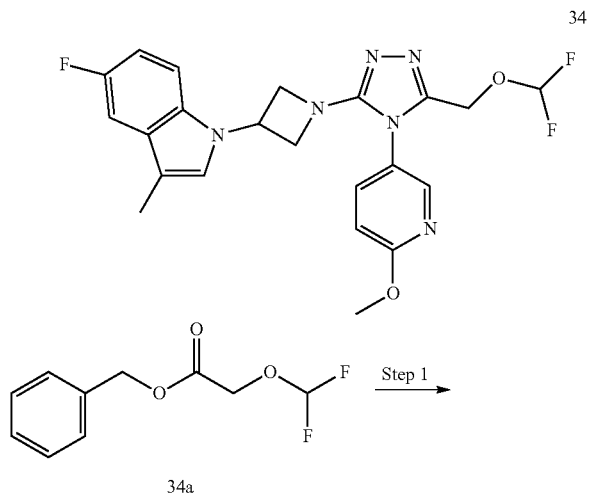

Step 1

2-(Difluoromethoxy)acetylhydrazine 34b

The crude product benzyl 2-(difluoromethoxy)acetate 34a (140 mg, 1.67 mmol, prepared according to the method disclosed in the patent application "WO2015180612") and hydrazine hydrate (85%, 57.2 mg) were added to 3 mL of ethanol. The reaction solution was added to a sealed tube, and stirred at 80° C. for 15 hours. After stopping heating, the reaction solution was concentrated under reduced pressure to obtain the crude title product 34b (100 mg), which was used directly in the next step without purification.

MS m/z (ESI): 141.1 [M+1].

Step 2

1-(1-(5-((Difluoromethoxy)methyl)-4-(6-methoxypyridin-3-yl)-4H-1,2,4-triazol-3-yl) azetidin-3-yl)-5-fluoro-3-methyl-1H-indole 34

The synthetic route of Example 5 was applied except that the starting material 2-ethoxyacetylhydrazine in Step 6 was replaced with compound 34b, to obtain the title product 34 (10 mg, white solid).

MS m/z (ESI): 459.2 [M+1].

¹H NMR (400 MHz, CD₃OD) δ 8.34 (d, 1H), 7.85-7.83 (m, 1H), 7.36-7.17 (m, 2H) 7.16-7.14 (m, 1H), 6.99 (d, 1H), 6.97-6.91 (m, 1H), 6.39 (t, 1H), 5.37-5.33 (m, 1H), 4.84 (s, 2H), 4.36-4.32 (m, 2H), 4.15-4.13 (m, 2H), 3.98 (s, 3H), 2.26 (s, 3H).

Example 35

4-(1-(5-(Difluoromethyl)-4-(6-methoxypyridin-3-yl)-4H-1,2,4-triazol-3-yl)azetidin-3-yl)-7-fluoro-3,4-dihydro-2H-benzo[b][1,4]oxazine 35

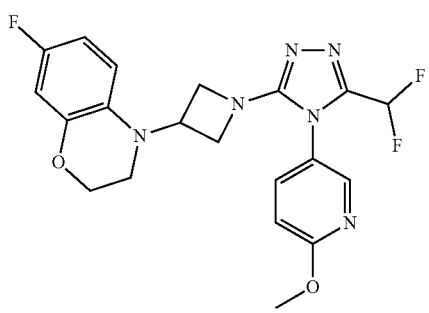

35

The synthetic route of Example 24 was applied except that the starting material 2-methoxyacetylhydrazine (Shanghai Bide Pharmatech Ltd.) in Step 6 was replaced with 2,2-difluoroacetylhydrazine, to obtain the title product 35 (20 mg, white solid).

MS m/z (ESI): 433.2 [M+1].

¹H NMR (400 MHz, CD₃OD) δ 8.26 (d, 1H), 7.63-7.60 (m, 1H), 6.94 (d, 1H), 6.78 (s, 1H), 6.60-6.58 (m, 1H), 6.57-6.52 (m, 1H), 6.24-6.21 (m, 1H), 4.36-4.17 (m, 3H), 4.06 (s, 3H), 4.04-4.02 (m, 4H), 3.17-3.15 (m, 2H).

Example 36

Methyl ((5-(3-(6-fluoro-3,4-dihydroquinolin-1(2H)-yl)azetidin-1-yl)-4-(6-methoxypyridin-3-yl)-4H-1,2,4-triazol-3-yl)methyl)carbamate 36

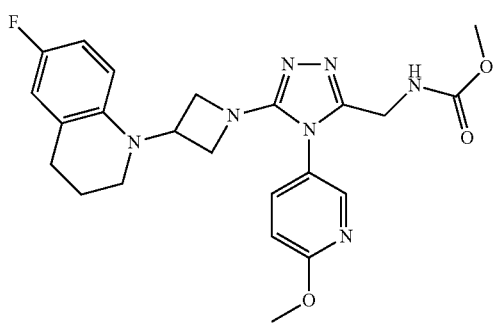

36

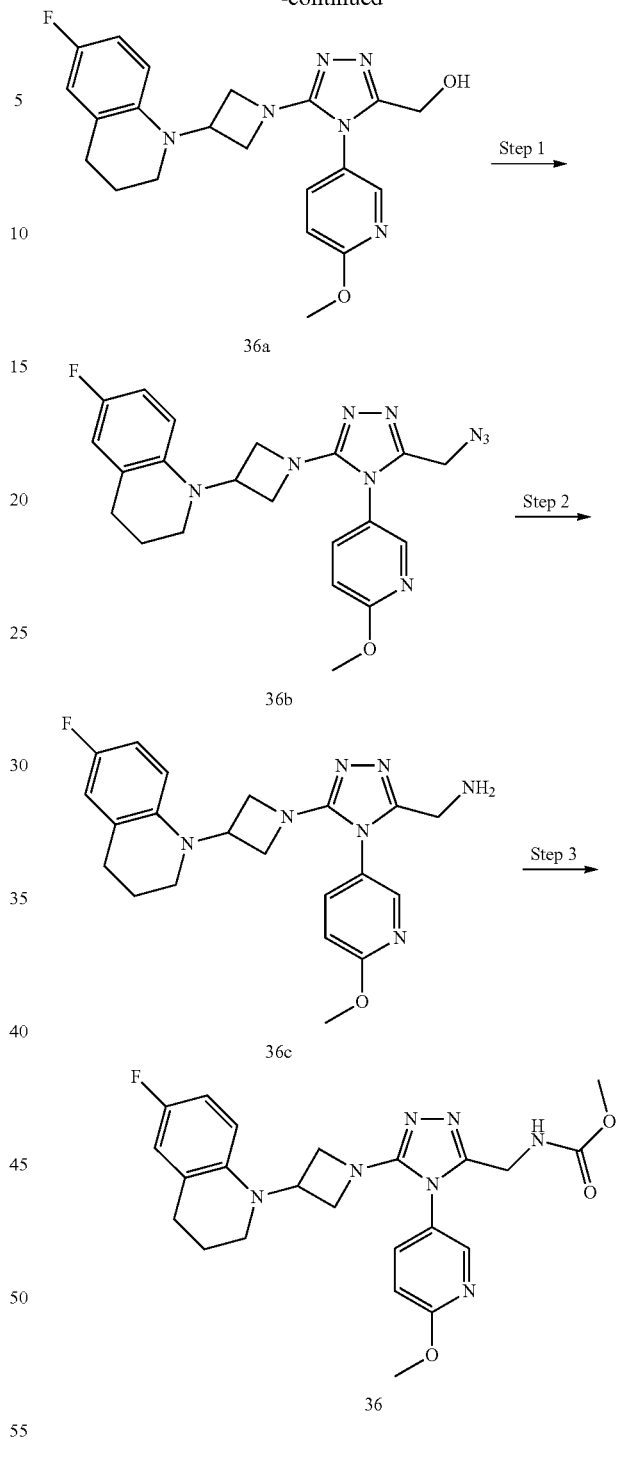

Step 1

1-(1-(5-(Azidomethyl)-4-(6-methoxypyridin-3-yl)-4H-1,2,4-triazol-3-yl)azetidin-3-yl)-6-fluoro-1,2,3,4-tetrahydroquinoline 36b The synthetic route of Example 26 was applied except that the starting material 2-methoxyacetylhydrazine was replaced with hydroxymethylacetylhydrazine (Shanghai Bide Pharmatech Ltd.), to obtain (5-(3-(6-fluoro-3,4-dihydro quinolin-1 (2H)-yl)azetidin-1-yl)-4-(6-methoxypyridin-3-yl)-4H-1,2,4-triazol-3-yl)methanol 36a. 36a (200 mg, 0.48 mmol) and triethylamine (101 mg, 1 mmol) were dissolved in 10 mL of dichloromethane. The above reaction solution was added with methylsulfonyl chloride (58 mg, 0.5 mmol) in an ice bath, and then slowly warmed up to room temperature, and reacted for 3 hours. The reaction solution was concentrated under reduced pressure until dryness, and the residues were dissolved in 10 mL of N,N-dimethylformamide and added with sodium azide (65 mg, 1 mmol). The reaction solution was poured into 30 mL of water, extracted with ethyl acetate (30 mL×3), and washed with saturated sodium chloride solution (30 mL×2). The organic phases were combined, dried over anhydrous sodium sulfate, and filtered. The filtrate was concentrated under reduced pressure to obtain the title product 36b (165 mg, white solid), yield: 75.3%.

MS m/z (ESI): 436.1 [M+1].

Step 2

(5-(3-(6-Fluoro-3,4-dihydroquinolin-1(2H)-yl)azetidin-1-yl)-4-(6-methoxypyridin-3-yl)-4H-1,2,4-triazol-3-yl)methylamine 36c Compound 36b (130 mg, 0.3 mmol) was dissolved in 10 mL of methanol, and added with 10% Pd/C (300 mg, 0.3 mmol). The reaction system was purged with hydrogen three times, and the reaction solution was reacted under hydrogen atmosphere for 3 hours. The reaction solution was filtered, and the filtrate was concentrated under reduced pressure to obtain the crude title product 36c (130 mg, white solid), yield: 100%.

MS m/z (ESI): 410.2[M+1].

Step 3

Methyl (5-(3-(6-fluoro-3,4-dihydroquinolin-1(2H)-yl)azetidin-1-yl)-4-(6-methoxypyridin-3-yl)-4H-1,2,4-triazol-3-yl)methyl)carbamate 36

Compound 36c (41 mg, 0.1 mmol) and triethylamine (20.2 mg, 0.2 mmol) were dissolved in 10 mL of dichloromethane. The above reaction solution was added with methyl chloroformate (58 mg, 0.5 mmol) in an ice bath, and then slowly warmed up to room temperature, and reacted for 3 hours. The reaction solution was poured into 30 mL of water, extracted with dichloromethane (20 mL×3), and washed with saturated sodium chloride solution (30 mL×2). The organic phases were combined, dried over anhydrous sodium sulfate, and filtered. The filtrate was concentrated under reduced pressure, and the resulting residues were purified by HPLC to obtain the title product 36 (10 mg, white solid), yield: 21.3%.

MS m/z (ESI): 468.2[M+1].

$^1$H NMR (400 MHz, CD$_3$OD) δ 8.25 (d, 1H), 7.77-7.74 (m, 1H), 6.96 (d, 1H), 6.74-6.69 (m, 2H), 6.29-6.26 (m, 1H), 4.35-4.31 (m, 1H), 4.25 (s, 2H), 4.03-3.97 (m, 7H), 3.53 (s, 3H), 3.07 (t, 2H), 2.70 (t, 2H), 2.03-1.91 (m, 2H).

Example 37

4-(1-(5-((Difluoromethoxy)methyl)-4-(6-methoxypyridin-3-yl)-4H-1,2,4-triazol-3-yl) azetidin-3-yl)-7-fluoro-3,4-dihydro-2H-benzo[b][1,4]oxazine 37

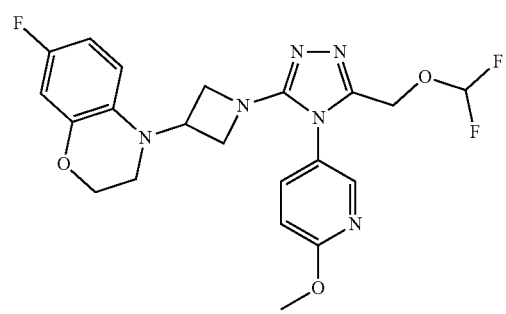

37

The synthetic route of Example 24 was applied except that the starting material 2-methoxyacetylhydrazine in Step 6 was replaced with compound 34b, to obtain the title product 37 (20 mg, white solid).

MS m/z (ESI): 463.2 [M+1].

$^1$H NMR (400 MHz, CD$_3$OD) δ 8.23 (d, 1H), 7.61-7.59 (m, 1H), 6.95 (d, 1H), 6.60-6.57 (m, 1H), 6.52-6.50 (m, 1H), 6.25-6.21 (m, 2H), 4.82 (s, 2H), 4.35-4.28 (m, 3H), 4.06 (s, 3H), 4.03-4.01 (m, 4H), 3.18-3.16 (m, 2H).

Example 38

5-(3-((Difluoromethoxy)methyl)-5-(3-(6-fluoronaphthalen-1-yl)azetidin-1-yl)-4H-1,2,4-triazol-4-yl)-2-methoxypyridine 38

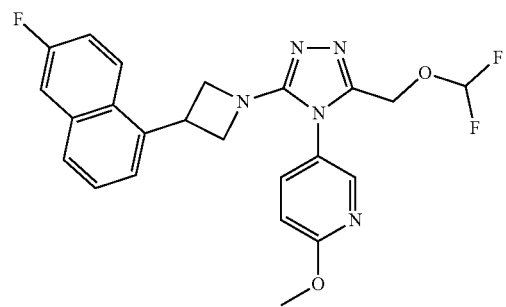

38

The synthetic route of Example 2 was applied except that the starting material 2-methoxyacetylhydrazine in Step 6 was replaced with compound 34b, to obtain the title product 38 (15 mg, pale yellow solid).

MS m/z (ESI): 456.4 [M+1].

$^1$H NMR (400 MHz, CDCl$_3$) δ 8.21 (d, 1H), 7.70 (d, 1H), 7.61-7.59 (m, 1H), 7.58 (d, 1H), 7.49-7.46 (m, 2H), 7.36 (d, 1H), 7.27 (d, 1H), 6.91 (d, 1H), 6.19 (t, 1H), 4.78 (s, 2H), 4.57-4.54 (m, 1H), 4.29 (t, 2H), 4.17 (t, 2H), 4.01 (s, 3H).

Example 39

6-Fluoro-1-(1-(4-(6-methoxypyridin-3-yl)-5-(trifluoromethyl)-4H-1,2,4-triazol-3-yl) azetidin-3-yl)-1,2,3,4-tetrahydroquinoline 39

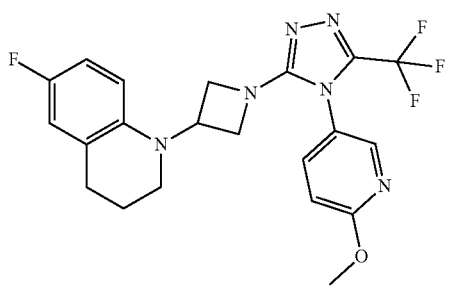

The synthetic route of Example 26 was applied except that the starting material 2-ethoxyacetylhydrazine in Step 5 was replaced with 2,2,2-trifluoroacetylhydrazine (Shanghai Bide Pharmatech Ltd.), to obtain the title product 39 (20 mg, white solid).

MS m/z (ESI): 449.5 [M+1].

$^1$H NMR (400 MHz, CD$_3$OD) δ 8.35 (d, 1H), 7.87 (dd, 1H), 7.01 (d, 1H), 6.78-6.68 (m, 2H), 6.29 (dd, 1H), 4.45-4.37 (m, 1H), 4.08-3.98 (m, 7H), 3.08 (t, 2H), 2.71 (t, 2H), 1.98-1.89 (m, 2H).

Example 40

N-((5-(3-(6-Fluoro-3,4-dihydroquinolin-1(2H)-yl)azetidin-1-yl)-4-(6-methoxypyridin-3-yl)-4H-1,2,4-triazol-3-yl)methyl)methanesulfonamide 40

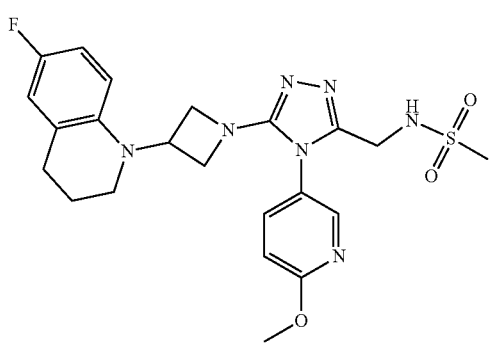

The synthetic route of Example 36 was applied except that the starting material methyl chloroformate in Step 3 was replaced with methylsulfonyl chloride, to obtain the title product 40 (10 mg, white solid).

MS m/z (ESI): 488.3[M+1].

$^1$H NMR (400 MHz, CD$_3$OD) δ 8.29 (d, 1H), 7.81-7.79 (m, 1H), 6.99 (d, 1H), 6.75-6.69 (m, 2H), 6.29-6.26 (m, 1H), 4.36-4.34 (m, 1H), 4.20 (s, 2H), 4.01-3.90 (m, 7H), 3.07 (t, 2H), 2.88 (s, 3H), 2.72-2.67 (m, 2H), 2.03-1.91 (m, 2H).

Example 41

(5-(3-(6-Fluoronaphthalen-1-yl)azetidin-1-yl)-4-(6-methoxypyridin-3-yl)-4H-1,2,4-triazol-3-yl)methanol 2

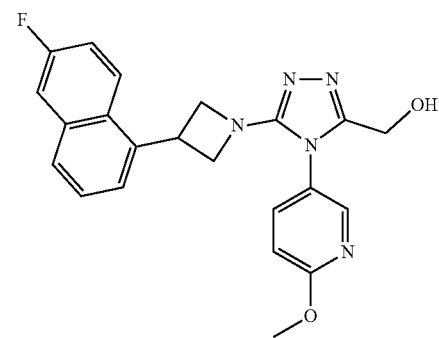

The synthetic route of Example 2 was applied except that the starting material 2-methoxyacetylhydrazine in Step 6 was replaced with 2-hydroxylacetylhydrazine (Shanghai Bide Pharmatech Ltd.), to obtain the title product 41 (20 mg, white solid).

MS m/z (ESI): 406.1 [M+1].

$^1$H NMR (400 MHz, CD$_3$OD) δ 8.23 (d, 1H), 7.86-7.83 (m, 2H), 7.76 (d, 1H), 7.57-7.51 (m, 2H), 7.43-7.41 (m, 1H), 7.33-7.32 (m, 1H), 7.00 (d, 2H), 4.67-4.63 (m, 1H), 4.46 (s, 2H), 4.32 (t, 2H), 4.09 (s, 2H), 4.00 (s, 3H).

Example 42

6-Fluoro-1-(1-(5-(methoxymethyl)-4-(6-methoxypyridin-3-yl)-4H-1,2,4-triazol-3-yl) azetidin-3-yl)-4,4-dimethyl-1,2,3,4-tetrahydroquinoline 42

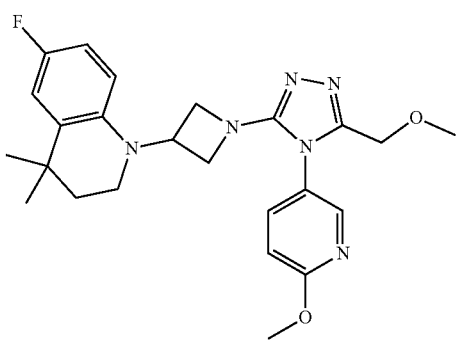

The synthetic route of Example 19 was applied except that the starting material 19a in Step 1 was replaced with 6-fluoro-4,4-dimethyl-1,2,3,4-tetrahydroquinoline (prepared according to the known method disclosed in "*Bioorganic and Medicinal Chemistry Letters,* 2008, 18(5), 1617-1622"), to obtain the title product 42 (20 mg, brown solid).

MS m/z (ESI): 453.2 [M+1].

$^1$H NMR (400 MHz, CD$_3$OD) δ 8.29 (d, 1H), 7.82-7.79 (m, 1H), 7.00-6.93 (m, 2H), 6.77-6.70 (m, 1H), 6.27-6.23

(m, 1H), 4.40-4.38 (m, 3H), 3.99-3.88 (m, 7H), 3.25 (s, 3H), 3.13 (t, 2H), 1.76 (t, 2H), 1.29 (s, 6H).

Example 43

7-Fluoro-4-(1-(4-(6-methoxypyridin-3-yl)-5-(trifluoromethyl)-4H-1,2,4-triazol-3-yl) azetidin-3-yl)-3,4-dihydro-2H-benzo[b][1,4]oxazine 43

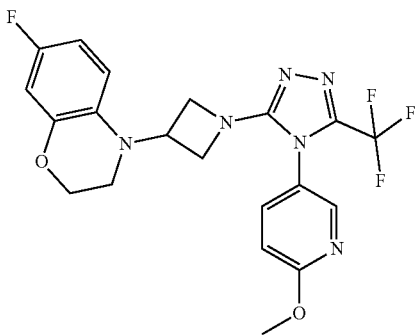

The synthetic route of Example 24 was applied except that the starting material 2-methoxyacetylhydrazine in Step 6 was replaced with 2,2,2-trifluoroacetylhydrazine, to obtain the title product 43 (20 mg, pale yellow solid).

MS m/z (ESI): 451.2 [M+1].

$^1$H NMR (400 MHz, CDCl$_3$) δ 8.19 (d, 1H), 7.56 (d, 1H), 6.92 (d, 1H), 6.56 (d, 1H), 6.48 (t, 1H), 6.19-6.17 (m, 1H), 4.32-4.30 (m, 3H), 4.03-4.01 (m, 7H), 3.13 (t, 2H).

Example 25 in WO2006077496 (Positive Control)

5-(3-(3-(2-Chloro-4-fluorophenoxy)azetidin-1-yl)-5-(methoxymethyl)-4H-1,2,4-triazol-4-yl)-2-methoxypyridine

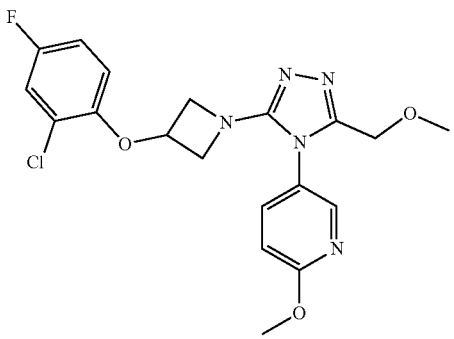 [SMILES: COCc1nnc(N2CC(Oc3ccc(F)cc3Cl)C2)n1-c1ccc(OC)nc1]

The title product was prepared according to the method disclosed in the patent application "WO2006077496".

MS m/z (ESI): 420.3 [M+1].

$^1$H NMR (400 MHz, CDCl$_3$) δ 8.19-8.25 (m, 1H), 7.62 (dd, 1H), 7.13 (dd, 1H), 6.83-6.92 (m, 2H), 6.51 (dd, 1H), 4.87-4.94 (m, 1H), 4.32 (s, 2H), 4.13-4.20 (m, 2H), 3.98-4.06 (m, 5H), 3.30 (s, 3H).

TEST EXAMPLES

Biological Assay

Test Example 1. Determination of the Inhibition Activity of the Compounds of the Present Invention on Human OTR The inhibition effect of the compounds of the present invention on the activity of human OTR protein expressed in HEK293/human OTR stably transfected cells was determined by the following experimental method:

I. Experimental Materials and Instruments
1. Fluo-4 NW calcium assay kit (F36206, invitrogen)
2. MEM (Hyclone, SH30024.01B)
3. G418 sulfate (Enzo, ALX-380-013-G005)
4. Fetal bovine serum (GIBCO, 10099)
5. Sodium pyruvate solution (sigma, 58636-100ML)
6. MEM non-essential amino acid solution (100×) (sigma, M7145-100ML)
7. Flexstation 3 multi-function microplate reader (Molecular Devices)
8. Poly-D-lysine 96-well plate, black/clear (356692, BD)
9. Oxytocin (synthesized by GL Biochem Ltd.)
10. pcDNA3.1 (invitrogen, V79020)
11. pcDNA3.1-hOTR (NM-000706) (synthesized and constructed into pcDNA3.1 plasmid by GENEWIZ Biological Technology Co., Ltd)
12. HEK293 cells (Cat. No. GNHu18, Cell bank of Chinese Academy of Sciences)

II. Experimental Procedures

The pcDNA3.1-hOTR plasmid was transferred into HEK293 cells with the Lipofectamine® 3000 transfection reagent; G418 was added on the next day to screen, and monoclonal cell lines were selected.

HEK293/human OTR stably transfected cells were inoculated in a 96-well plate with an inoculation density of 25,000 cells/well one day in advance. On the next day, a loading buffer containing Fluo-4 dye was formulated using the reagents in the Fluo-4 NW calcium assay kit, and the culture medium was then removed; 100 µl of the loading buffer containing Fluo-4 dye were added to each well, and the plate was incubated at 37° C. for 30 minutes. After that, the plate was moved to room temperature and equilibrated for 10 minutes. The compounds were formulated at $10^6$, $10^5$, $10^4$, $10^3$, $10^2$ and $10^1$ nM. 1 µl of the compounds in each concentration was added to each well, and the plate was incubated at room temperature for 10 minutes. 50 µl of oxytocin polypeptide (3 nM) were automatically added by the machine, and the values were immediately detected at 494/516 nM by the flexstation 3 microplate reader. IC$_{50}$ values of the compounds were calculated by Graphpad prism software using fluorescence signals corresponding to different concentrations.

The inhibition activity of the compounds of the present invention on human OTR was determined by the above test, and the obtained IC$_{50}$ values are shown in Table 1.

TABLE 1

IC$_{50}$ of inhibition activity of the compounds of the present invention on human OTR

| Example No. | IC$_{50}$(nM) |
|---|---|
| 2 | 2 |
| 5 | 188 |

TABLE 1-continued

IC$_{50}$ of inhibition activity of the compounds of the present invention on human OTR

| Example No. | IC$_{50}$(nM) |
|---|---|
| 9 | 40 |
| 10 | 91 |
| 11 | 221 |
| 14 | 130 |
| 17 | 64 |
| 19 | 41 |
| 20 | 104 |
| 21 | 25 |
| 22 | 177 |
| 24 | 100 |
| 25 | 23 |
| 26 | 7 |
| 27 | 8 |
| 28 | 231 |
| 29 | 64 |
| 30 | 4 |
| 31 | 79 |
| 34 | 8 |
| 35 | 181 |
| 36 | 124 |
| 37 | 4 |
| 38 | 2 |
| 39 | 6 |
| 41 | 150 |
| 42 | 23 |
| 43 | 15 |

Conclusion: The compounds of the present invention have a significant inhibition effect on the human OTR activity.

Test Example 2. Determination of the Inhibition Activity of the Compounds of the Present Invention on Human V1aR The inhibition effect of the compounds of the present invention on the activity of human V1 aR protein expressed in HEK293/human V1aR stably transfected cells was determined by the following experimental method:

I. Experimental Materials and Instruments
1. Fluo-4 NW calcium assay kit (F36206, invitrogen)
2. MEM (Hyclone, SH30024.01B)
3. G418 sulfate (Enzo, ALX-380-013-G005)
4. Fetal bovine serum (GIBCO, 10099)
5. Sodium pyruvate solution (sigma, 58636-100ML)
6. MEM non-essential amino acid solution (100×) (sigma, M7145-100ML)
7. Flexstation 3 multi-function microplate reader (Molecular Devices)
8. Poly-D-lysine 96-well plate, black/clear (356692, BD)
9. Vasopressin (Tocris, 2935)
10. pcDNA3.1 (invitrogen, V79020)
11. pcDNA3.1-V1aR (NM-000706) (synthesized and constructed into pcDNA3.1 plasmid by GENEWIZ Biological Technology Co., Ltd)
12. HEK293 cells (Cat. No. GNHu18, Cell Bank of Chinese Academy of Sciences)

II. Experimental Procedures

The pcDNA3.1-V1aR plasmid was transferred into HEK293 cells with the Lipofectamine® 3000 transfection reagent; G418 was added on the next day to screen, and monoclonal cell lines were selected.

HEK293/human V1aR stably transfected cells were inoculated in a 96-well plate with an inoculation density of 25,000 cells/well one day in advance. On the next day, a loading buffer containing Fluo-4 dye was formulated using the reagents in the Fluo-4 NW calcium assay kit, and the culture medium was then removed; 100 μl of the loading buffer containing Fluo-4 dye were added to each well, and the plate was incubated at 37° C. for 30 minutes. After that, the plate was moved to room temperature and equilibrated for 10 minutes. The compounds were formulated at $10^6$, $10^5$, $10^4$, $10^3$, $10^2$ and $10^1$ nM. 1 μl of the compounds in each concentration was added to each well, and the plate was incubated at room temperature for 10 minutes. 50 μl of vasopressin polypeptide (3 nM) were automatically added by the machine, and the values were immediately detected at 494/516 nM by the flexstation 3 microplate reader. IC$_{50}$ values of the compounds were calculated by Graphpad prism software using fluorescence signals corresponding to different concentrations.

The inhibition activity of the compounds of the present invention on human V1aR was determined by the above test, and the obtained IC$_{50}$ values are shown in Table 2.

TABLE 2

IC$_{50}$ of inhibition activity of the compounds of the present invention on human V1aR

| Example No. | IC$_{50}$(μM) |
|---|---|
| 1 | 18.1 |
| 2 | 4.5 |
| 3 | 7.0 |
| 4 | 2.3 |
| 6 | 4.7 |
| 7 | 6.7 |
| 9 | 1.2 |
| 10 | 5.7 |
| 11 | 2.3 |
| 13 | 11.9 |
| 14 | 10.9 |
| 17 | 4.4 |
| 18 | 59.5 |
| 19 | 2.0 |
| 20 | 3.1 |
| 21 | 2.7 |
| 22 | 7.5 |
| 24 | 10.7 |
| 28 | 2.4 |
| 29 | 6.2 |
| 30 | 8.5 |
| 31 | 3.5 |
| 32 | 23.0 |
| 35 | 14.1 |
| 36 | 2.1 |
| 37 | 1.7 |
| 39 | 2 |
| 41 | 9.0 |
| 42 | 4.5 |
| 43 | 7.9 |

Conclusion: The compounds of the present invention have a weak inhibition effect on the human V1 aR activity, indicating that the compounds of the present invention have a selective inhibition effect on the OTR activity.

Test Example 3. Determination of the Inhibition Activity of the Compounds of the Present Invention on Human V1bR The inhibition effect of the compounds of the present invention on the activity of human V1bR protein expressed in HEK293/human V1bR cells was determined by the following experimental method:

I. Experimental Materials and Instruments
1. Fluo-4 NW calcium assay kit (F36206, invitrogen)
2. MEM (Hyclone, SH30024.01B)
3. G418 sulfate (Enzo, ALX-380-013-G005)

4. Fetal bovine serum (GIBCO, 10099)
5. Sodium pyruvate solution (sigma, 58636-100ML)
6. MEM non-essential amino acid solution (100×) (sigma, M7145-100ML)
7. Flexstation 3 multi-function microplate reader (Molecular Devices)
8. Poly-D-lysine 96-well plate, black/clear (356692, BD)
9. Vasopressin (Tocris, 2935)
10. pcDNA3.1 (invitrogen, V79020)
11. pcDNA3.1-V1bR (NM-000706) (synthesized and constructed into pcDNA3.1 plasmid by GENEWIZ Biological Technology Co., Ltd)
12. HEK293 cells (Cat. No. GNHu18, Cell Bank of Chinese Academy of Sciences)

II. Experimental Procedures

The pcDNA3.1-V1bR plasmid was transferred into HEK293 cells with the Lipofectamine® 3000 transfection reagent; G418 was added on the next day, and the HEK293/human V1bR pool cell lines were obtained.

HEK293/human V1bR pool cells were inoculated in a 96-well plate with an inoculation density of 25,000 cells/well one day in advance. On the next day, a loading buffer containing Fluo-4 dye was formulated using the reagents in the Fluo-4 NW calcium assay kit, and the culture medium was then removed; 100 µl of the loading buffer containing Fluo-4 dye were added to each well, and the plate was incubated at 37° C. for 30 minutes. After that, the plate was moved to room temperature and equilibrated for 10 minutes. The compounds were formulated into $10^6$, $10^5$, $10^4$, $10^3$, $10^2$ and $10^1$ nM. 1 µl of the compounds in each concentration was added to each well, and the plate was incubated at room temperature for 10 minutes. 50 µl of vasopressin polypeptide (3 nM) were automatically added by the machine, and the values were immediately detected at 494/516 nM by the flexstation 3 microplate reader. $IC_{50}$ values of the compounds were calculated by Graphpad prism software using fluorescence signals corresponding to different concentrations.

The inhibition activity of the compounds of the present invention on human V1bR was determined by the above test, and the obtained $IC_{50}$ values are shown in Table 3.

TABLE 3

| $IC_{50}$ of inhibition activity of the compounds of the present invention on human V1bR | |
|---|---|
| Example No. | $IC_{50}$(µM) |
| 1 | 448 |
| 2 | 26 |
| 9 | 42.7 |
| 10 | 12.4 |
| 14 | 25.8 |
| 17 | 19.8 |
| 18 | 59.5 |
| 21 | 38.8 |
| 24 | 44.1 |
| 26 | 61.0 |
| 27 | 13.9 |
| 29 | 95.1 |
| 30 | 20.7 |
| 31 | 54.5 |
| 32 | 77.2 |

Conclusion: The compounds of the present invention have no significant inhibition effect on the human V1bR activity, indicating that the compounds of the present invention have a selective inhibition effect on the OTR activity.

Test Example 4. Determination of the Inhibition Activity of the Compounds of the Present Invention on Human V2R The inhibition effect of the compounds of the present invention on the activity of human V2R protein expressed in HEK293/human V2R cells was determined by the following experimental method:

I. Experimental Materials and Instruments
1. cAMP dynamic 2 kit—1,000 tests (62AM4PEB, Cisbio)
2. MEM (Hyclone, SH30024.01B)
3. G418 sulfate (Enzo, ALX-380-013-G005)
4. Fetal bovine serum (GIBCO, 10099)
5. Sodium pyruvate solution (sigma, 58636-100ML)
6. MEM non-essential amino acid solution (100×) (sigma, M7145-100ML)
7. PheraStar multi-function microplate reader (BMG)
8. Corning/Costar 384-well non-adsorbing microplate—black NBS plate (4514, Corning)
9. Cell dissociation solution, enzyme-free, PBS (13151014-100 ml, Thermo Fisher Scientific)
10. HBSS, calcium, magnesium, phenol red free (14025-092, Invitrogen)
11. HEPES, 1M buffer (15630-080, GIBCO)
12. BSA (0219989725, MP Biomedicals)
13. IBMX (I7018-250MG, sigma)
14. Vasopressin (Tocris, 2935)
15. pcDNA3.1 (invitrogen, V79020)
16. pcDNA3.1-V2R (NM-000054) (synthesized and constructed into pcDNA3.1 plasmid by GENEWIZ Biological Technology Co., Ltd)
17. HEK293 cells (Cat. No. GNHu18, Cell Bank of Chinese Academy of Sciences)

II. Experimental Procedures

The pcDNA3.1-V2R plasmid was transferred into HEK293 cells with the Lipofectamine® 3000 transfection reagent; G418 was added on the next day, and the HEK293/human V2R pool cell lines were obtained.

1) Dissociation of the Cells:
HEK293/human V2R pool cells were dissociated with the cell dissociation solution (enzyme-free), thereby dissociating the cells from the cell culture dish into individual cells. Then the cell solution was blown well, and centrifuged to remove the supernatant. The cells were resuspended in the test buffer 1 (1×HBSS+20 mM HEPES+0.1% BSA) and counted. The cell density was adjusted to 1250 cells/5 µl, i.e., $2.5*10^5$/ml.

2) Formulation of the Compounds
The compounds were formulated into a series of concentrations of 20 mM, 6.67 mM, 2.22 mM, 0.74 mM, 0.25 mM, 0.08 mM, 27.4 µM, 9.14 µM, 3.05 µM, 1.02 µM, 0.34 µM and 0 µM (DMSO) with pure DMSO. The compounds were then diluted into a 4-fold working concentration solution with the test buffer 2 (test buffer 1+1 mM IBMX).

Agonist: 460 µM vasopressin was used as the mother liquor, which was formulated at 2 µM with DMSO, and then diluted to 0.5 nM with the test buffer 2.

Standards: The first point was 20 µl of a stock solution (2848 nM), which was diluted successively to a total of eleven concentrations in a 4-fold concentration gradient with the test buffer 1 from the second point.

3) Addition of the Compounds and Incubation:
1. The well-mixed cells were added to a 384-well plate (5 µl/well) without changing the tip.
2. The test compounds and positive compound formulated were added (2.5 µl/well), and the tips were changed.

3. The plate was centrifuged at 1000 rpm for 1 min, shaken for 30 sec to mix well, and incubated at room temperature for 30 min.

4. The standard curve wells were added with the test buffer 2 (5 μl/well).

5. The formulated agonist was added (2.5 μl/well), and the tips were changed; the plate was centrifuged at 1000 rpm for 1 min, shaken for 30 sec to mix well, and incubated at room temperature for 30 min.

6. cAMP-d2 (a component in the cAMP dynamic 2 kit) and Anti-cAMP-Eu-Cryptate (a component in the cAMP dynamic 2 kit) were formulated in the dark, which were then mixed well with cAMP lysate (a component in the cAMP dynamic 2 kit) in a ratio of 1:4. Each well was added with the formulated cAMP-d2 solution (5 μl/well), followed by addition of Anti-cAMP-Eu-Cryptate (5 μl/well). The plate was shaken for 30 sec to mix well, and incubated in the dark at room temperature for 1 h.

4) Plate Reading:

The HTRF Signals were Read by the PheraStar Multi-Function Microplate Reader.

5) Data Processing

The data in this test was processed using the data processing software Graphpad Prism.

The inhibition activity of the compounds of the present invention on human V2R was determined by the above test, and the $IC_{50}$ values obtained are shown in Table 4.

TABLE 4

| $IC_{50}$ of inhibition activity of the compounds of the present invention on human V2R | |
|---|---|
| Example No. | $IC_{50}$ (μM) |
| 1 | >100 |
| 2 | 4.9 |
| 9 | 12.5 |
| 10 | 20.7 |
| 11 | 25.7 |
| 14 | 11.8 |
| 17 | 10.9 |
| 18 | 59.4 |
| 21 | 17.3 |
| 23 | 52.0 |
| 24 | 67.2 |
| 26 | 1.4 |
| 27 | 9.1 |
| 29 | 12.1 |
| 30 | 6.7 |
| 31 | 5.8 |
| 32 | >100 |

Conclusion: The compounds of the present invention have no significant inhibition effect on the human V2R activity, indicating that the compounds of the present invention have a selective inhibition effect on the OTR activity.

Test Example 5. Determination of the Activity of the Compounds of the Present Invention on the Brain Permeability of Rats The activity of the compounds of the present invention on the brain permeability of rats was determined by the following experimental method:

I. Experimental Materials and Instruments

1. RED Device Inserts (Thermo Scientific, QL21291110)
2. API 4000 Q-trap linear ion trap mass spectrometer (Applied Biosystems)
3. LC-30A ultra high pressure liquid chromatography system (Shimadzu)
4. pH 7.4 PBS (100 mM, stored in 4° C. refrigerator)
5. SD rats, provided by Jiesijie Laboratory Animal Co., LTD, with Certificate No.: SCXK (Shanghai) 2013-0006.

2. Treatment of the Test Animals

Four SD rats (half male and half female) were maintained in a 12 hours light/12 hours dark cycle, in a constant temperature of 24±3° C. and a humidity of 50-60%, and free access to food and water. The compounds were administered intragastrically to the rats after fasting overnight. The administration dosage was 10 mg/kg. The administration group was sacrificed after blood collection at 0.5 h to 2 h after administration (blood volume: 0.5 ml). The blood sample was stored in heparinized tubes, and centrifuged for 10 minutes at 3500 rpm to separate the plasma, which was marked as plasma 1 and stored at 20° C. The animal was decapitated after sacrificing, and the brain tissue was collected. The residual blood in the brain tissue was sucked with a filter paper, which was marked as brain tissue 1, and stored at 0° C. ten minutes later. Another three animals were treated by the same method as that of administration group to obtain blank plasma and brain tissue 2.

3. Plasma Protein Binding Equilibrium Dialysis Process 3.1 Preparation of the Samples The drug compounds were diluted to 50 mM with DMSO to obtain a stock solution I. An appropriate amount of stock solution I was diluted with methanol to obtain a diluted stock solution II (200 μM). 10 μl of stock solution II was moved to a 1.5 ml Eppendorf tube, and then added with 990 μl of blank plasma, and mixed well to obtain 2 μM of plasma sample 2 (concentration of DMSO≤0.2%), which was used for the determination of plasma protein binding rate at this concentration. 50 μl of the above plasma sample formulated was marked as $T_0$, and stored at −80° C. in a refrigerator for testing.

3.2 Experimental Procedures

The equilibrium dialysis tube of RED Device Inserts was inserted into a 96-well plate. 300 μl of the above plasma sample 2 containing test compound and corresponding blank plasma sample were added to wells with red mark (plasma chamber). 500 μl of phosphate buffer solution (pH 7.4) was added to another well side-by-side with red mark too (buffer chamber). According to the above procedures, each concentration of each compound had 2-3 samples. Then, the 96-well plate was covered by a sealing tape, and the entire plate was placed in a heat mixer and equilibrated at 37° C. at 400 rpm for 4 h. The 96-well plate device was removed from the heat mixer after incubation to achieve equilibrium dialysis. 50 μl of equilibrated plasma sample or dialysate sample were added with 50 μl of corresponding unequilibrated blank phosphate buffer solution free of compounds or blank plasma free of compounds, and then added with 300 μl of internal standard (formulated with acetonitrile), vortex-mixed for 5 min, and centrifuged for 10 minutes (4000 rpm). The supernatant was collected for LC/MS/MS analysis. To sample was not subjected to incubation. The chromatographic peak area ratios of the total drug (plasma chamber) and the free drug (buffer chamber) to the internal standard were determined directly by the LC/MS/MS method established above respectively, and the free percent ($f_{u\ plasma}$ %) was calculated.

4. Brain Tissue Protein Binding Equilibrium Dialysis Process

Brain tissue protein binding equilibrium dialysis process: the blank brain tissue 2 was formulated into a blank brain homogenate with PBS (pH 7.4) according to a dilution factor of 11, and added with compound to formulate a 2 μM brain homogenate. Other procedures were the same with that of plasma protein binding, the chromatographic peak area ratios of the total drug (brain homo chamber) and the free drug (buffer chamber) to the internal standard were determined by the established LC/MS/MS method respectively, and the free percent ($f_{u\ brain\ hom}$ %) was calculated.

5. Brain Permeability Test Method

1) The drug concentrations in plasma 1 and brain tissue 1 of rats 0.5 h after administration were determined by the established LC/MS/MS method respectively, which were the total concentration ($C_{total,\ p}$ and $C_{total,\ b}$);

2) The protein binding rates of the compound in the plasma and brain tissue of rat were determined respectively by equilibrium dialysis method with the RED Device Inserts device, so as to calculate the free percent ($f_{u\ plasma}$ %, $f_{u\ brain}$ %);

Free percent of plasma ($f_{u\ plasma}$ %)=$C_{buffer}/C_{plasma}$×100%;

Free percent of brain homogenate ($f_{u\ brain\ hom}$ %)=$C_{buffer}/C_{brain\ hom}$×100%;

Free percent of brain tissue ($f_{u\ brain}$ %)=$f_{u\ brain\ hom}$/(Df−(Df−1)*$f_{u\ brain\ hom}$)×100%, wherein Df=11.

3) The blood-brain permeability index Kp-unbound was calculated using the following formula.

$$Kp,\ \text{unbound} = \frac{C_{u,b}}{C_{u,p}} = \frac{C_{total,b} \times f_{u,b}}{C_{total,p} \times f_{u,p}} = Kp \times \left(\frac{f_{u,b}}{f_{u,p}}\right)$$

6. Test Results and Discussion

The brain permeability indexes of the compounds of the present invention are shown below:

| No. | Kp-unbound |
|---|---|
| Example 2 | 0.199 |
| Example 17 | 0.295 |
| Example 38 | 0.175 |
| Positive control Example 25 in WO2006077496 | 0.064 |

Conclusion: The compounds of the present invention have good brain permeability, which is more than three times that of the positive control compound.

Pharmacokinetics Evaluation

Test Example 6. Pharmacokinetics Assay of the Compounds of the Present Invention 1. Abstract Male SD rats were used as test animals. The drug concentration in plasma at different time points was determined by LC/MS/MS method after intragastrical administration of the compounds of Examples 2, 17, 34, 37, 38, 39 and 43 to rats. The pharmacokinetic behavior of the compounds of the present invention was studied and evaluated in rats.

2. Test Protocol 2.1 Test Compounds

Compounds of Examples 2, 17, 34, 37, 38, 39 and 43.

2.2 Test Animals

Twenty-one healthy adult male Sprague-Dawley (SD) rats were purchased from Shanghai Jiesijie Laboratory Animal Co., LTD, with Certificate No.: SCXK (Shanghai) 2013-0006, and equally divided into 7 groups (3 rats per group).

2.3 Preparation of the Test Compounds

A certain amount of the test compound was weighed, and added with 2.5% by volume of DMSO and 97.5% by volume of 10% solutol HS-15 to formulate a 0.2 mg/mL colorless, clear and transparent solution.

2.4 Administration

After an overnight fast, SD rats were administered intragastrically the test compounds at an administration dosage of 30.0 mg/kg and an administration volume of 10.0 mL/kg.

3. Process

The rats were intragastrically administered the compounds of Examples 2, 17, 34, 37, 38, 39 and 43. 0.2 mL of blood was taken from the orbital sinus before administration and at 0.5, 1.0, 2.0, 4.0, 6.0, 8.0, 11.0 and 24.0 hours after administration. The samples were stored in heparinized tubes, and centrifuged for 10 minutes at 4° C. at 3500 rpm to separate the plasma. The plasma samples were stored at −20° C. The rats were fed 2 hours after administration.

The content of the test compounds in the plasma of rats after intragastrical administration of the test compounds at different concentrations was determined: 50 µL of rat plasma at each time after administration was taken, added with 50 µL of the internal standard solution of camptothecin (100 ng/mL) and 150 µL of acetonitrile, vortex-mixed for 5 minutes, and centrifuged for 10 minutes (4000 rpm). 3 µL of the supernatant was taken from the plasma samples for LC/MS/MS analysis.

4. Results of Pharmacokinetic Parameters

Pharmacokinetic parameters of the compounds of the present invention are shown below:

| | Pharmacokinetics assay (30 mg/kg, male rats) | | | | | |
|---|---|---|---|---|---|---|
| No. | Plasma concentration Cmax (ng/mL) | Area under curve AUC (ng/mL*h) | Half-life T1/2 (h) | Residence time MRT (h) | Clearance CLz/F (ml/min/kg) | Apparent distribution volume Vz/F (ml/kg) |
| Example 2 | 3930 ± 3026 | 8580 ± 3564 | 0.91 ± 0.25 | 2.46 ± 1.44 | 63.8 ± 26.5 | 5294 ± 3442 |
| Example 17 | 2020 ± 580 | 11188 ± 4391 | 3.35 ± 0.399 | 5.08 ± 0.552 | 48 ± 19 | 13694 ± 3831 |
| Example 34 | 1073 ± 252 | 5328 ± 981 | 2.16 ± 0.345 | 3.84 ± 1.08 | 95.8 ± 16.0 | 17805 ± 3334 |
| Example 37 | 1115 ± 950 | 8185 ± 9853 | 2.95 ± 0.42 | 4.90 ± 1.36 | 201 ± 223 | 56326 ± 65981 |
| Example 38 | 1055 ± 270 | 5626 ± 3011 | 2.83 ± 1.90 | 4.19 ± 1.25 | 104 ± 44 | 27799 ± 22764 |
| Example 39 | 1202 ± 68.5 | 3832 ± 83.7 | 3.09 ± 0.199 | 3.61 ± 0.022 | 131 ± 2.85 | 34980 ± 3010 |
| Example 43 | 1579 ± 601 | 5564 ± 2329 | 3.31 ± 0.23 | 106 ± 59 | 3.81 ± 0.12 | 31129 ± 19284 |

Conclusion: The compounds of the present invention are well absorbed, and have a pharmacokinetic advantage.

Pharmacodynamic Assay

Test Example 7. Experiment of Treating Oxytocin-Induced Rat Uterine Contraction Model of OTR Inhibitors 1. Experimental Purpose The efficacy of OTR inhibitors (compound 2-10mpk, compound 2-30mpk and compound 2-100mpk) on oxytocin (OT)-induced rat uterine contraction model was evaluated by establishing a rat uterine contraction model.

2. Experimental Compounds

Oxytocin (OT, GL Biochem, customized, item No. 269099), stored at −80° C.;

Polyoxyethylene hydrogenated castor oil (Cremophor RH 40, Shanghai Chineway Pharmaceutical Technology Co., LTD.);

Glyceryl monolinoleate (Masine35-1, GATTEFOSSE SAS);

Ulatan, Shanghai Bide Pharmatech Ltd.;

Compound 2-100mpk: 221.0 mg of compound 2 was weighed, added with 5.40 ml of Cremophor RH40, 2.16 ml of Masine 35-1, 3.24 ml of polyethylene glycol 400 (PEG400) and 1.20 ml of ethanol respectively, and mixed well by ultrasonic vibration;

Compound 2-30mpk: 54.2 mg of compound 2 was weighed, added with 4.50 ml of Cremophor RH40, 1.80 ml of Masine 35-1, 2.70 ml of polyethylene glycol 400 (PEG400) and 1.00 ml of ethanol respectively, and mixed well by ultrasonic vibration;

Compound 2-10mpk: 1 ml of compound 2-100mpk solution was added with 9 ml of solvent (45% of Cremophor RH40, 18% of Masine 35-1, 27% of PEG400 and 10% of ethanol), and mixed well.

3. Experimental Method and Experimental Materials 3.1. Test Animals and Breeding Conditions Forty laboratory female SD rats were purchased from Shanghai SLAC Laboratory Animal Co., Ltd (Shanghai, China, Certificate No.: SCXK (Shanghai) 2012-0002, Qualification Certificate No.: 20150000541877), and weighed 180-200 g when purchased. The rats (5 rats per cage) were maintained in a 12 hours light/12 hours dark cycle, in a constant temperature of 23±1° C. and a humidity of 50-60%, and free access to food and water. The animals were subjected to the test after purchasing and adaptive feeding.

3.2. Grouping of Animals:

After adaptive feeding, the SD rats were grouped as follows:

| Groups | N | Inducing agent | Administration dosage | Administration volume and route |
|---|---|---|---|---|
| Solvent group | 10 | 1 µg/kg OT | — | 6 ml/kg, p.o. |
| Compound 2-10 mpk | 10 | 1 µg/kg OT | 10 mg/kg | 6 ml/kg, p.o. |
| Compound 2-30 mpk | 10 | 1 µg/kg OT | 30 mg/kg | 6 ml/kg, p.o. |
| Compound 2-100 mpk | 10 | 1 µg/kg OT | 100 mg/kg | 6 ml/kg, p.o. |

Note:
p.o. refers to oral administration.

3.3. Experimental Method

The SD rats were adaptively fed to appropriate body weight and randomly grouped as follows: solvent group, compound 2-10mpk, compound 2-30mpk and compound 2-100mpk. The drug was orally administrated to the animal one hour before modeling. The animal was anaesthetized 20 minutes after administration (by 8 ml/kg of 20% urethane). A PE catheter was inserted into the jugular vein for intravenous administration, which was filled with physiological saline. The abdomen was opened. The left cornua uteri near the ovarian side was ligatured, and wired at a distance of 3 cm from the ovary. An incision was made, and a PE catheter connected with a pressure transducer was inserted, which was injected with 0.1 ml of normal saline through a tee after ligation. The multi-function signal acquisition and processing system was connected. After pressure equilibrium, 1 µg/kg of OT was administrated intravenously one hour after administration of the drug, and the change in uterine pressure within 10-15 minutes was observed.

3.4. Data Statistics

After completion of the experiment, the area under curve (AUC) of the uterine contraction pressure 5 minutes before and after the administration of the inducing agent was calculated respectively. The efficacy of the test compound was evaluated by calculating the ratio of the difference value in AUC before and after induction to the AUC before induction, and comparing with the difference value of the ratio after administration of the test compound.

$\Delta \text{AUC ratio} = (AUC_0 - AUC_T)/AUC_0$;

$AUC_0$: area under curve before induction; $AUC_T$: area under curve after induction.

4. Results

The efficacy of compound 2 on the OT-induced rat uterine contraction model is shown in FIG. 1.

5. Conclusion

Comparing to the solvent control group, 30mpk and 100mpk of compound 2 can effectively block the downstream function (uterine contraction) of oxytocin receptors mediated by oxytocin. The uterine contraction model can quantitatively characterize the OTR antagonistic activity of the compound. Documents have reported that the oxytocin receptors in the male brain are closely related to the ejaculation function of male. Therefore, the compounds of the present invention having a strong oxytocin receptor antagonistic function can be used for the treatment of male sexual dysfunction under the condition of having a good brain permeability.

What is claimed is:

1. A compound of formula (I):

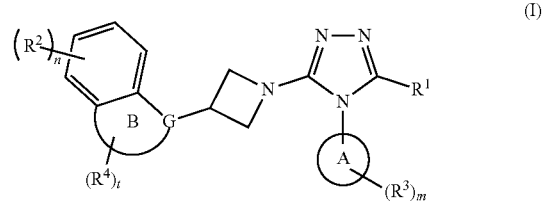

or a tautomer, mesomer, racemate, enantiomer, diastereomer thereof, or a mixture thereof, or a pharmaceutically acceptable salt thereof, wherein:

G is selected from the group consisting of C, CH and N;

ring A is aryl or heteroaryl;

ring B is selected from the group consisting of cycloalkyl, heterocyclyl, aryl and heteroaryl;

$R^1$ is alkyl, wherein the alkyl is optionally substituted by one or more substituents selected from the group consisting of alkoxy, halogen, haloalkyl, haloalkoxy, hydroxy, hydroxyalkyl, cyano, amino, nitro, cycloalkyl, heterocyclyl, heterocycloxy, NHS(O)$_s$R$^5$, NHC(O)OR$^5$, aryl and heteroaryl;

each R$^2$ is identical or different and each is independently selected from the group consisting of hydrogen, halogen, alkyl, alkoxy, haloalkyl, oxo, hydroxy, hydroxyalkyl, cyano, amino, nitro, cycloalkyl, heterocyclyl and —C(O)OR$^5$;

each R$^3$ is identical or different and each is independently selected from the group consisting of hydrogen, halogen, alkyl, alkoxy, haloalkyl, hydroxy, hydroxyalkyl, cyano, amino, nitro, cycloalkyl and heterocyclyl;

each R$^4$ is identical or different and each is independently selected from the group consisting of hydrogen, halogen, alkyl, alkoxy, haloalkyl, oxo, hydroxy, hydroxyalkyl, cyano, amino, nitro, cycloalkyl, heterocyclyl and —C(O)OR$^5$;

R$^5$ is selected from the group consisting of hydrogen, alkyl, haloalkyl, hydroxyalkyl, cycloalkyl, heterocyclyl, aryl and heteroaryl;

s is 0, 1 or 2;
n is 0, 1, 2, 3 or 4;
m is 0, 1, 2, 3 or 4; and
t is 0, 1, 2 or 3.

2. The compound according to claim 1, which is a compound of formula (II):

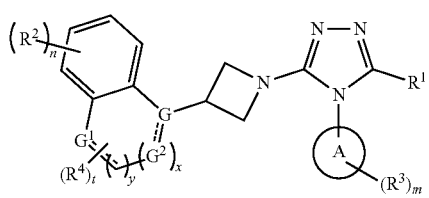

(II)

or a tautomer, mesomer, racemate, enantiomer, diastereomer thereof, or a mixture thereof, or a pharmaceutically acceptable salt thereof,
wherein:
═══ is a single bond or a double bond;
G is selected from the group consisting of C, CH and N;
G$^1$ is selected from the group consisting of N, NH, C, CH, CH$_2$, O and S;
G$^2$ is selected from the group consisting of C, CH, CH$_2$, N and NH;
x is 0 or 1;
y is 0 or 1; and
ring A, R$^1$~R$^4$, n, m and t are as defined in claim 1.

3. The compound according to claim 1, which is a compound of formula (III):

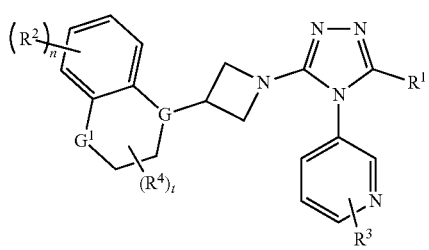

(III)

or a tautomer, mesomer, racemate, enantiomer, diastereomer thereof, or a mixture thereof, or a pharmaceutically acceptable salt thereof,
wherein:
G is selected from the group consisting of C, CH and N;
G$^1$ is selected from the group consisting of N, NH, C, CH, CH$_2$ and O;
R$^1$~R$^4$, n and t are as defined in claim 1.

4. The compound according to claim 1, which is a compound of formula (IV):

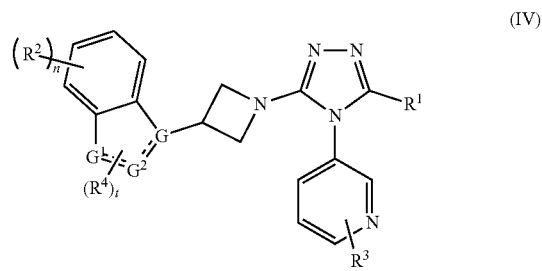

(IV)

or a tautomer, mesomer, racemate, enantiomer, diastereomer thereof, or a mixture thereof, or a pharmaceutically acceptable salt thereof,
wherein:
═══ is a single bond or a double bond;
G is selected from the group consisting of C, CH and N;
G$^1$ is selected from the group consisting of N, NH, C, CH, CH$_2$, O and S;
G$^2$ is selected from the group consisting of C, CH, CH$_2$, N and NH;
R$^1$~R$^4$, n and t are as defined in claim 1.

5. The compound according to claim 1, wherein ring A is pyridyl or benzodioxole.

6. The compound according to claim 1, wherein

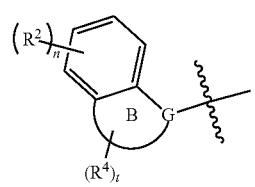

is selected from the group consisting of:

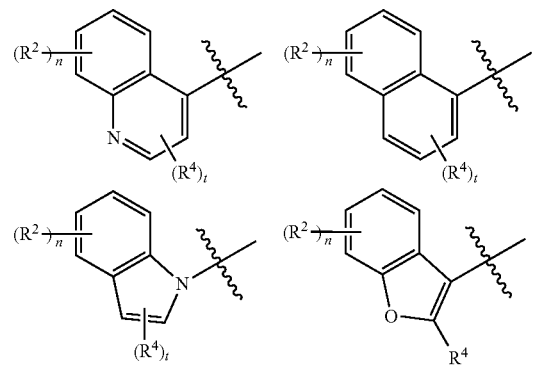

139
-continued

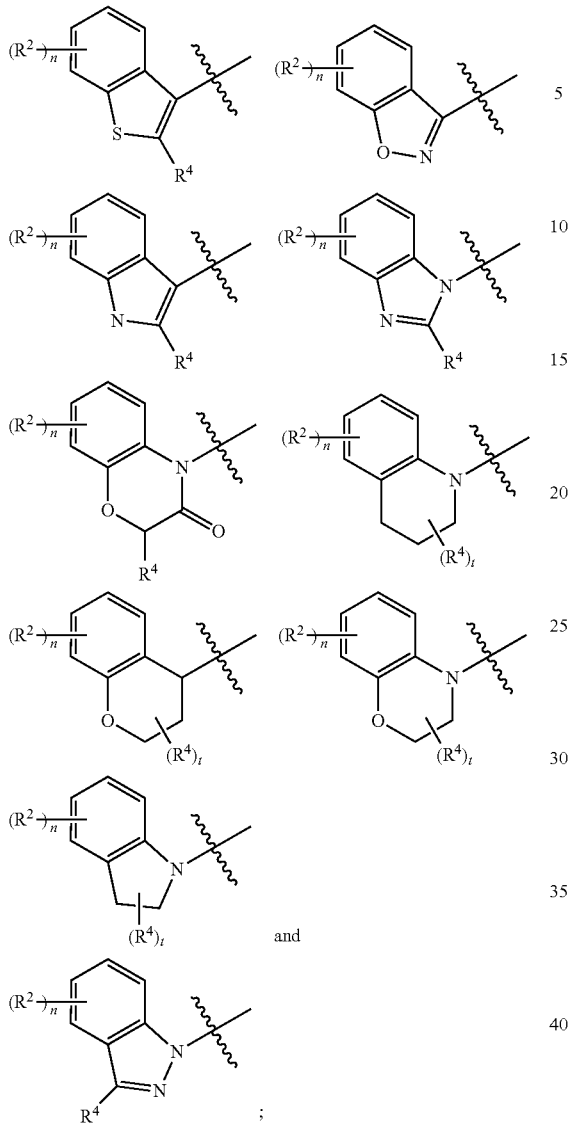

wherein:

R², R⁴, n and t are as defined in claim 1.

7. The compound according to claim 1, wherein $R^1$ is alkyl, wherein the alkyl is optionally substituted by one or more substituents selected from the group consisting of alkoxy, halogen, haloalkyl, haloalkoxy, hydroxy, NHS(O)$_s$R⁵ and NHC(O)OR⁵; R⁵ is alkyl; and s is 0, 1 or 2.

8. The compound according to claim 1, wherein each $R^2$ is identical or different and each is independently selected from the group consisting of hydrogen, halogen, alkyl and haloalkyl.

9. The compound according to claim 1, wherein $R^3$ is alkoxy.

10. The compound according to claim 1, wherein each $R^4$ is identical or different and each is independently selected from the group consisting of hydrogen, halogen, alkyl, haloalkyl, cyano, oxo and —C(O)OR⁵; and R⁵ is alkyl.

11. The compound according to claim 1, wherein n is 1 or 2; and m is 0 or 1.

140

12. A compound selected from the group consisting of:

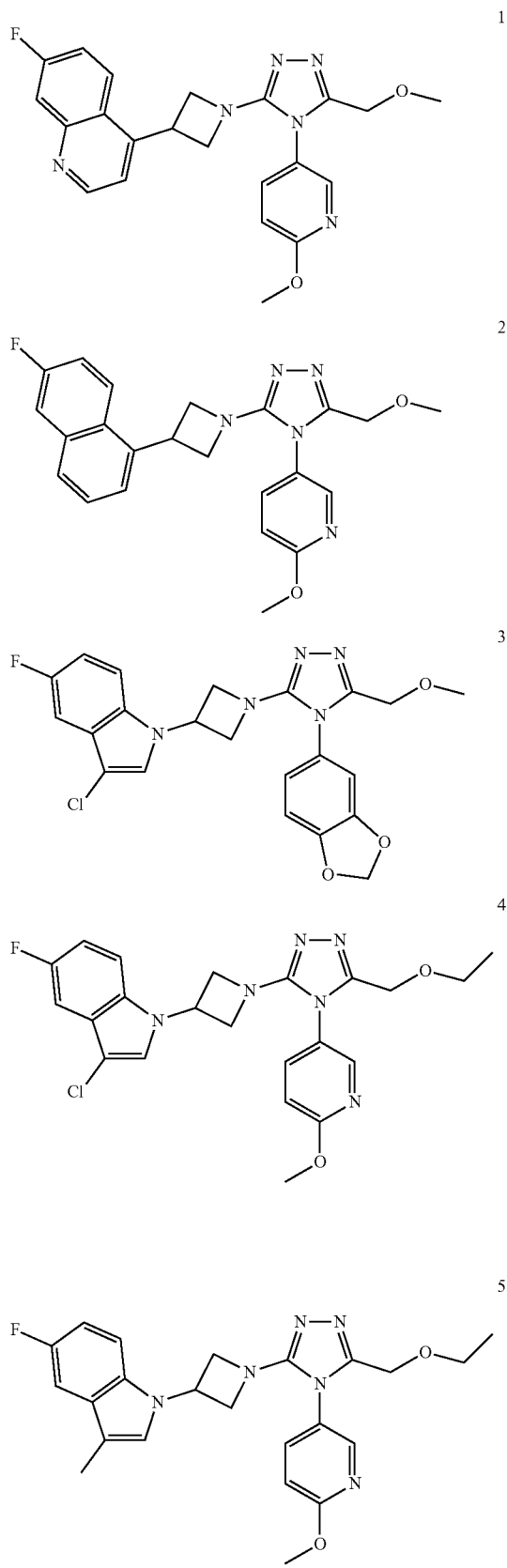

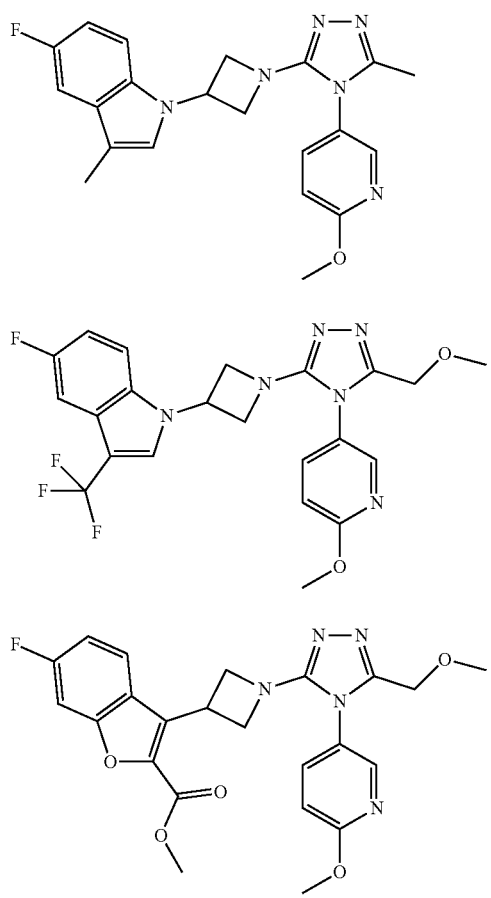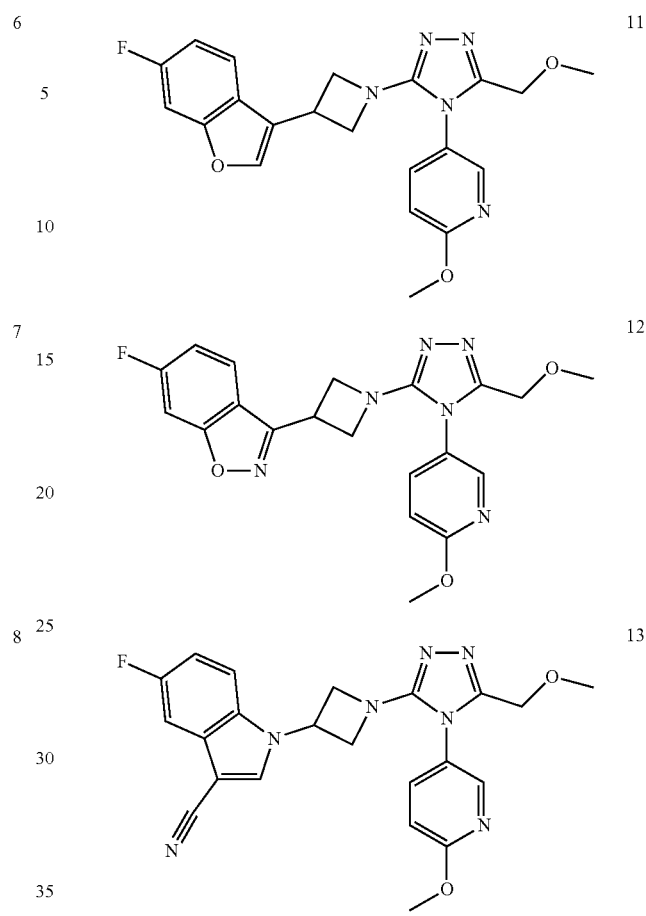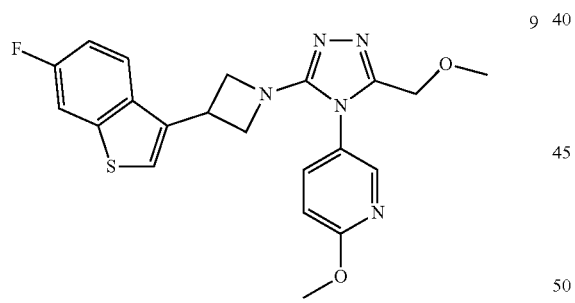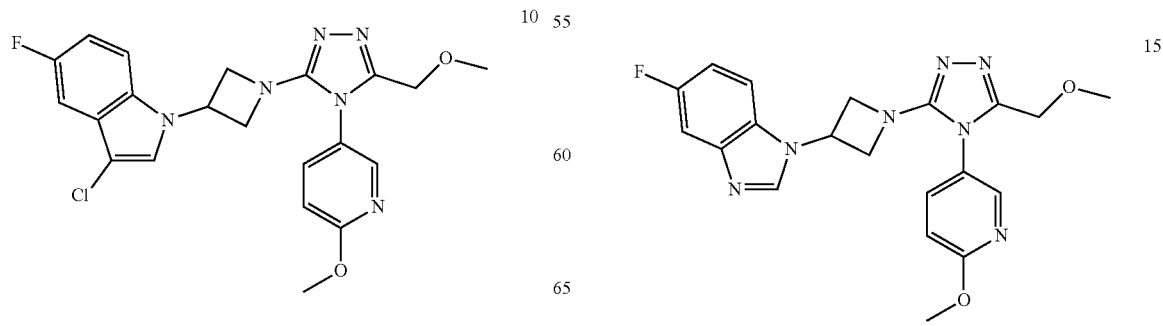

16
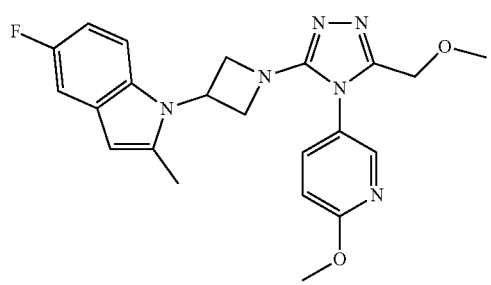
17
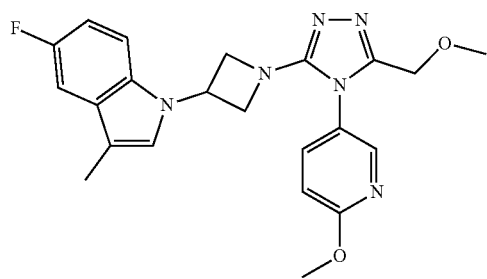
18
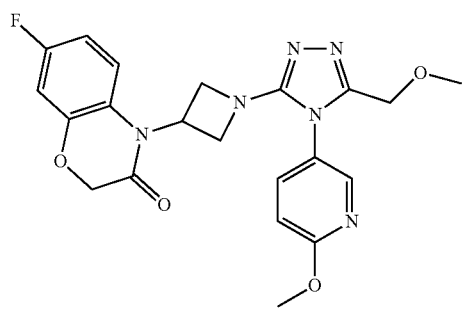
19
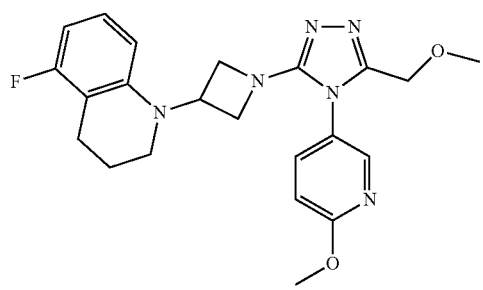
20
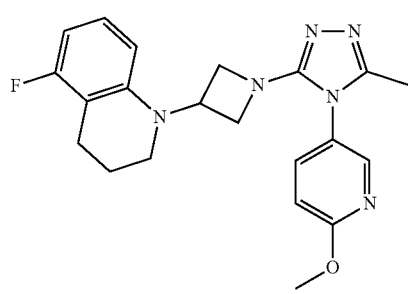
21
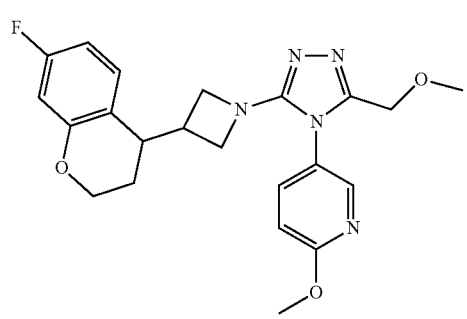
22
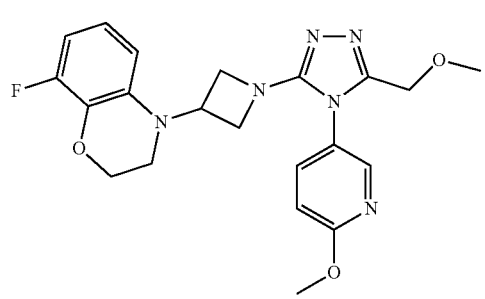
23
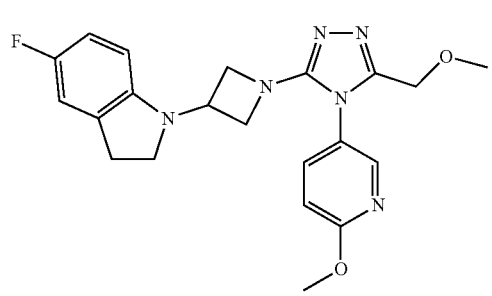
24
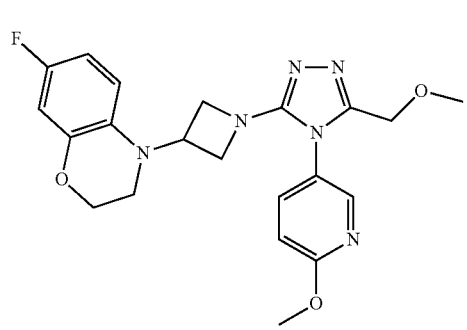
25
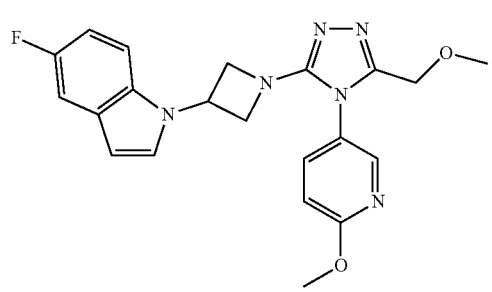

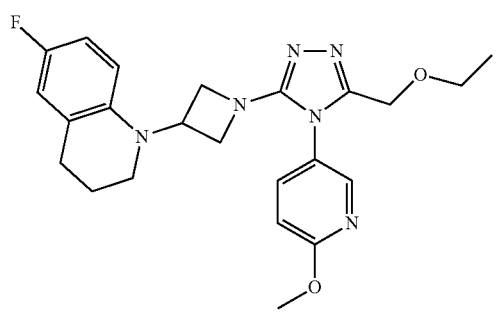
26
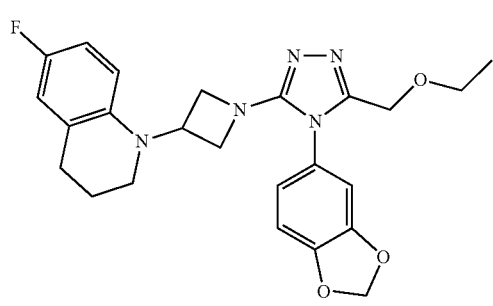
27
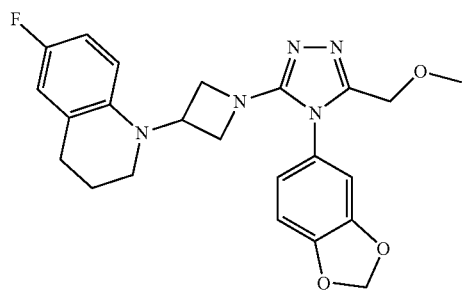
28
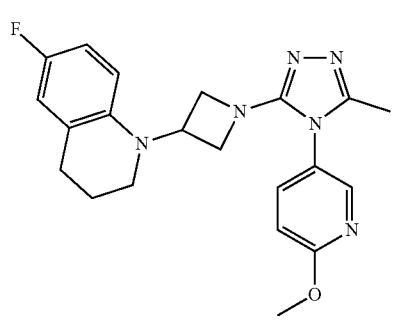
29
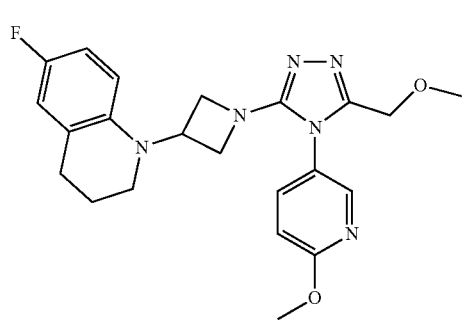
30
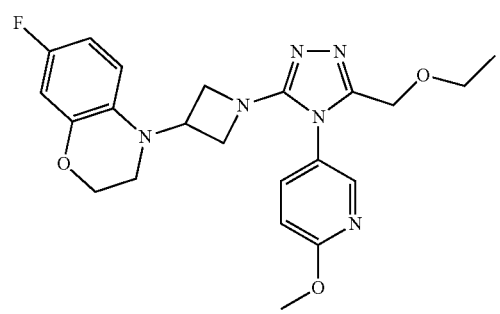
31
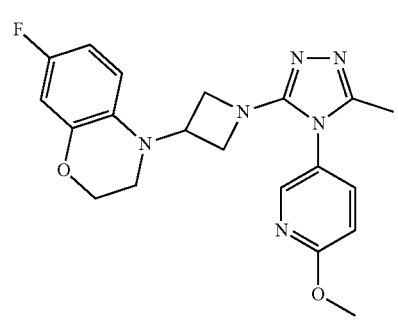
32
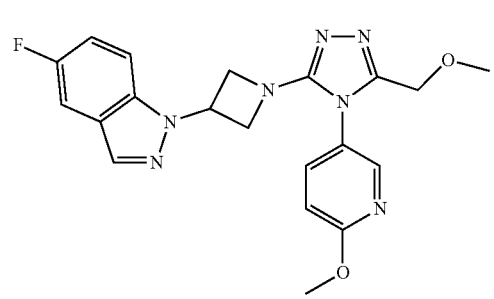
33
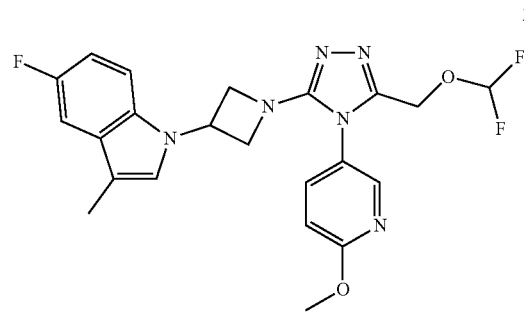
34
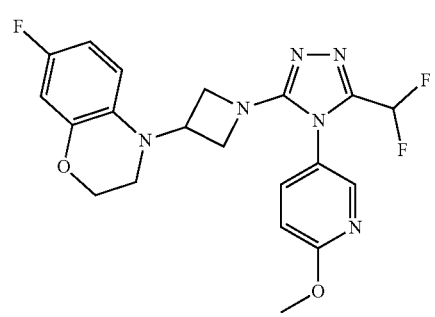
35 or a tautomer, mesomer, racemate, enantiomer, diastereomer thereof, or a mixture thereof, or a pharmaceutically acceptable salt thereof.

13. A compound of formula (I-A):

(I-A)

or a tautomer, mesomer, racemate, enantiomer, diastereomer thereof, or a mixture thereof, or a pharmaceutically acceptable salt thereof,
wherein:
G is selected from the group consisting of C, CH and N;
ring A is aryl or heteroaryl;
ring B is selected from the group consisting of cycloalkyl, heterocyclyl, aryl and heteroaryl;
each $R^2$ is identical or different and each is independently selected from the group consisting of hydrogen, halogen, alkyl, alkoxy, haloalkyl, oxo, hydroxy, hydroxyalkyl, cyano, amino, nitro, cycloalkyl, heterocyclyl and —C(O)OR$^5$;

each R³ is identical or different and each is independently selected from the group consisting of hydrogen, halogen, alkyl, alkoxy, haloalkyl, hydroxy, hydroxyalkyl, cyano, amino, nitro, cycloalkyl and heterocyclyl;

each R⁴ is identical or different and each is independently selected from the group consisting of hydrogen, halogen, alkyl, alkoxy, haloalkyl, oxo, hydroxy, hydroxyalkyl, cyano, amino, nitro, cycloalkyl, heterocyclyl and —C(O)OR⁵;

R⁵ is selected from the group consisting of hydrogen, alkyl, haloalkyl, hydroxyalkyl, cycloalkyl, heterocyclyl, aryl and heteroaryl;

n is 0, 1, 2, 3 or 4;

m is 0, 1, 2, 3 or 4; and t is 0, 1, 2 or 3.

14. The compound according to claim 13, which is selected from the group consisting of:

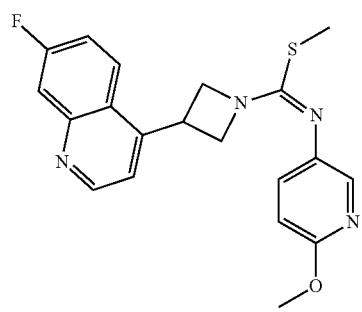

1g

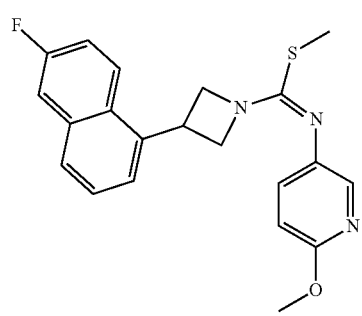

2f

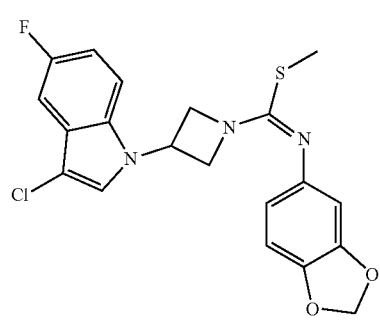

3i

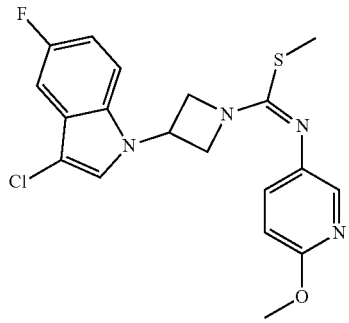

4b

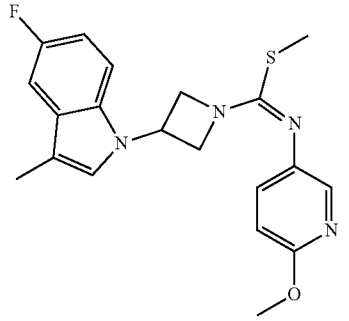

5f

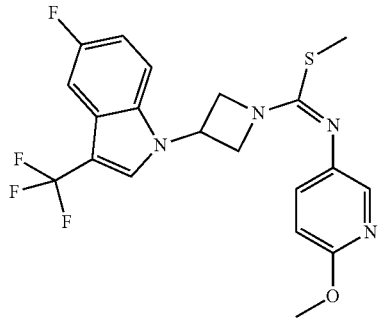

7d

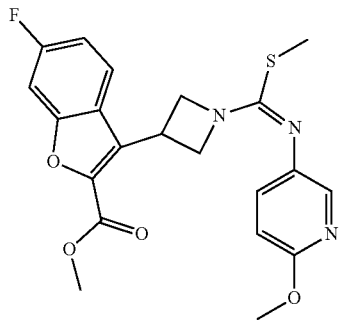

8f

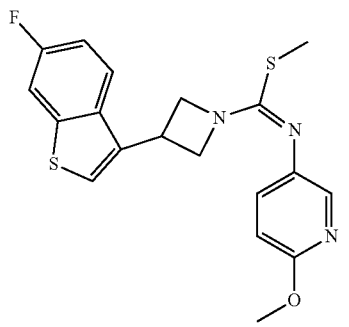

9f

-continued
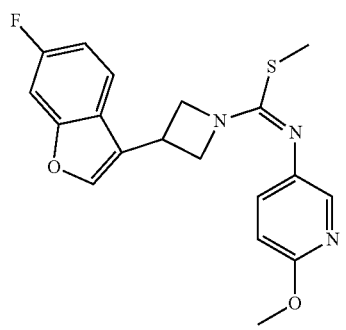
11i
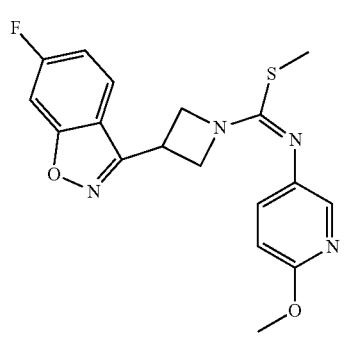
12e
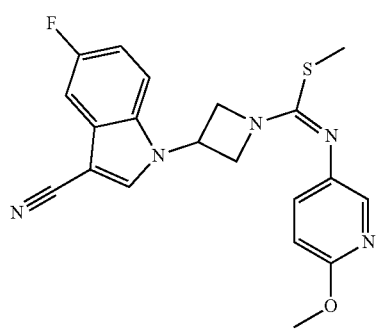
13d
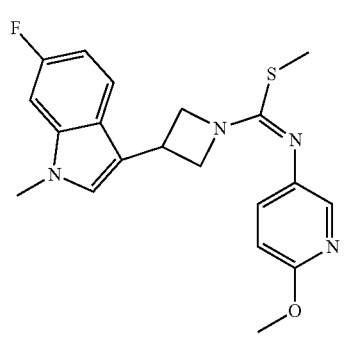
14g
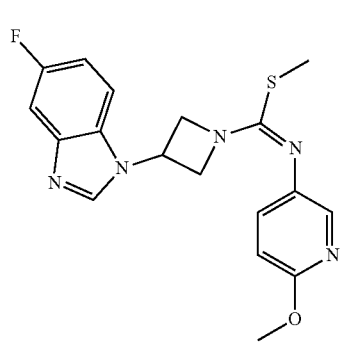
15f
-continued
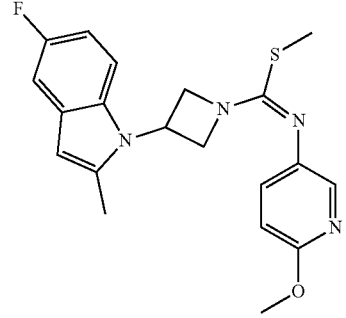
16f
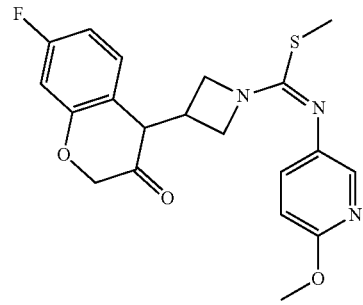
18g
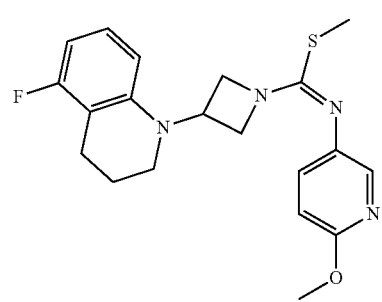
19e
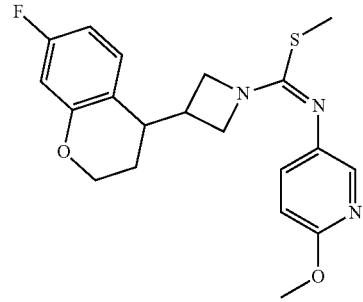
21g
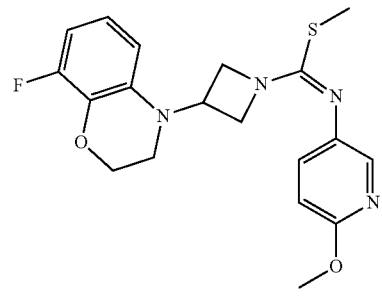
22f

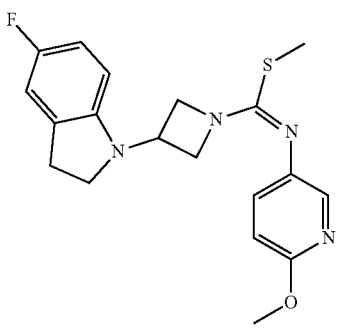

23c

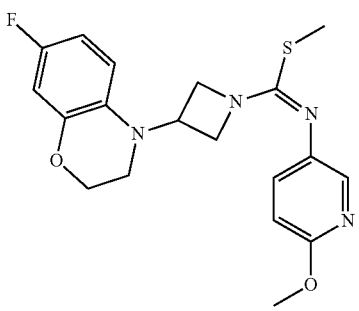

24f

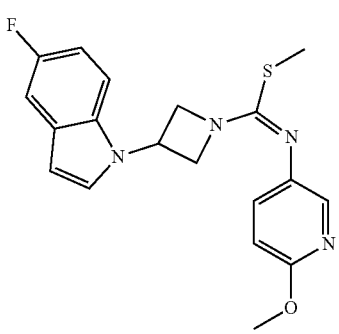

25a

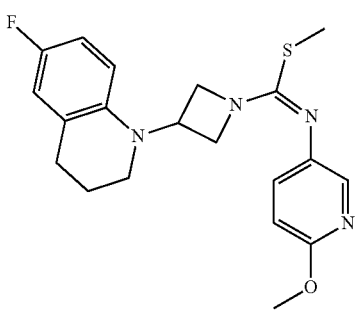

26a

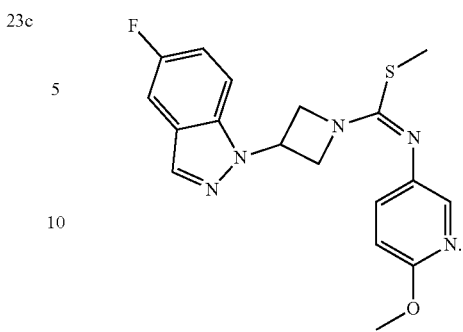

27a

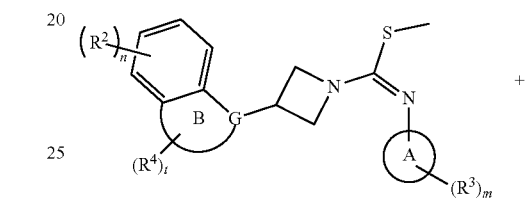

33a

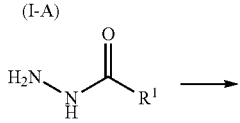

and

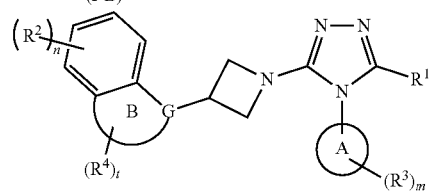

15. A method for preparing the compound of formula (I) according to claim 1 comprising:

heating a compound of formula (I-A) and a compound of formula (I-B) or a hydrochloride salt thereof under an acidic condition to obtain the compound of formula (I), wherein:
ring A, ring B, $R^1$~$R^4$, G, n, m and t are as defined in claim 1.

16. A pharmaceutical composition comprising the compound according to claim 1, and one or more pharmaceutically acceptable carriers, diluents or excipients.

17. A method of antagonizing oxytocin in a subject in need thereof, the method comprising administering to the subject the pharmaceutical composition according to claim 16.

18. A method of treating a disease or condition which benefits from inhibition of oxytocin in a subject in need thereof, the method comprising administering to the subject the pharmaceutical composition according to claim 16, wherein the disease or condition is selected from the group consisting of sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhea, congestive heart failure, arterial hypertension, liver cirrhosis, nephrotic hypertension, ocular hypertension, obsessive and behavioral disorders and neuropsychiatric disorders.

19. The method according to claim 18, wherein the disease or condition is selected from the group consisting of sexual dysfunction, sexual arousal disorder, orgasmic disorder, sexual pain disorder and premature ejaculation.

20. The compound according to claim 5, wherein ring A is:

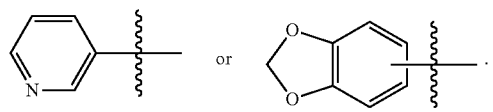

* * * * *